United States Patent
Fisher et al.

(10) Patent No.: US 11,433,068 B2
(45) Date of Patent: Sep. 6, 2022

(54) TREATMENT OF CANCERS HAVING ALTERATIONS WITHIN THE SWI/SNF CHROMATIN REMODELING COMPLEX

(71) Applicant: THE GENERAL HOSPITAL CORPORATION, Boston, MA (US)

(72) Inventors: David E. Fisher, Newton, MA (US); Qing Yu Weng, Brookline, MA (US); Shinichiro Kato, Brookline, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/331,602

(22) PCT Filed: Sep. 7, 2017

(86) PCT No.: PCT/US2017/050428
§ 371 (c)(1),
(2) Date: Mar. 8, 2019

(87) PCT Pub. No.: WO2018/049000
PCT Pub. Date: Mar. 15, 2018

(65) Prior Publication Data
US 2019/0201396 A1 Jul. 4, 2019

Related U.S. Application Data

(60) Provisional application No. 62/384,834, filed on Sep. 8, 2016.

(51) Int. Cl.
*A61K 31/4985* (2006.01)
*A61K 31/404* (2006.01)
(Continued)

(52) U.S. Cl.
CPC ........ *A61K 31/4985* (2013.01); *A61K 31/277* (2013.01); *A61K 31/404* (2013.01);
(Continued)

(58) Field of Classification Search
CPC ............ A61K 31/4985; A61K 31/4995; A61K 31/404; A61K 31/542; A61K 31/55; A61P 35/00
(Continued)

(56) References Cited

U.S. PATENT DOCUMENTS 5,290,807 A 3/1994 Folkman et al.
2011/0275157 A1 11/2011 You et al.
(Continued)

FOREIGN PATENT DOCUMENTS

WO 2015/128837 A1 9/2015
WO WO-2015192981 A1 * 12/2015 ........... C07D 401/14
WO 2016/025635 A2 2/2016

OTHER PUBLICATIONS

Sachan et al, Braz Arch Biol Technol 2015, vol. 58(4), pp. 526-539. (Year: 2015).*
(Continued)

*Primary Examiner* — Craig D Ricci
*Assistant Examiner* — Janet L Coppins
(74) *Attorney, Agent, or Firm* — Nixon Peabody LLP; David S. Resnick; Jeanne Jodoin

(57) ABSTRACT

This disclosure provides compositions and methods of treating cancer by inhibiting histone methyltransferases alone or in combination by synergistically inhibiting a histone demethylase, or a histone deacetylase (HDAC), or a bromodomain (BRD)-containing protein, or a B-Raf kinase. In particular, the cancers have deficient of SWI/SNF chromatin remodeling complexes because of mutations in one or more of the complex's subunit members.

11 Claims, 34 Drawing Sheets

Dose response of shControl vs shARID2 lines to G9a inhibitor

(51) Int. Cl.

| | |
|---|---|
| *A61K 31/55* | (2006.01) |
| *A61K 31/711* | (2006.01) |
| *A61K 31/542* | (2006.01) |
| *A61P 35/00* | (2006.01) |
| *A61K 31/277* | (2006.01) |
| *A61K 31/4995* | (2006.01) |
| *A61K 31/7105* | (2006.01) |
| *C12Q 1/6827* | (2018.01) |

(52) U.S. Cl.
CPC ........ *A61K 31/4995* (2013.01); *A61K 31/542* (2013.01); *A61K 31/55* (2013.01); *A61K 31/711* (2013.01); *A61K 31/7105* (2013.01); *A61P 35/00* (2018.01); *C12Q 1/6827* (2013.01)

(58) Field of Classification Search
USPC .................................................. 514/210.21
See application file for complete search history.

(56) References Cited

U.S. PATENT DOCUMENTS

| | | | |
|---|---|---|---|
| 2014/0128393 A1* | 5/2014 | Knutson | ............ A61K 31/5377 514/235.5 |
| 2015/0274660 A1 | 10/2015 | Pliushchev et al. | |

OTHER PUBLICATIONS

Tanaka et al, J Invest Dermatol May 2014, vol. 134(5), pp. 1470-1472 (Year: 2014).*
Shain et al, PLOS One 2013, vol. 8(1), pp. 1-11. (Year: 2013).*
Wu et al, Cancer Biol & Therapy 2014, vol. 15(6), pp. 655-664. (Year: 2014).*
Alexanrov et al., "Signatures of mutational processes in human cancer.", Nature, 500(7463):415-421 (2013).
Cao et al., "Role of Histone H3 Lysine 27 Methylation in Polycomb—Group Silencing" Science 298: 1039-1043 (2002).
Lee et al., "Clinical exome sequencing for genetic identification of rare Mendelian disorders." JAMA 312 (18):1880-1887 (2014).
Lund et al., "EZH2 in normal and malignant hematopoiesis" Leukemia 28: 44-49 (2014).
Margueron et al., "The Polycomb Complex PRC2 and its Mark in Life" Nature 469: 343-349 (2011).
Morey et al., "Polycomb group protein-mediated repression of transcription", Trends Biochem. Sci. 35(6): 323-332 (2010).
Santos et al., "Chromosome 6p amplification and cancer progression", J. Clin. Pathol. (2006).
Tan et al., "EZH2: biology, disease, and structure-based drug discovery", Acta Pharmacol. Sin. 35: 161-174 (2014).
Vire et al., "The Polycomb group protein EZH2 directly controls DNA methylation" Nature 439: 871-874 (2006).
Kim et al., "Targeting EZH2 in Cancer", Nature Medicine 22:128-134 (2016).
Biegel et al., "SWI/SNF chromatin remodeling complexes and cancer", Am J Med Genet C Semin Med Genet, 166C(3):350-66 (2014).
Bitler et al., "Synthetic lethality by targeting EZH2 methyltransferase activity in ARID1A-mutated cancers", Nat. Med. 21(3):231-238 (2015).
Casciello et al., "Functional role of G9a histone methyltransferase in cancer." Frontiers in Immunology 6(487):1-12 (2015).
Hodis et al., "A landscape of driver mutations in melanoma", Cell 150(2):251-263 (2012).
Jagani et al., "Loss of the tumor suppressor Snf5 leads to aberrant activation of the Hedgehog-Gli pathway", Nat. Med. 16(12):1429-1433 (2010).
Kadoch et al., "Mammalian SWI/SNF chromatin remodeling complexes and cancer: Mechanistic insights gained from human genomics." Science Advances 1(e1500447):1-17 (2015).
Knutson et al., "Durable tumor regression in genetically altered malignant rhabdoid tumors by inhibition of methyltransferase EZH2", Proc. Natld. Acad. Sci. 110(19):7922-7927 (2012).
Perez-Salvia et al., "Effect of epigenetic drugs on chromatin remodeling complexes disrupted in cancer." Cancer Research 75(4784) 2015 [ABSTRACT].
Rabinovich et al. "Primary rhabdoid tumor of the ovary: When large cells become small cells", Gynecol Oncol Rep, 12:64-6 (2015).
Roberts et al., "The SWI/SNF complex-chromatin and cancer", Nat. Rev. Cancer 4(2):133-142 (2004).
Sweis et al., "Discovery and development of potent and selective inhibitors of histone methyltransferase g9a", ACS Med Chem Letters 5(2):205-209 (2014).
Vedadi et al., "A chemical probe selectively inhibits G9a and GLP methyltransferase activity in cells", Nat. Chem. Biol. 7(8):566-574 (2011).
Xu et al., "Essential role of ARID2 protein-containing SWI/SNF complex in tissue-specific gene expression", J. Biol. Chem. 287(7):5033-5041 (2012).

* cited by examiner

| Gene | UNC0638 | BIX01294 |
|---|---|---|
| ARID1A | 1.000 | 0.375 |
| ARID1B | 1.000 | 0.647 |
| ARID2 | 0.0110 | 0.0555 |
| ARID3A | 0.0555 | 0.375 |
| ARID3B | 0.611 | 1.000 |
| ARID3C | 0.392 | 0.0102 |
| ARID4A | 0.269 | 0.0109 |
| ARID4B | 0.127 | 0.0555 |
| ARID5A | 0.534 | 1.000 |
| ARID5B | 0.0301 | 0.647 |
| JARID1A | 0.306 | 0.306 |
| JARID1B | 0.269 | 0.269 |
| JARID1C | 0.269 | 0.269 |
| JARID2 | 0.269 | 1.000 |
| EZH2 | 0.0623 | 0.534 |
| EHMT2 | 0.534 | 0.534 |

FIG. 10

| Target | Function | Drug | Status | Disease | Opportunities for combination therapy |
|---|---|---|---|---|---|
| EZH2 | H3K27 methyltransferase | EPZ-6438 | Phase 1/2 | Hematological malignancies, MRT | + epigenetic inhibitors ie. HDAC inhibitor with G9a inhibitor<br><br>+ other small molecule inhibitors ie. BRAF inhibitors<br><br>+ immunotherapy |
| G9a | H3K9 methyltransferase | BIX01294 UNC0638 | | Pancreatic cancer | |
| BRD4 | Recognition of H3, H4 acetylated K residues | OTX015 ZEN3365 JQ1 PFI-1 TEN010 | Phase 1 | Hematological malignancies | |
| JMJD3 | H3K27 demethylase | GSK-J4 | | ALL, DIPG | |
| HDAC | Class I, II, III deacetylases | Entinostat Trichostatin A SAHA M344 | Preclinical - Approved | CTCL | |

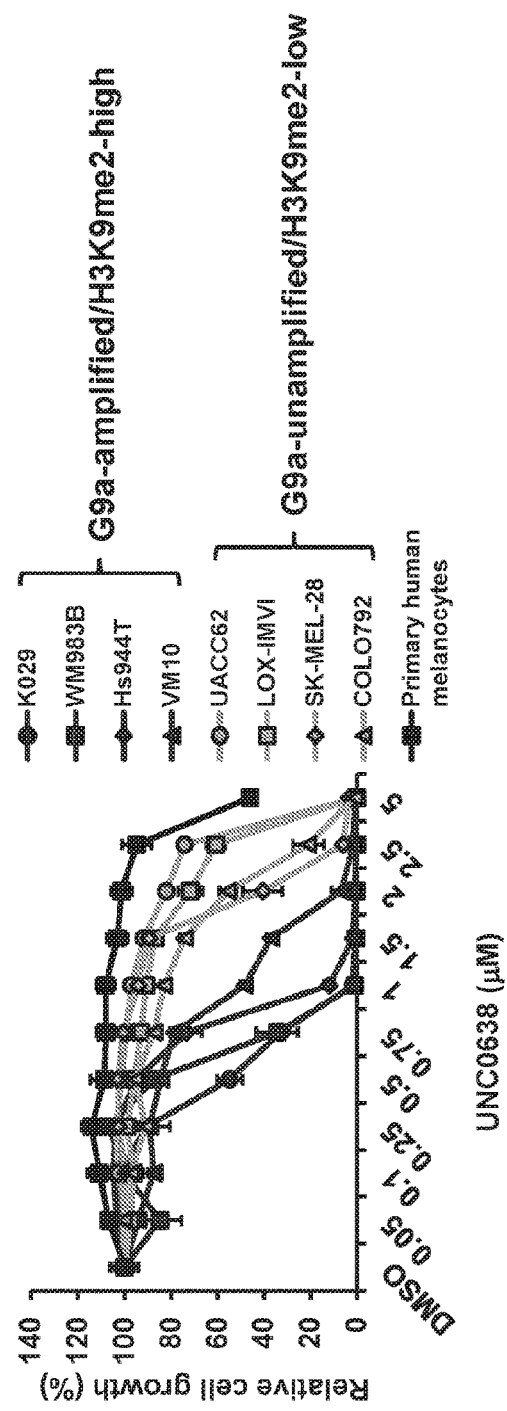
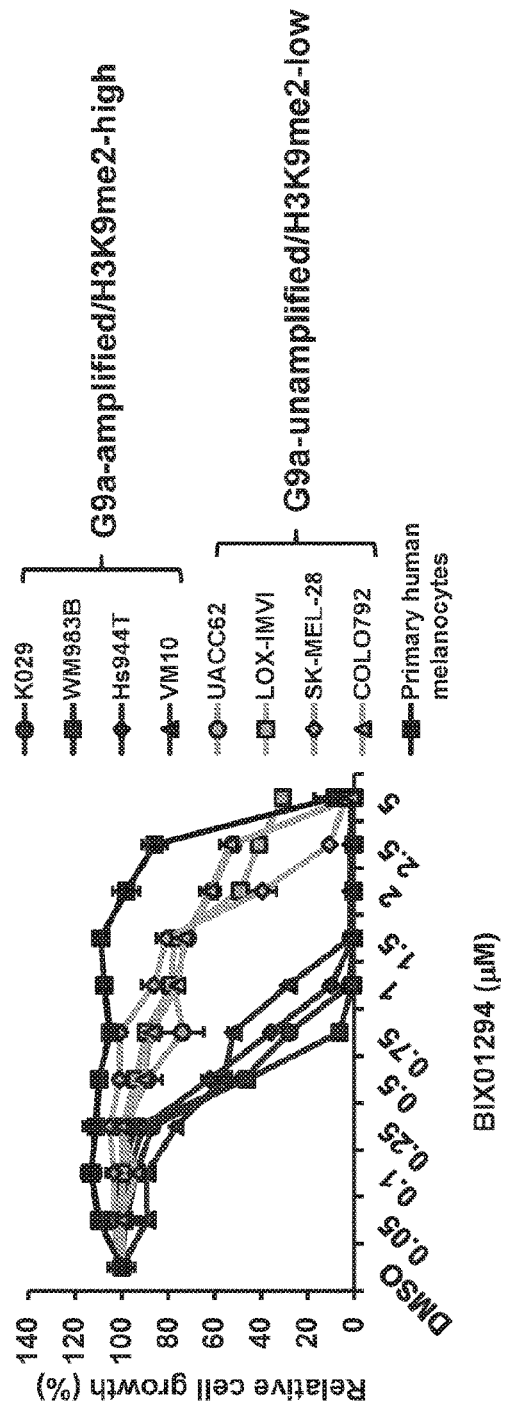

FIG. 15

| | | IC50 (μM) | |
|---|---|---|---|
| | | UNC0638 | BIX01294 |
| 6p21 amplified, high-H3K9me2 melanoma | K029 | 0.541 | 0.514 |
| | WM983B | 0.691 | 0.481 |
| | Hs944T | 0.820 | 0.606 |
| | VM10 | 0.919 | 0.757 |
| | LB373-Mel | 0.953 | 0.780 |
| 6p21 amplified, low-H3K9me2 melanoma | SK-MEL-30 | 1.23 | 0.839 |
| | MeWo | 1.71 | 1.33 |
| | UACC257 | 1.54 | 0.552 |
| | UACC62 | 14.4 | 2.59 |
| | LOX-IMVI | 4.19 | 2.08 |
| 6p21 unamplified melanoma | SK-MEL-28 | 1.90 | 1.84 |
| | COLO792 | 2.07 | 2.58 |
| | M14 | 1.32 | 1.54 |
| | MEL-JUSO | 1.03 | 1.23 |
| | WM88 | 1.07 | 1.00 |
| | SK-MEL-119 | 1.59 | 1.26 |
| Primary human melanocytes | Donor 1 | 6.45 | 1.55 |
| | Donor 2 | 19.2 | 3.51 |
| | Donor 4 | 50.4 | 1.51 |
| | Donor 5 | 68.4 | 1.86 |

Table 1  Tumours with 6p21-p23 gain or amplification

| Type of tumour | Number of tumours | Tumours with gain in 6p21-p23 (%) | Tumours with amplification in 6p21-p23 (%) |
|---|---|---|---|
| Carcinomas* | | | |
| Hepatocellular carcinoma | 409 | 22.61 | 0.20 |
| Merkel cell carcinoma | 48 | 27.10 | 2.10 |
| Basal cell carcinoma | 16 | 40.30 | 0.00 |
| Ovarian serous carcinoma | 56 | 28.60 | 0.00 |
| Transitional cell carcinoma | 133 | 9.68 | 0.51 |
| Lymphoid tumours | | | |
| Large B cell lymphoma | 360 | 8.36 | 0.07 |
| Plasmacytoma | 21 | 22.76 | 0.00 |
| Sarcomas | | | |
| Osteosarcoma | 137 | 33.19 | 3.39 |
| Malignant peripheral nerve sheath | 70 | 23.93 | 0.00 |
| Leiomyosarcoma | 136 | 9.98 | 1.64 |
| Melanomas | 91 | 31.78 | 0.00 |
| Retinoblastoma | 133 | 39.36 | 10.50 |
| Glioblastoma | 108 | 4.60 | 0.90 |
| Neuroblastoma | 303 | 22.10 | 0.17 |
| Carcinosarcoma | 23 | 21.70 | 6.31 |

*FIG. 19*

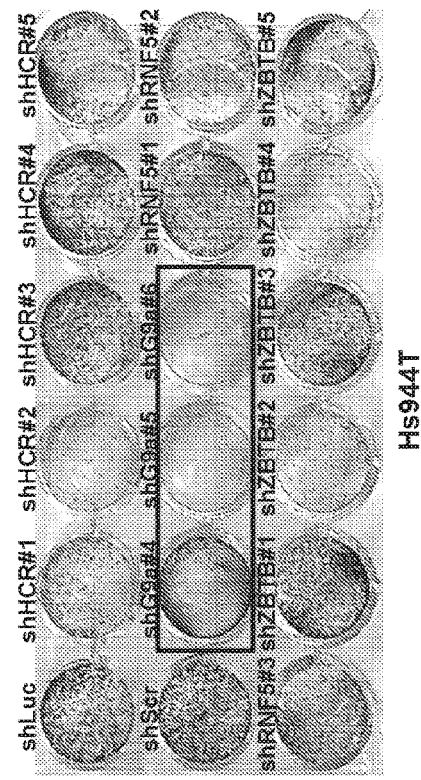

FIG. 23A

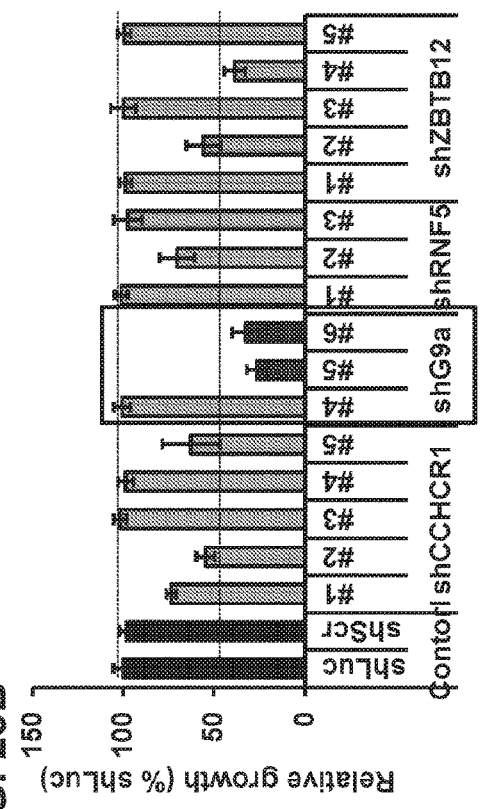

FIG. 23B

CCHCR1/HCR: coiled-coil alpha-helical rod protein 1, not well-characterized, may be a regulator of keratinocytes proliferation or differentiation G9a: euchromatic histone lysine methyltransferase 2, that methylate H3 lys9 resulting in transcriptional repression RNF5: ring finger protein 5, membrane-bound ubiquitin ligase, which regulates cell motility by targeting paxillin (overexpressed in breast cancer)

ZBTB12: zinc finger and BTB domain containing 12, not characterized

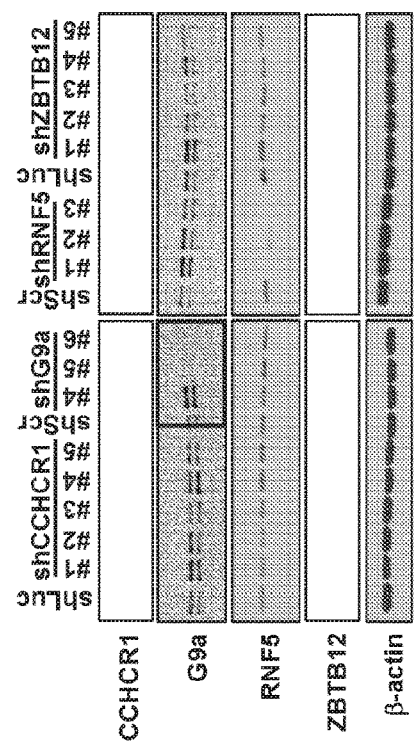

FIG. 23C

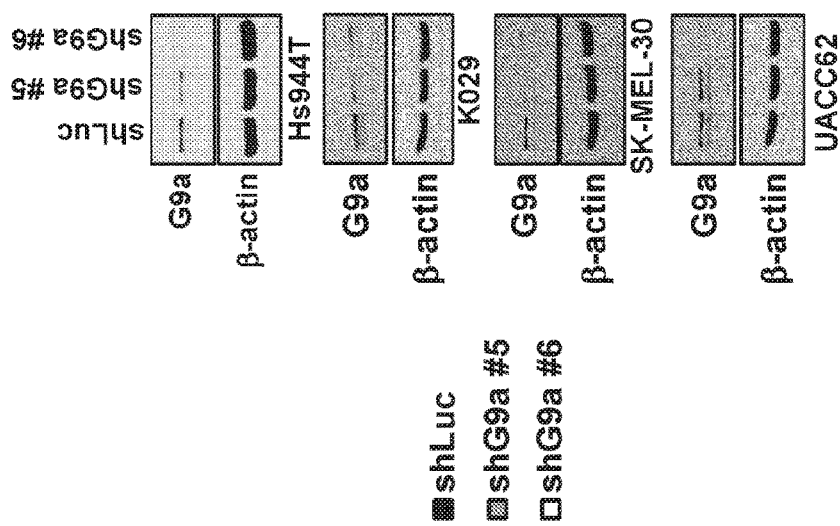
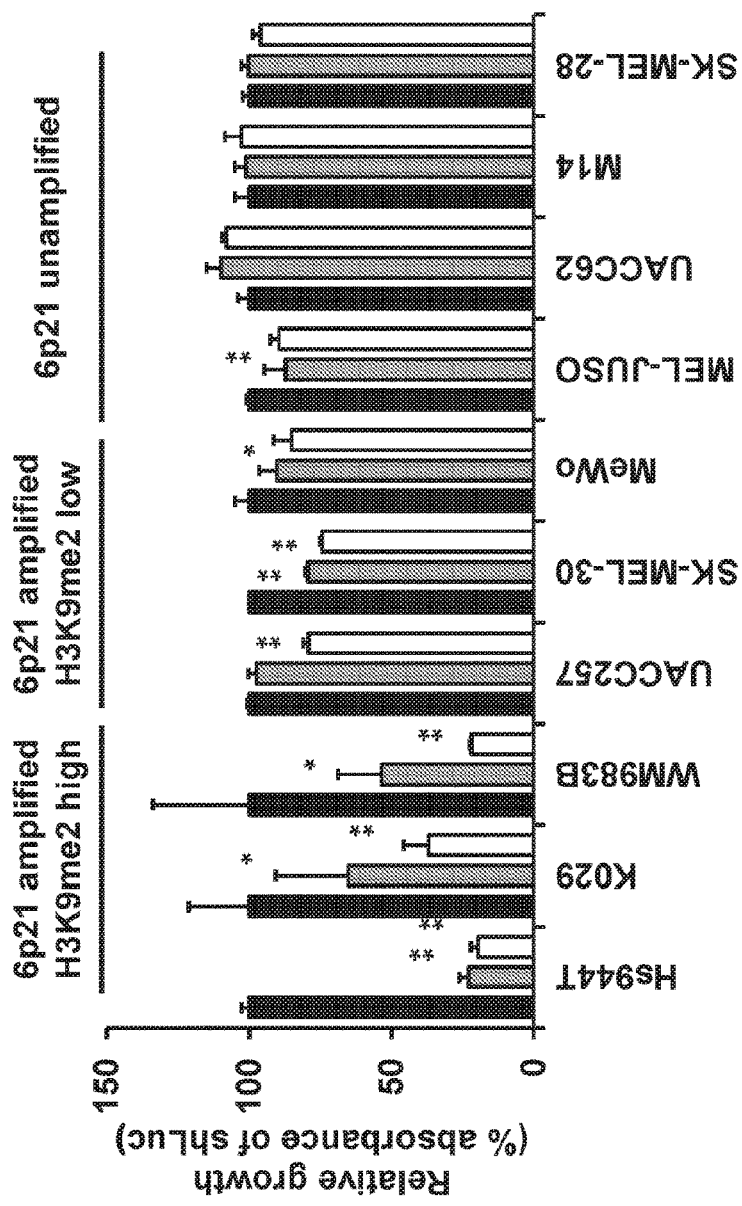
FIG. 26A
FIG. 26B

TREATMENT OF CANCERS HAVING ALTERATIONS WITHIN THE SWI/SNF CHROMATIN REMODELING COMPLEX

CROSS-REFERENCE TO RELATED APPLICATIONS

This Application is a 35 U.S.C. § 371 National Phase Entry Application of International Application No. PCT/US2017/050428 filed Sep. 7, 2017, which designated the U.S., and which claims benefit under 35 U.S.C. § 119(e) of the U.S. Provisional Application No. 62/384,834 filed Sep. 8, 2016, the contents of which are incorporated herein by reference in their entireties.

FIELD OF THE DISCLOSURE

This disclosure relates to cancer therapeutics and the use of histone methyltransferase inhibitors for the treatment of cancer, especially aggressive invasive cancers.

BACKGROUND

Cancer has a major impact on society in the United States and across the world. Cancer is among the leading causes of death worldwide. In 2012, there were 14 million new cases and 8.2 million cancer-related deaths worldwide.

Humans have declared war against cancer for well over four decades. Despite years of research into the development of numerous methods of treatment and prevention, and understanding of the biology of cancer development, many types of cancers remain quite common. In 2016, an estimated 1,685,210 new cases of cancer will be diagnosed in the United States alone and 595,690 people will die from the disease. The most common cancers in 2016 are breast cancer, lung and bronchus cancer, prostate cancer, colon and rectum cancer, bladder cancer, melanoma of the skin, non-Hodgkin lymphoma, thyroid cancer, kidney and renal pelvis cancer, leukemia, endometrial cancer, and pancreatic cancer. Continued search and development of more anti-cancer agents to complement or replace existing treatments is needed.

SUMMARY

This disclosure concerns the use of G9a/GLP inhibitors in the treatment of cancers that have alterations in the SWI/SNF ((SWItch/Sucrose Non-Fermentable) chromatin remodeling complex. The G9a/GLP inhibitors are used alone or with other cancer therapies or with other inhibitors of chromosomal epigenetic modifiers such as modifying enzymes. G9a/GLP inhibitors are histone methyltransferase inhibitors.

Embodiments of the present disclosure are based, in part, on the discovery that certain cancers that have alterations in the SWI/SNF chromatin remodeling complex are uniquely susceptible histone methyltransferase inhibitors. The SWI/SNF complex functions in epigenetic regulation and is required for normal cell development and survival. It is altered in a significant portion of melanomas as well as other cancers (see FIG. 1) and presents a particular therapeutic challenge. This is because the oncogenic changes are not driven directly by mutated proteins or molecules targetable by available drugs. Solely as prove of principle, the inventors showed that melanomas deficient in the SWI/SNF complex were susceptible G9a/GLP inhibitor. Melanomas is was selected an example of the various types of cancer. The inhibitor targets the histone methyltransferase heteromeric complex G9a/GLP, which catalyzes dimethylation of the H3K9 residue. The inventors demonstrated the specificity of this vulnerability using both cell lines with engineered knockdown of SWI/SNF components as well as melanomas intrinsically deficient in the SWI/SNF complex, that is cancer cells that are naturally deficient in the SWI/SNF complex. Cells with intact SWI/SNF complex function are spared from the cytotoxic effects of the G9a/GLP inhibitors. Therefore, cancers that are deficient in the SWI/SNF complex have unique epigenetic dependencies, the vulnerability to histone methyltransferase inhibitors. This presents a new area to target in cancer therapy, that of inhibiting chromosomal epigenetic processes in these cancer cells.

The inventors also discovered that these cancers that are deficient in the SWI/SNF complex are also vulnerable to other inhibitors of epigenetic modification or other small molecule inhibitors in conjunction with the histone methyltransferase inhibitors. The other inhibitors include but are not limited to inhibitors of histone deacetylases, bromodomains, and of a B-Raf signal transduction protein kinase which is involved in directing cell growth. These various inhibitors having different targeted proteins work synergistically with each other on the cancers that are deficient in the SWI/SNF complex, such that each inhibitor is more effective at promoting cell death together with other inhibitors, requiring lower inhibitor amount compared to when each inhibitor is used alone on the cancer cells. In other words, administering histone methyltransferase inhibitors can enhance drug efficacy of other inhibitors of epigenetic modification or small molecule inhibitors that are already used in cancer therapy.

Accordingly, it is the objective of this disclosure to provide alternative cancer treatments that take advantage of the unique epigenetic dependencies in cancer cells having alterations in the SWI/SNF chromatin remodeling complex. In one embodiment, the alternative cancer treatment is to inhibit histone methyltransferase enzymes in these cancer cells and consequently promote apoptosis or cell death of thus inhibited cancer cells. In other embodiments, the alternative cancer treatment is to inhibit other enzymes involved in some of the chromosomal epigenetic modifications of DNA, for example, acetylation, demethylation and deacetylation, that are known in the art. In other embodiments, the alternative cancer treatment is to inhibit other protein kinases involved in directing cell growth, e.g., B-Raf, or a mutant B-Raf. For example, non-limiting oncogenic B-Raf mutations include V600E, V600K, V600L, V600R, V600M, K601E D594G, G469A, G469V, G466V, L597R, N581S, L597Q, G466, R461I, I462S, G463E, G463V G465A, G465E, G465V, G468E, N580S, E585K, D593V, F594L, G595R, L596V, T598I, V599D, V599E, V599K, and V599R. Non-limiting protein kinases that can be targeted for cancer treatment include JAK, ABL, EGFR, and VEGFR. In other embodiments, more than one type of inhibitors are used in combinations, resulting in more than one epigenetic process or kinase are inhibited simultaneously in the cancer cells.

In one embodiment, provided here in is a method for treating cancer in a subject comprising administering to a subject in need thereof a therapeutically effective amount of an inhibitor of a histone methyltransferase, or therapeutically effective amount of a composition comprising an inhibitor of a histone methyltransferase, wherein the cancer of the subject has been determined to have an alteration in the SWI/SNF chromatin remodeling complex.

In one embodiment, provided here in is a method for treating of cancer in a subject in need thereof, the method comprising first determining an alteration of SWI/SNF chromatin remodeling complex from cancer cells derived from a subject; and administering to a subject an inhibitor of a histone methyltransferase, or therapeutically effective amount of a composition comprising an inhibitor of a histone methyltransferase when there is an alteration in the SWI/SNF chromatin remodeling complex in the cancer cells in order to treat the subject.

In one embodiment of any one of the treatment method described, the inhibitor of a histone methyltransferase is an inhibitor of the histone methyltransferase heteromeric complex G9a/GLP, also known as a G9a inhibitor. G9a/GLP catalysis the methylation of histone 3 lysine residue at the $9^{th}$ position in the histone polypeptide, abbreviated as H3K9.

In one embodiment of any one of the treatment method described, the cancer in the subject also has an alteration in the histone methyltransferase heteromeric G9a/GLP complex. In one embodiment, the alteration results in increased in activity of the complex and consequently increased methylation of DNA.

In one embodiment of any one of the treatment method described, the inhibitor of a histone methyltransferase is an inhibitor of the histone methyltransferase EZH2. EZH2 catalysis the methylation of histone 3 lysine residue at the $27^{th}$ position in the histone polypeptide, abbreviated as H3K27.

In one embodiment, provided here in is a method for treating of cancer in a subject in need thereof, the method comprising administering a composition comprising an inhibitor of a histone methyltransferase EZH2 wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase EZH2, and an inhibitor of a histone methyltransferase G9a, wherein the cancer of the subject has been determined to have an alteration in the SWI/SNF chromatin remodeling complex.

In one embodiment of any one of the treatment method described, the inhibitor of a histone methyltransferase described herein is formulated as a composition. For example, formulated as a composition for an oral or systemic administration or sustain delivery.

In one embodiment of any one of the treatment method described, additional inhibitors are administered in conjunction with the histone methyltransferase inhibitor. For example, the addition inhibitors are histone deacetylase (HDAC) inhibitors, bromodomain inhibitors (BRD), histone demethylase inhibitors, and BRaf (B-Raf) inhibitors. The various types of inhibitors can be administered simultaneously in a mixed formulation, e.g., a cocktail of inhibitors, or be administered sequentially, one inhibitor type after another. Moreover, the administration can be spaced out over several days. For example, one inhibitor type is administered on day 1 and a second inhibitor type is administered on day 2 or 3.

In one embodiment, provided here in is a method for treating of cancer in a subject in need thereof, the method comprising administering a composition comprising an inhibitor of a histone methyltransferase G9a and a HDAC inhibitor, wherein the cancer of the subject has been determined to have an alteration in the SWI/SNF chromatin remodeling complex. Histone deacetylases (EC 3.5.1.98, HDAC) are a class of enzymes that remove acetyl groups (O═C—CH3) from an ε-N-acetyl lysine amino acid on a histone, allowing the histones to wrap the DNA more tightly. This is important because DNA is wrapped around histones, and DNA expression is regulated by acetylation and de-acetylation. Its action is opposite to that of histone acetyltransferase. HDAC proteins are also called lysine deacetylases (KDAC), to describe their function rather than their target, which also includes non-histone proteins.

In one embodiment, provided here in is a method for treating of cancer in a subject in need thereof, the method comprising administering a composition comprising an inhibitor of a histone methyltransferase EZH2 and a HDAC inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2 and a HDAC inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase EZH2 and an inhibitor for a B-Raf enzyme (a B-Raf inhibitor), wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a and a B-Raf inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2 and a B-Raf inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase EZH2 and an inhibitor for a member of the BET (bromodomain and extra terminal domain) family of bromodomain proteins (BRD) (a BRD inhibitor), wherein the cancer of the subject has been determined to have an alteration in the SWI/SNF chromatin remodeling complex. A bromodomain is an approximately 110 amino acid protein domain that recognizes acetylated lysine residues, such as those on the N-terminal tails of histones. Bromodomains, as the "readers" of lysine acetylation, are responsible in transducing the signal carried by acetylated lysine residues and translating it into various normal or abnormal phenotypes. Bromodomain-containing proteins are epigenetic reader proteins.

In one embodiment, provided here in is a method for treating of cancer in a subject in need thereof, the method comprising administering a composition comprising an inhibitor of a histone methyltransferase G9a and a BRD inhibitor, wherein the cancer of the subject has been determined to have an alteration in the SWI/SNF chromatin remodeling complex.

In one embodiment, provided here in is a method for treating cancer in a subject in need thereof, the method comprising administering a composition comprising an inhibitor of a histone methyltransferase G9a. an inhibitor of a histone methyltransferase EZH2, and a BRD inhibitor, wherein the cancer of the subject has been determined to have an alteration in the SWI/SNF chromatin remodeling complex.

In one embodiment, provided herein is an inhibitor of a histone methyltransferase, an inhibitor of a histone demethylase, a HDAC inhibitor, a bromodomain inhibitor, or B-Raf inhibitor, or combinations thereof, for use in the treatment of cancer in a subject when the cancer of the subject has been determined to have an alteration in the SWI/SNF chromatin remodeling complex.

In one embodiment, provided herein is a combination of a histone methyltransferase inhibitor and at least a second inhibitor selected from the group consisting of an inhibitor of a histone demethylase, a HDAC inhibitor, a bromodomain inhibitor, and a B-Raf inhibitor for use in the treatment of cancer in a subject when the cancer of the subject has been determined to have an alteration in the SWI/SNF chromatin remodeling complex.

In one embodiment, provided herein is use of an inhibitor of a histone methyltransferase, an inhibitor of a histone demethylase, a HDAC inhibitor, a bromodomain inhibitor, or B-Raf inhibitors, or combinations thereof, for use in the manufacture of a medicament for the treatment of cancer in a subject when the cancer of the subject has been determined to have an alteration in the SWI/SNF chromatin remodeling complex.

In one embodiment, provided herein is use of a combination of a histone methyltransferase inhibitor and at least a second inhibitor selected from the group consisting of an inhibitor of a histone demethylase, a HDAC inhibitor, a bromodomain inhibitor, or B-Raf inhibitor for the treatment of cancer in a subject when the cancer of the subject has been determined to have an alteration in the SWI/SNF chromatin remodeling complex.

In one embodiment, provided herein is use of a composition comprising a histone methyltransferase inhibitor and at least a second inhibitor selected from the group consisting of an inhibitor of a histone demethylase, a HDAC inhibitor, a bromodomain inhibitor, or B-Raf inhibitor for the treatment of cancer in a subject when the cancer of the subject has been determined to have an alteration in the SWI/SNF chromatin remodeling complex.

In one embodiment, the compositions described herein are formulated for oral or systemic application to the subject.

In one embodiment, the subunit members of the SWI/SNF chromatin remodeling complex that are tested for alterations are selected from the group consisting of BRM/SMARCA2; BRG1/SMARCA4; ARID1A; ARID2; SMARCR2; SMARCR1; SMARCB1; and PBRM1.

In one embodiment, the one or more subunit members of the SWI/SNF chromatin remodeling complex that are disclosed in Table 1 is tested for alterations therein.

In one embodiment, the alteration the SWI/SNF chromatin remodeling complex is the result in a deficiency in one or more of the subunit member of the complex in the subject.

In one embodiment the deficiency is due to a mutation in the gene encoding the subunit member.

In one embodiment, the deficiency is determined by DNA sequencing.

In one embodiment, the mutation in the gene encoding the subunit member is a deletion, an insertion, a single nucleotide variant (SNV), or an amplification. Multiple types of mutations consisting of deletion, SNV, insertion, and amplification may be present in the gene encoding a subunit member.

In one embodiment, the SNV is an inactivating SNV.

In one embodiment of the inhibitors described herein, inhibitors of a histone methyltransferase, a HDAC, a B-Raf, and a BRD are small molecules or nucleic acids.

In one embodiment, non-limiting examples of the histone methyltransferase inhibitor that can be used for the treatment of cancers with alterations the SWI/SNF chromatin remodeling complex include AMI-1, A-366, BIX-01294, BIX01338, BRD4770, chaetocin, UNC0224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, and EPZ-6438. In other embodiments, the histone methyltransferase inhibitor include but is not limited to those disclosed in United States Patent Application No: US20150274660, the contents are incorporated herein by reference in its entirety.

In one embodiment, the BRD inhibitor targets the BRD4 protein which recognizes histone 3 (H3), and histone 4 (H4) acetylated lysine residues. BRD4 is a member of the BET (bromodomain and extra terminal domain) family, which also includes BRD2, BRD3, and BRDT. BRD4, similar to other BET family members, contains two bromodomains that recognize acetylated lysine residues. In other embodiments, the BRD inhibitor targets all bromodomains of the BET family, the bromodomain of all bromodomain-containing proteins, and also the In one embodiment, non-limiting examples of the BRD inhibitor that can be used for the treatment of cancers with alterations the SWI/SNF chromatin remodeling complex include OTX015, CPI-203, PFI-3, PFI-4, GSK1324726A (I-BET726), MS436, OF-1, bromosporine, SGC-CBP30, GSK2801 ZEN3365, JQ1, PF-1, RVX-208, PFI-1 (PF-6405761), I-BET151 (GSK1210151A) and TEN010.

In one embodiment, non-limiting examples of the histone demethylase inhibitor that can be used for the treatment of cancers with alterations the SWI/SNF chromatin remodeling complex include GSKJ4, GSK J1, OG-L002, JIB-04, SP2509, ORY-1001 (RG-6016), IOX1, GSK-LSD1 2HCl, and GSK J1.

In one embodiment, the HDAC inhibitor is a pan-HDAC inhibitor, that affecting more than one class of HDAC (classes I, II, III and IV) and more than one of HDAC1, 2, 3, 4, 5, 6, 7, 8, 9, 10, and 11.

In one embodiment, non-limiting examples of the HDAC inhibitor that can be used for the treatment of cancers with alterations the SWI/SNF chromatin remodeling complex include M344, Vorinostat (suberoylanilide hydroxamic acid, SAHA, MK0683), entinostat (MS-275), panobinostat (LBH589), trichostatin A (TSA), mocetinostat (MGCD0103), Belinostat (PXD101), Romidepsin (FK228, Depsipeptide), MC1568, Tubastatin A HCl, Givinostat (ITF2357), LAQ824 (Dacinostat) CUDC-101 Quisinostat (JNJ-26481585) 2HCl, Pracinostat (SB939) PCI-34051 Droxinostat Droxinostat PCI-24781 (Abexinostat), RGFP966, AR-42, Rocilinostat (ACY-1215), Valproic acid sodium salt (Sodium valproate), CI994 (Tacedinaline), CUDC-907, Tubacin, RG2833 (RGFP109), Resminostat Sodium Phenylbutyrate, Tubastatin A, HPOB, Tasquinimod, 4SC-202 TMP269 CAY10603 BRD73954 BG45 LMK-235, and Nexturastat A.

In one embodiment, non-limiting examples of the BRaf inhibitor that can be used for the treatment of cancers with alterations the SWI/SNF chromatin remodeling complex include BAY43-9006 (Sorafenib, Nexavar), PLX4032 (Vemurafenib), GDC-0879, SB590885 S7108 Encorafenib (LGX818), RAF265 (CHIR-265), Dabrafenib (GSK2118436), TAK-632, PLX-4720, CEP-32496, Sorafenib Tosylate (Bay 43-9006), Sorafenib Sorafenib, and AZ 628.

In one embodiment, the inhibitor described herein or combination thereof is administered by a route selected from the group consisting of oral, systemic, intravenous, intramuscular, subcutaneous, transdermal, intradermal, topical, intraperitoneal, intrathecal, intrapleural, intrauterine, rectal, vaginal, intrasynovial, intraocular/periocular, intratumor, aerosol, and parenteral administration.

In one embodiment, the inhibitor described herein or combination thereof or composition comprising the inhibitor described herein or combination thereof is administered in conjunction with at least one additional cancer therapy to achieve a combination cancer therapy.

In one embodiment, the at least one additional cancer therapy is selected from chemotherapy, radiation therapy, immunotherapy, surgery, hormone therapy, stem cell therapy, targeted therapy, gene therapy, and precision therapy.

In one embodiment, the at least one additional cancer therapy is not a histone methyltransferase inhibitor, or a histone demethylase inhibitor, or a HDAC inhibitor, or a BRaf inhibitor, or a BRD inhibitor.

In one embodiment, the at least one additional cancer therapy is not AMI-1, A-366, BIX-01294, BIX01338, BRD4770, chaetocin, UNCO224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EIL MI-2 (Menin-MLL Inhibitor), MI-3 (Menin-MLL Inhibitor), PFI-2, GSK126, EPZ004777, BRD4770, or EPZ-6438.

In one embodiment, the at least one additional cancer therapy is not OTX015, CPI-203, PFI-3, PFI-4, GSK1324726A (I-BET726), MS436, OF-1, bromosporine, SGC-CBP30, GSK2801 ZEN3365, JQ1, PF-1, RVX-208, PFI-1 (PF-6405761), I-BET151 (GSK1210151A) or TEN010

In one embodiment, the at least one additional cancer therapy is not GSKJ4, GSK J1, OG-L002, JIB-04, SP2509, ORY-1001 (RG-6016), IOX1, GSK-LSD1 2HCl, or GSK J1

In one embodiment, the at least one additional cancer therapy is not M344, Vorinostat (suberoylanilide hydroxamic acid, SAHA, MK0683), entinostat (MS-275), panobinostat (LBH589), trichostatin A (TSA), mocetinostat (MGCD0103), Belinostat (PXD101), Romidepsin (FK228, Depsipeptide), MC1568, Tubastatin A HCl, Givinostat (ITF2357), LAQ824 (Dacinostat) CUDC-101 Quisinostat (JNJ-26481585) 2HCl, Pracinostat (SB939) PCI-34051 Droxinostat Droxinostat PCI-24781 (Abexinostat), RGFP966, AR-42, Rocilinostat (ACY-1215), Valproic acid sodium salt (Sodium valproate), CI994 (Tacedinaline), CUDC-907, Tubacin, RG2833 (RGFP109), Resminostat Sodium Phenylbutyrate, Tubastatin A, HPOB, Tasquinimod, 4SC-202 TMP269 CAY10603 BRD73954 BG45 LMK-235, or Nexturastat A.

In one embodiment, the at least one additional cancer therapy is not BAY43-9006 (Sorafenib, Nexavar), PLX4032 (Vemurafenib), GDC-0879, SB590885 S7108 Encorafenib (LGX818), RAF265 (CHIR-265), Dabrafenib (GSK2118436), TAK-632, PLX-4720, CEP-32496, Sorafenib Tosylate (Bay 43-9006), Sorafenib Sorafenib, or AZ 628.

In one embodiment, the subject is a mammal.

In one embodiment, the mammal is a human.

In one embodiment, the composition or the inhibitor described herein or combination thereof further comprises a pharmaceutically acceptable carrier.

In one embodiment provided herein is a method for treating cancer, comprising administering to a subject in need thereof a therapeutically effective amount of a histone methyltransferase inhibitor wherein the cancer cells from a subject have been determined to have an at least 3-fold increase of H3K9me2 levels compared to reference levels. In one embodiment, the cancer cells have further been determined to have an at least one additional gene copy of the G9a and/or GLP gene compared to reference gene copy numbers.

In one embodiment provided herein is a method for treating cancer, the method comprising determining the levels of H3K9me2 in a sample of cancer cells derived from a subject, and administering to a subject a composition comprising a histone methyltransferase inhibitor when the H3K9me2 level are increased at least 3-fold increase compared to reference levels. In one embodiment, the cancer cells have further been determined to have an at least one additional gene copy of the G9a and/or GLP gene compared to reference gene copy numbers.

In one embodiment, the composition comprising a histone methyltransferase inhibitor further comprises an inhibitor of a histone methyltransferase EZH2, and an inhibitor for a B-Raf enzyme, and an inhibitor for a member of the BET family of bromodomain proteins (BRD), and/or an inhibitor for a histone deacetylase (HDAC).

Definitions

As used herein, the term "alteration" or "aberration" when used in the context of the SWI/SNF chromatin remodeling complex refers to deficiency in one or more of the subunits making up the complex. The SWI/SNF (SWItch/Sucrose Non-Fermentable) complex is an evolutionarily conserved multi-subunit, nucleosome/chromatis remodeling complex found in both eukaryotes and prokaryotes. In simpler terms, it is a group of proteins that associate to remodel the way DNA is packaged. The complex uses the energy of ATP hydrolysis to mobilize nucleosomes and remodel chromatin. It is composed of several proteins, products of the SWI and SNF genes, and other polypeptides. These proteins are also referred to as subunit members that make up the complex. It possesses a DNA-stimulated ATPase activity and can destabilise histone-DNA interactions in reconstituted nucleosomes in an ATP-dependent manner. The terms "alteration" or "aberration" are used interchangeably. In the yeast, the SWI and SNF genes are SWI1, SWI2/SNF2, SWI3, SWI5, SWIG. The human analogs of SWI/SNF are BAF (SWI/SNF-A) and PBAF (SWI/SNF-B). BAF in turn stands for "BRG1- or HRBM-associated factors", and PBAF is for "polybromo-associated BAF". For example, inactivation of the SNF5 gene would result in an "alteration" in the complex. (See C. W. M. Roberts & S. H. Orkin, 2014, Nature Reviews Cancer 4: 133-142, "The SWI/SNF complex—chromatin and cancer," and J. A. Biegel, et al., 2014, Am. J.

Med. Genet. C. Semin. Med. Genet., 166C(3):350-66, "SWI/SNF Chromatin Remodeling Complexes and Cancer").

The mammalian SWI/SNF (mSWI/SNF) complex functions as a tumor suppressor in many human malignancies. It was first identified in 1998 as a tumor suppressor in rhabdoid tumors, a rare pediatric malignancy. Through DNA sequencing, many tumors were sequenced for the first time around 2010, and the DNA sequencing results revealed that SWI/SNF is a major tumor suppressor in a number of diverse malignancies. A meta-analysis of many sequencing studies demonstrated SWI/SNF to be mutated in approximately 20% of human malignancies.

As used herein, the term "deficiency" when used in the context of a protein subunit member that making up the SWI/SNF chromatin remodeling complex refers to reduced protein expression or function of the subunit. Often, lower expression or function is due to a mutation in the gene of the subunit member, an inactivating mutation in the gene.

As used herein, the term "ARID2 deficiency" refers to reduced protein expression of the ARID2 subunit that make up the remodeling complex.

As used herein, the term "inactivating mutation" when used in the context of a gene, refers to any mutation (genetic alteration of the DNA) which finally leads to a reduced function or even to a complete loss of function of a protein.

As used herein, the term "inactivating SNV" are single nucleic base change or mutation in a gene which ultimately diminish the function or expression of the gene. These can be defined as causing an amino acid change from a residue that is evolutionarily conserved across species to an amino acid that is not otherwise seen across species at the same position.

As used herein, the term "gene" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "comprising" or "comprises" is used in reference to methods, and respective component(s) thereof, that are essential to the claims, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

As used herein, the term "an epigenetic modification" refers to any direct or indirect changes in the local environmental factors on genes in chromosomes and chromatin that thereby alters the way the genes are expressed, i.e., switch genes on and off and affected how cells read genes. Examples of epigenetic modifications include but are not limited to covalent modifications of either DNA (e.g. cytosine methylation and hydroxymethylation) or of histone proteins (e.g. lysine acetylation, lysine and arginine methylation, serine and threonine phosphorylation, and lysine ubiquitination and sumoylation). In some embodiments, artificially changing the epigenetic modification state and its consequential effects on gene expressions may synergistically enhance the cytotoxic/apoptotic effects of chemotherapy drugs that also influence the epigenetics of the cancer cell.

As used herein, the term "enhance drug efficacy" with reference to an inhibitor described herein in refers to a first inhibitor increasing the desired therapeutic effects of a second therapy administered for cancer, e.g., an inhibitor of an enzyme. Wherein the administered second therapy is a drug such as a chemotherapy drug with cytotoxic/apoptotic effects, the first inhibitor would increase the cytotoxic/apoptotic effects of the chemotherapy drug. In one embodiment, the increase is at least 5% over the drug efficacy or cytotoxic/apoptotic effects of the drug noted in the absence of the an inhibitor. In one embodiment, the "enhance drug efficacy" would mean that less chemotherapy drug would need to be administered to the subject. In one embodiment, the "enhance drug efficacy" would mean that the subject would experience less toxic side effects of the drug with the administration of a less amount of the drug. In one embodiment, the term "enhance drug efficacy" include synergistic effects between the first inhibitor and the second therapy administered for cancer. In one embodiment, the synergistic effects between the first inhibitor and the second therapy administered for cancer comprise at least a reduction in the amount/dosage of either the first inhibitor or the second therapy administered for cancer to achieve the same level of cancer therapy. the second therapy administered for cancer As used herein, the term "apoptosis" refers to a natural process of self-destruction in certain cells that is determined by the genes and can be initiated by a stimulus or by removal of a repressor agent. "Apoptosis" is also known as programmed cell death. Several biochemical events lead to characteristic cell changes (morphology) and death. These changes include but are not limited to cell blebbing, cell shrinkage, nuclear fragmentation, chromatin condensation, and chromosomal DNA fragmentation. Analysis of apoptosis can be performed by any method known in the art. Non-limiting examples include cell free apoptotic assay, DNA fragmentation assay, DNA laddering assay, terminal transferase dUTP nick end labeling (TUNEL) assay and Annexin A5 (or annexin V) detection. The DNA can be labeled with propidium iodide or 7-AAD and analysed by flow cytometry.

As used herein, the term "inhibit" or "inhibition" with respect to an enzyme (kinases, methylases, acetylase, demethylase) inhibitor described herein means the reduction in the end-product of the enzymatic activity of the respective enzyme. For BRD proteins, the term "inhibit" or "inhibition" means reduction in the acetylated DNA binding or reduction in cellular events that is a consequence of the natural binding of the BRD proteins to their respective binding partners in the acetylated DNA. For example, for a histone methyltransferase inhibitor, inhibition of the methyltransferase means a reduction of the methylated histones at lysines (e.g., H3K4, H3K9, and H3K27) and other amino acid residues. Inhibition includes slowing the rate of methylated enzymatic end-products. Inhibition of the methyltransferase means a reduction of the number of methyl group transferred. Inhibition includes slowing the rate of methylated enzymatic end-products. For example, for a histone demethylase, inhibitor e.g., Lysine-specific histone demethylase 1A (KDM1A) also known as lysine (K)-specific demethylase 1A (LSD1), inhibition of the demethylase means an increase of the methylated histones. Inhibition includes slowing the rate of non-methylated and mono-methylated enzymatic end-products. For example, for a histone deacetylase inhibitor, e.g., SAHA, inhibition of histone deacetylase results in the accumulation of acetylated histones and acetylated proteins. For example, inhibitors of BRD inhibit the binding of the BRD protein to acetylated proteins, prevents cell signaling that ultimately promote cell proliferation. Inhibition includes increase apoptosis, or decrease mitosis or both. Analysis of the enzymatic activity in the presence of a respective inhibitor can be assayed by any method known in the art. For example, the method described by Y. Tsukada and K. I. Nakayama, Cold Spring Harb. Protoc. 2010, protocol #5512; and by using screening kits such as the LSD1 Inhibitor Screening Assay Kit for Lysine-Specific Demethylase 1 by Cayman Chemical catalog #700120. Other methods are described in E. Korb et al., Nat. Neurosci. 2015, 18:1464-73; H. Herrmann et al., Oncotarget. 2012, 3:1588-99; D. P. Mould et al., Medicinal Research Reviews, 2015, 35: 586-618; L. M. Bulter et al., 2002, Proc. Natl. Acad. Sci. NY, 99: 11700-11705; and H. U. Kaniskan et al., 2015, J. Med. Chem. 58:1596-1629, and the references are incorporated herein by reference in their entirety. The reduction or increase can by about 20%, about 30%, about 40%, about 50%, about 60%, about 70%, about 80%, about 90%, about 100% compared to a control which is an assay conducted in the absence of the inhibitor.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder. In one embodiment, the reference level is that in the absence of the inhibitor added.

The terms "increase" or "increased" are all used herein to mean a increase by a statistically significant amount. In some embodiments, "increase" or "increased" typically means a decrease by at least 10% as compared to a reference level (e.g. the absence of a given treatment) and can include, for example, an increase by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. When used herein in reference to H3K9me2, "increase" can refer to an increase of H3K9me2 levels of at least 1-fold, at least 2-fold, at least 3-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, at least 100-fold or more compared to reference levels. When used in reference to G9a and or GLP gene copy numbers, "increase" can refer to the gene copy number increased by at least 1, at least 2, at least 3, at least 4, at least 5, at least 6, at least 7, at least 8, at least 9, at least 10 or more compared to reference gene copy numbers.

As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder. In one embodiment, the reference level is that in the absence of the inhibitor added As used herein the term "cell proliferation" or "cell growth" refers to reproduction and increase in cell number, i.e., cell division.

As used herein, a "tissue sample" refers to a portion, piece, part, segment, or fraction of a tissue or organ which is obtained or removed from an intact tissue of a subject, preferably a human subject or a primate subject. In one embodiment, the tissue sample is a blood sample. In another embodiment, the tissue sample is a bone marrow sample. In one embodiment, the tissue sample is a cerebrospinal fluid sample. In one embodiment, the tissue sample is portion of a solid organ such as the lung, breast, colon, bladder, stomach, uterine, skin, ovary, liver, cervix. vagina, rectum, prostate, throat, thyroid, muscle, mouth, tongue and brain.

As used herein, a "tumor sample" refers to a portion, piece, part, segment, or fraction of a tumor, for example, a tumor which is obtained or removed from a subject (e.g., removed or extracted from a tissue of a subject), preferably a human subject.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "cancer therapy" or "cancer treatment" refers to a therapy useful in treating cancer. Examples of anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

In one embodiment, "administration" and "treatment," as it applies to a subject, refers to the contact of an exogenous pharmaceutical, therapeutic, or composition to the subject. In another embodiment, "administration" and "treatment," as it applies to a subject, refers to the contact of an inhibitor described herein to the subject, that is, contact of a histone methyltransferase inhibitor, or together with at least a second inhibitor selected from the group consisting of an inhibitor of a histone demethylase, a HDAC inhibitor, a bromodomain (BRD) inhibitor, or BRaf (B-Raf) inhibitor to the subject.

In one embodiment, as used herein, the term "treat' or treatment" refers to reducing or alleviating at least one adverse clinical symptom associated with cancer, e.g., pain, swelling, low blood count etc. In another embodiment, the term "treat' or treatment" refers to slowing or reversing the progression neoplastic uncontrolled cell multiplication, i.e. shrinking existing tumors and/or halting tumor growth. In another embodiment, the term "treat' or treatment" refers to inducing apoptosis in cancer or tumor cells in the subject. Other results from cancer treatment, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

As used herein, the term "cancer remission" or "remission" refers to a decrease in or disappearance of signs and symptoms of cancer. In partial remission, some, but not all, signs and symptoms of cancer have disappeared. In complete remission, all signs and symptoms of cancer have disappeared, although cancer still may be in the body. In one embodiment, with respect to a tumor, the tumor may have reduced in size (i.e. partial remission) or even completely disappear and is not detected (i.e., complete remission).

As used herein, the term "recurrence" in the context of cancer in a subject refers to reappearance of signs and symptoms of cancer in the subject after a period of cancer remission, partial or complete remission. The recurrence of cancer in a subject means a relapse of cancer in the subject. For example, with respect to a tumor that had previously disappeared completely, one or more tumors are now detected in the subject again.

As used herein, the term "aggressive cancer" refers to cancer cells that grow rapidly. Such cancer are often graded as Grade III or IV cancers where the cells are evaluated by a pathologist to be poor differentiated or undifferentiated.

As used herein, the term "poor differentiated or undifferentiated" in the context of an aggressive cancer and the pathology-based grading of the cancer refers to the differences observed between the cancer cells and its surrounding normal non-cancer cells in the biopsy tissue. Differentiation describes how much or how little tumor tissue looks like the normal tissue it came from. Well-differentiated cancer cells look more like normal cells and tend to grow and spread more slowly than poorly differentiated or undifferentiated cancer cells. Differentiation is used in tumor grading systems, which are different for each type of cancer.

As used herein, the term "small molecule" with reference to an inhibitor described herein refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In one embodiment, a small molecule inhibitor is a heterorganic compound or an organometallic compound. In another embodiment, the small molecule inhibitor is not more than than 900 Da molecular weight.

As used herein, the term "a therapeutically effective amount" and grammatical variations thereof, refers to an amount sufficient to achieve the intended purpose of treating cancer. In one embodiment, a therapeutically effective amount of a histone methyltransferase inhibitor, an inhibitor of a hi stone demethylase, a HDAC inhibitor, a bromodomain inhibitor, or BRaf (B-Raf) inhibitor or a composition described herein for a method of treating cancer is an amount of sufficient to induce apoptosis of cancer cells of the subject as compared to in the absent of the inhibitor or a composition respectively. The term "therapeutic effect" is used herein in a broad sense and includes prophylactic effects. In other embodiments, the amount that is safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of an inhibitor or a composition described herein can inhibits tumor further growth, cause a reduction in size or even completely halt tumor growth, shrink the sizes of tumor, even complete regression of tumor, and reduce clinical symptoms associated with tumor. An effective amount for treating cancer is an amount of an inhibitor or a composition described herein sufficient to result in a reduction or complete removal of the symptoms of the disorder, disease, or medical condition. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount". However, for any given case, an appropriate "effective amount" can be determined by a skilled artisan according to established methods in the art using only routine experimentation.

As used herein, the term "mutation" with respect to a gene refers to a change of the nucleotide sequence of the gene of an organism. In some embodiments, the "mutations" referred to herein can take the form of one or more nucleotides deletions, one or more nucleotides additions, or one or more nucleotides substitutions. In some embodiments, the "mutations" referred to herein have the effects of one or more amino acids deletions, one or more amino acids additions, or one or more amino acids substitutions when the mutated gene is transcribed and translated into a polypeptide.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human. In one embodiment, the subject is a non-primate.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's "The Science and Practice of Pharmacy", 22nd Ed., Allen, Loyd V., Jr, ed. (Pharmaceutical Press, 2012, ISBN 978 0857110626). The formulation should suit the mode of administration.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

ARID2-knockdown of two different melanoma lines renders the cells sensitive to two different G9a inhibitors, UNC0638 and BIX-01294.

Figure 4A:
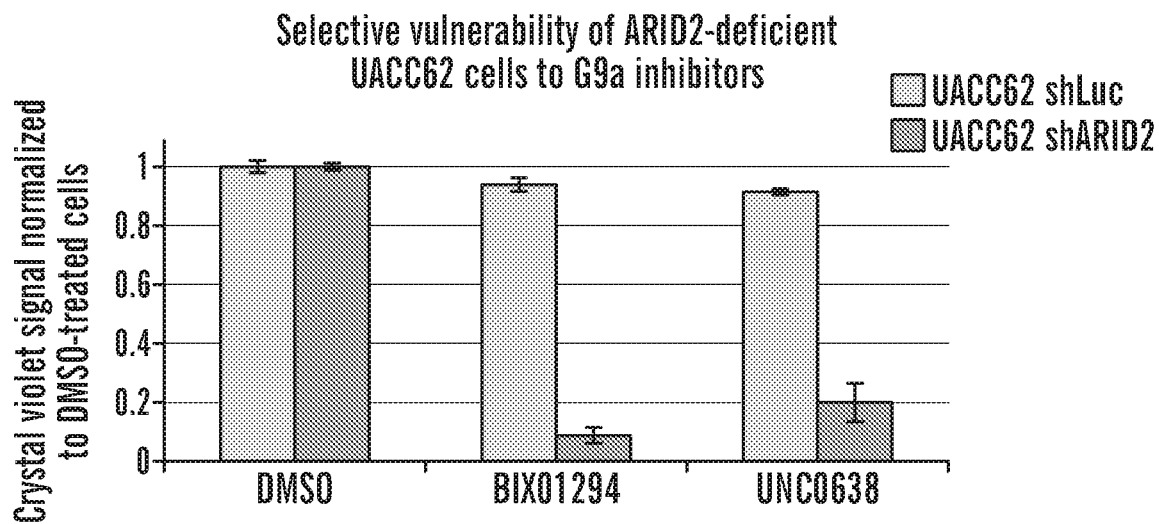
Figure 4B:
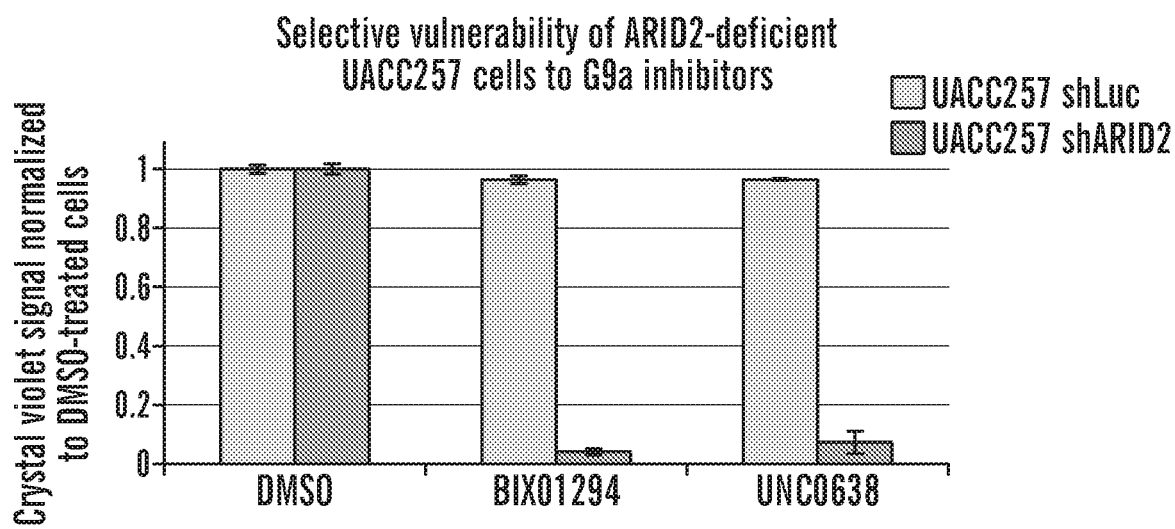

FIGS. 4A and 4B show the selective vulnerability of ARID2-deficient melanomas UACC62 cells to G9a inhibitors, BIX01294 and UNC0638. Quantification of cell number using crystal violet staining reveals selective vulnerability of ARID2-deficient cells to two different G9a inhibitors, UNC0638 and BIX-01294.

Figures 5A, 5B:
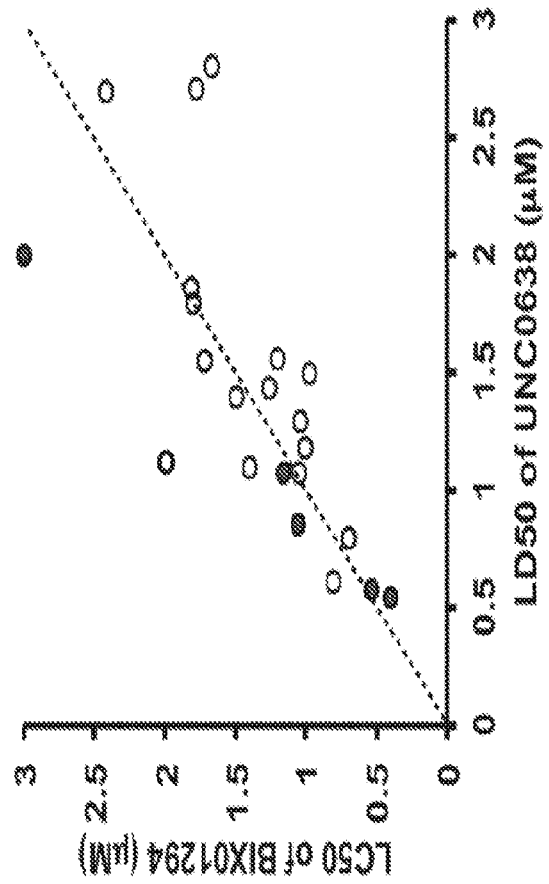

FIG. 5A shows the graphical representation that ARID2 mutation predicts the sensitivity to G9a inhibitors, BIX01294 and UNC0638, (data from 22 cell lines). LD50 value of each melanoma cell line plotted for the two G9a inhibitors UNC0638 and BIX-01294. (n=22). ARID2 mutant cell lines indicated in closed circles.

FIG. 5B shows the P-value of statistical correlation between gene mutational status and G9a inhibitor sensitivity (Fisher's exact test).

Figure 6A:
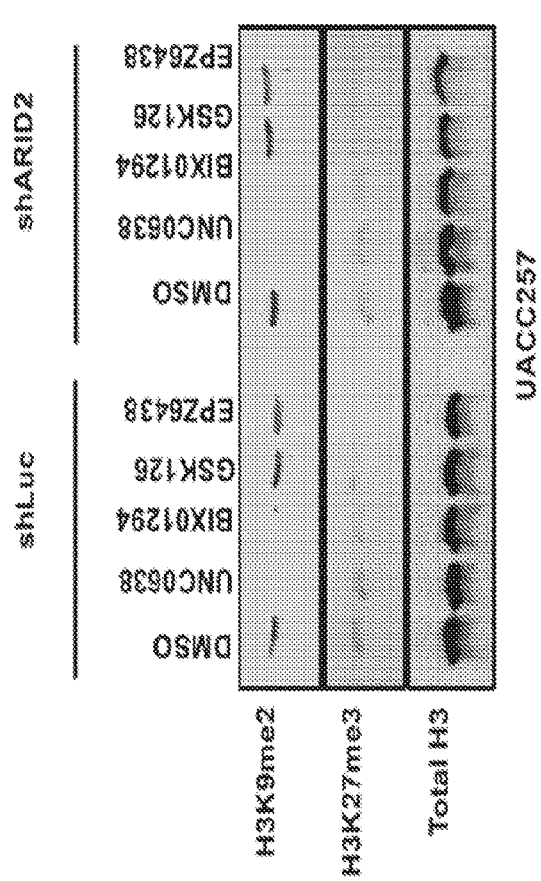
Figure 6B:
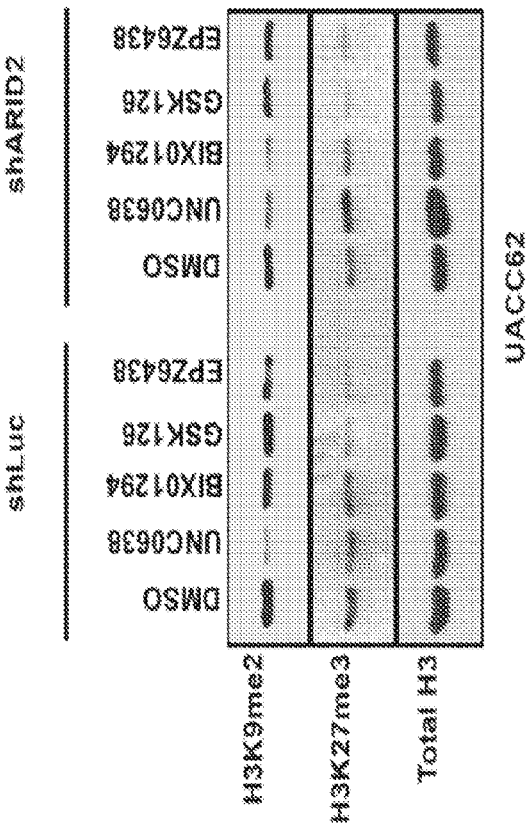

FIGS. 6A and 6B show that G9a and EZH2 act independently to confer synthetic lethal effects. The G9a and EZH2 methyltransferases are known to target H3K9 and H3K27, respectively. Shown are the histone western blot analyses of cells treated with G9a inhibitors (UNC0638 and BIX-01294) or EZH2 inhibitors (GSK126 and EPZ6438). There is selective and specific decrease in the methylation marks at the different residues, supporting independent mechanisms of the two drug targets. G9a acts specifically at the H3K9 residue in a manner distinct from the H3K27 methyltransferase EZH2 in UACC257 cell line.

Figure 7:
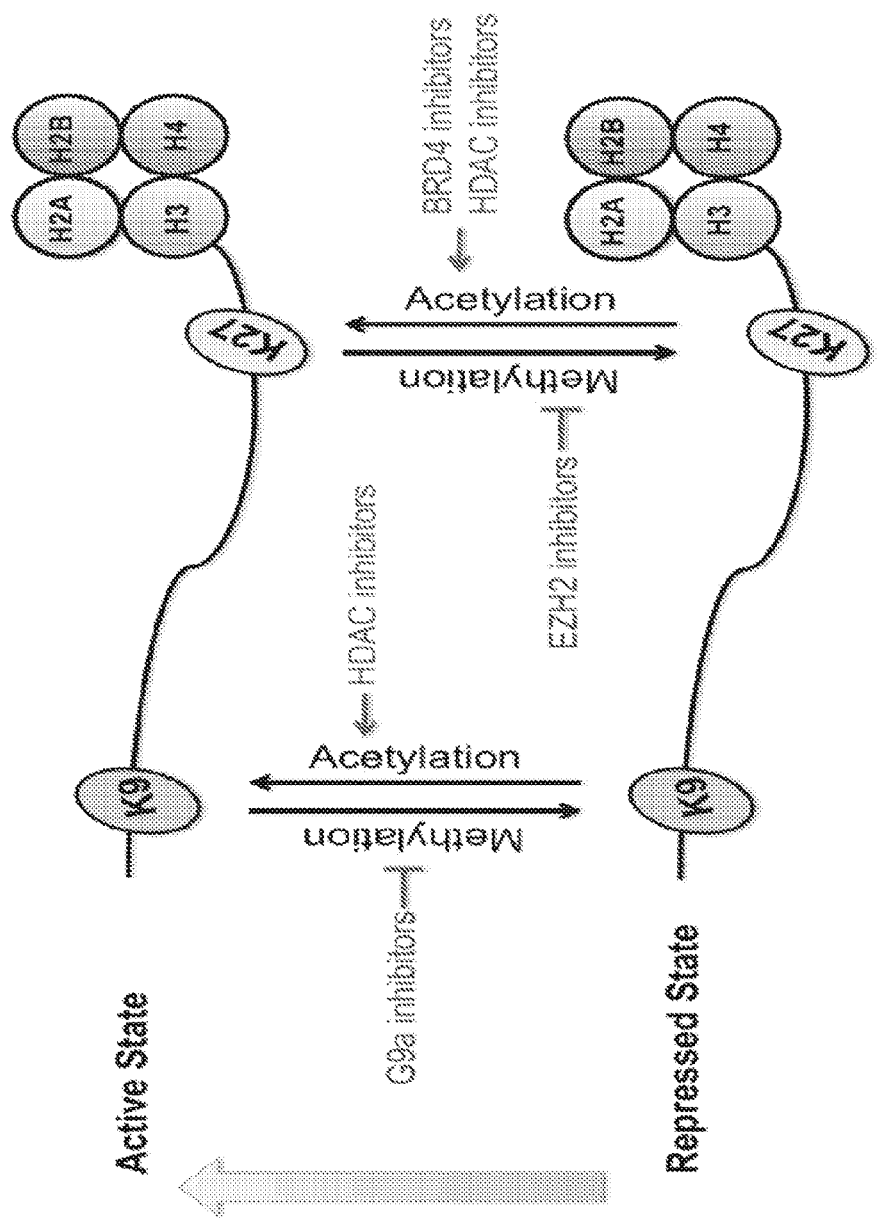

FIG. 7 is a schematic representation of an embodiment where complementary effects of candidate inhibitors promote an active state of the chromatin.

Figure 8:
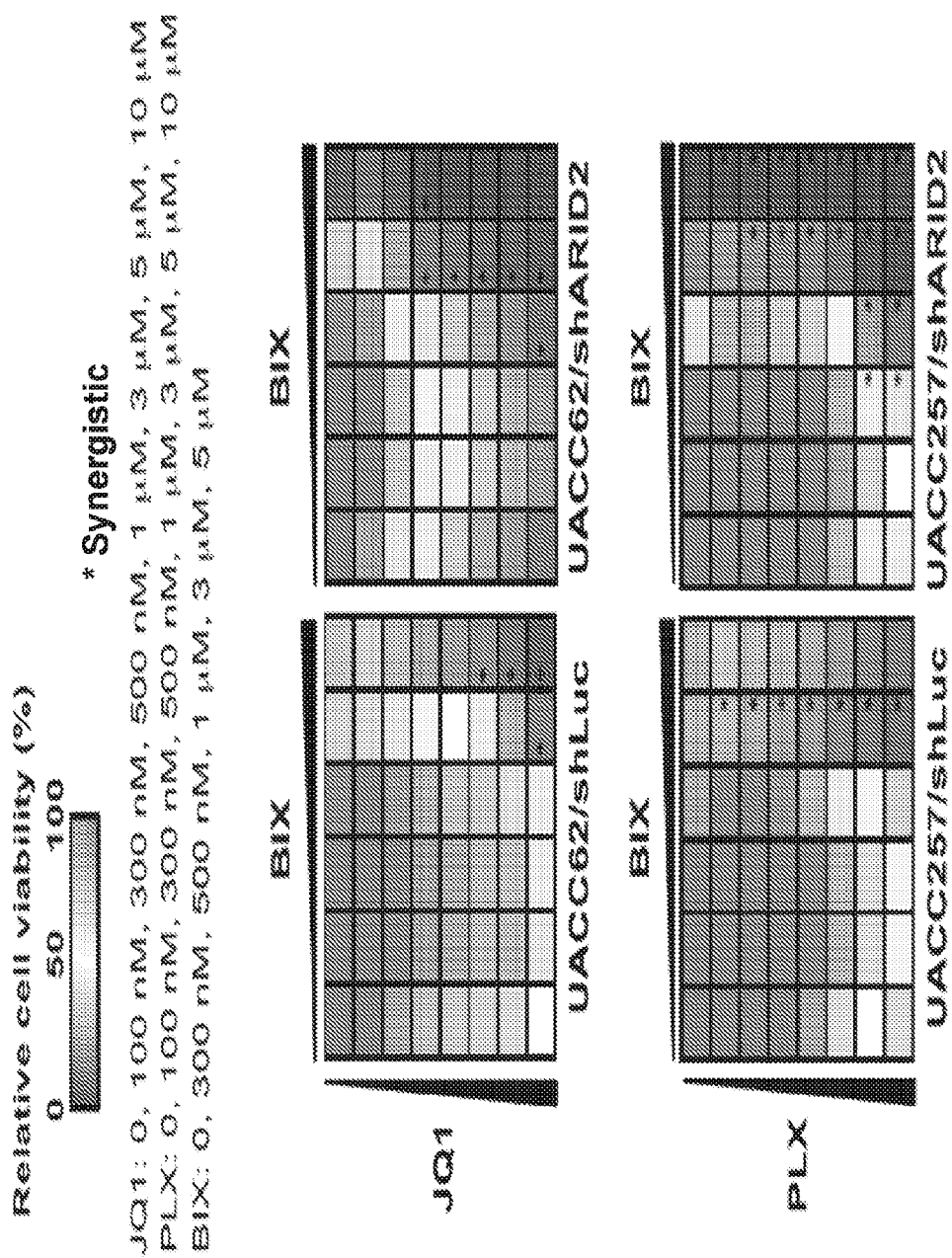

FIG. 8 summarizes the combination therapy on isogenically matched engineered ARID-deficient melanoma cell lines. Heatmaps showing cell viability after treatment with the G9a inhibitor BIX-01294 in combination with other small molecule inhibitors (bromodomain inhibitor JQ1 and BRAF inhibitor PLX). Drug synergy is selectively enhanced in ARID2-deficient cell lines.

Figure 9:
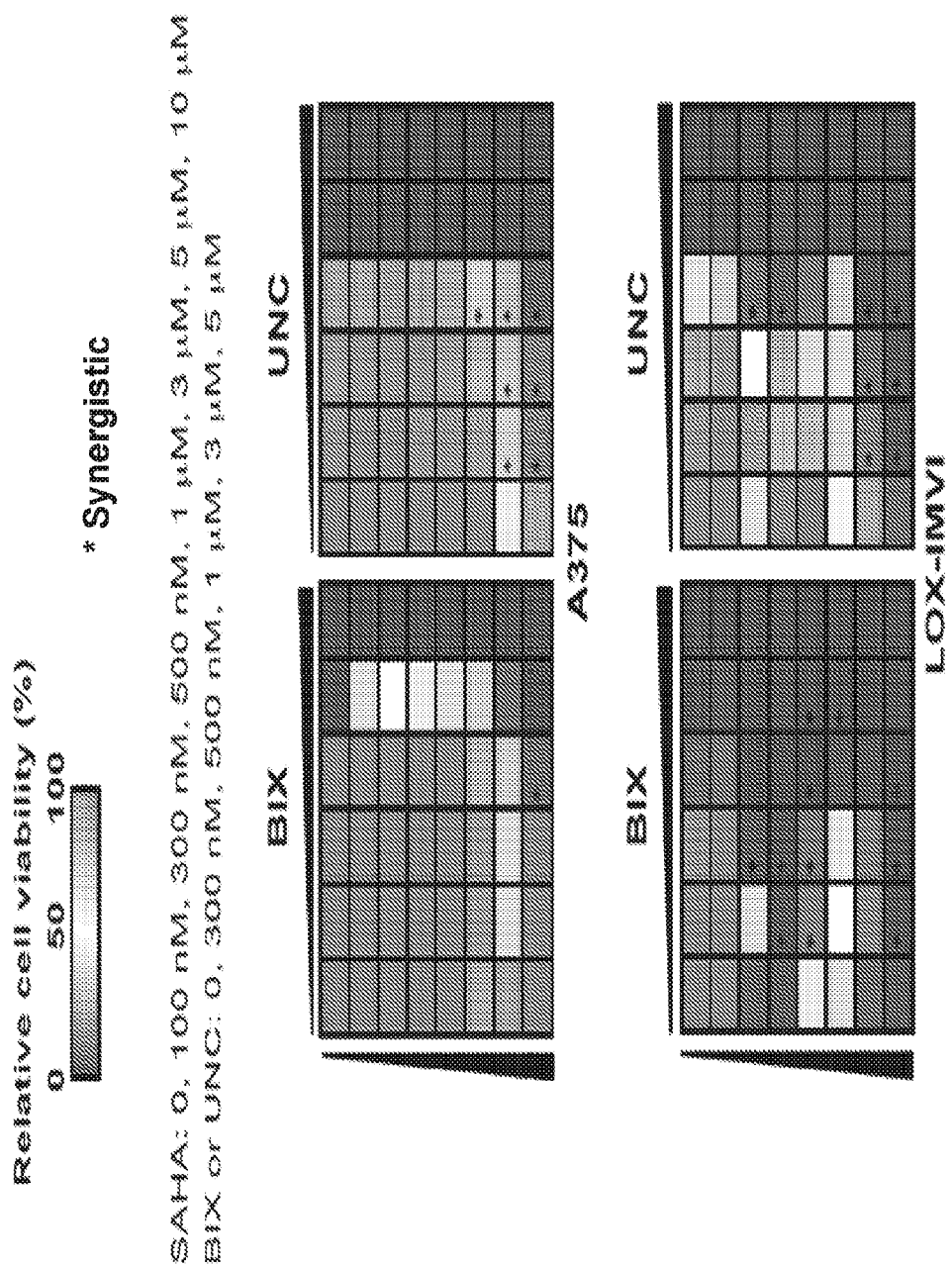

FIG. 9 summarizes the combination therapy on endogenous ARID-deficient melanoma cell lines. Heatmaps showing cell viability after treatment with G9a inhibitor (UNC0638 or BIX-01294) in combination with the HDAC inhibitor SAHA (vorinostat). Drug synergy is selectively enhanced in the ARID-deficient LOX-IMVI cell line compared to the ARID wildtype A375 cell line.

Figure 11:
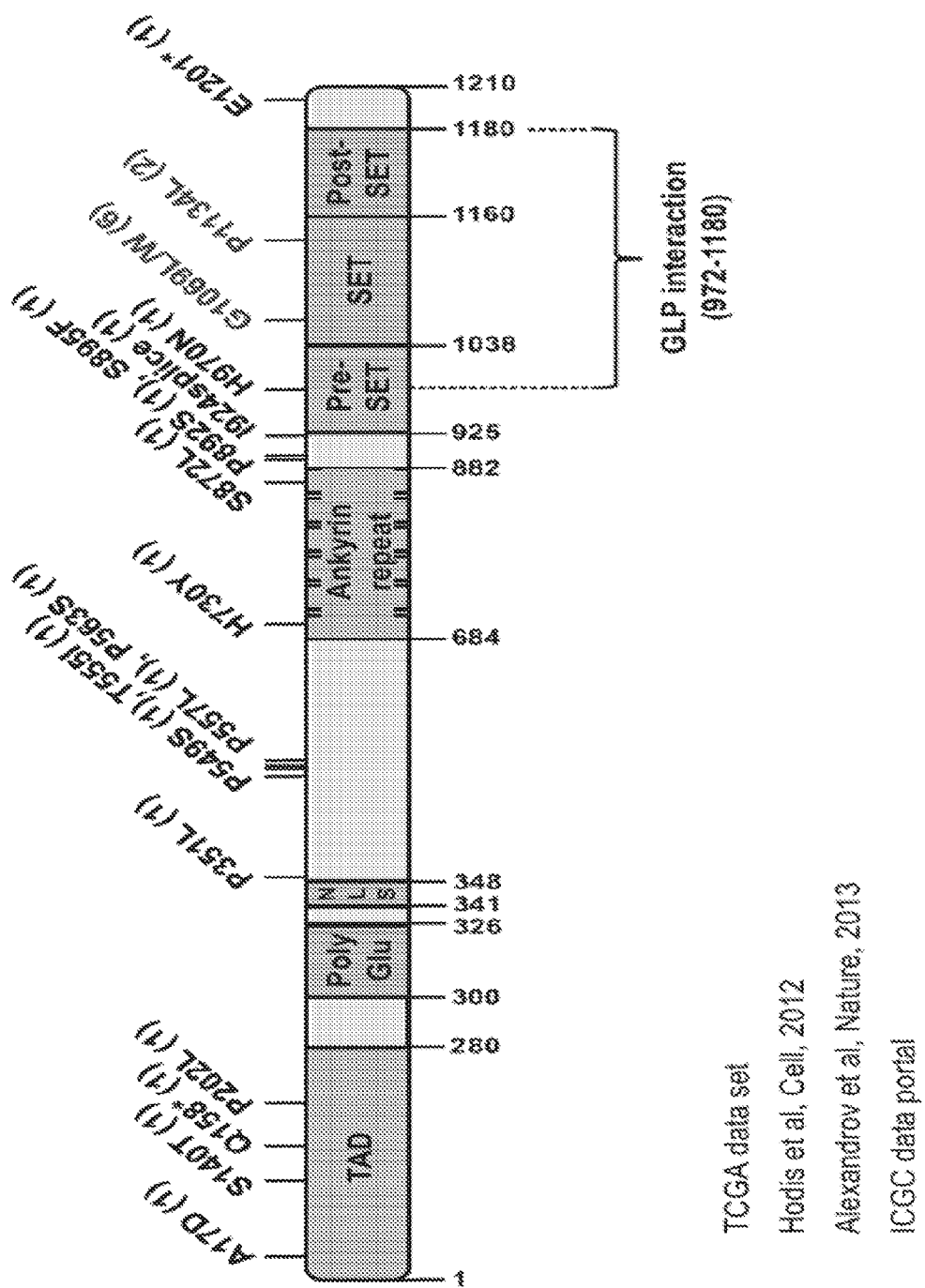

FIG. 10 shows the possible combination therapies with existing drugs targeting chromatins. Many of the drug candidates from the synthetic lethality screen offer opportunities for combination therapy with existing drugs and immunotherapy. Epigenetic inhibitors targeting HDAC and small molecule inhibitors targeting BRAF are currently used in the clinic and have shown promise in combination treatment with G9a inhibitors FIG. 11 shows the G9a/EHMT2 non-synonymous mutational landscape from data collected in The Cancer Genome Atlas (TCGA), Hodis et al, Cell, 2012, 150(2):251-63, "A landscape of driver mutations in melanoma." Cell. 2012; Alexandrov et al, Nature, 2013, 500(7463):415-21, "Signatures of mutational processes in human cancer.", International Cancer Genome Consortium (ICGC) data portal. Analysis of cancer mutational data shows a recurring mutation within the G9a SET catalytic domain. Activating mutations within this domain are already known to be present in EZH2, another target identified in the synthetic lethality screen.

Figure 12:
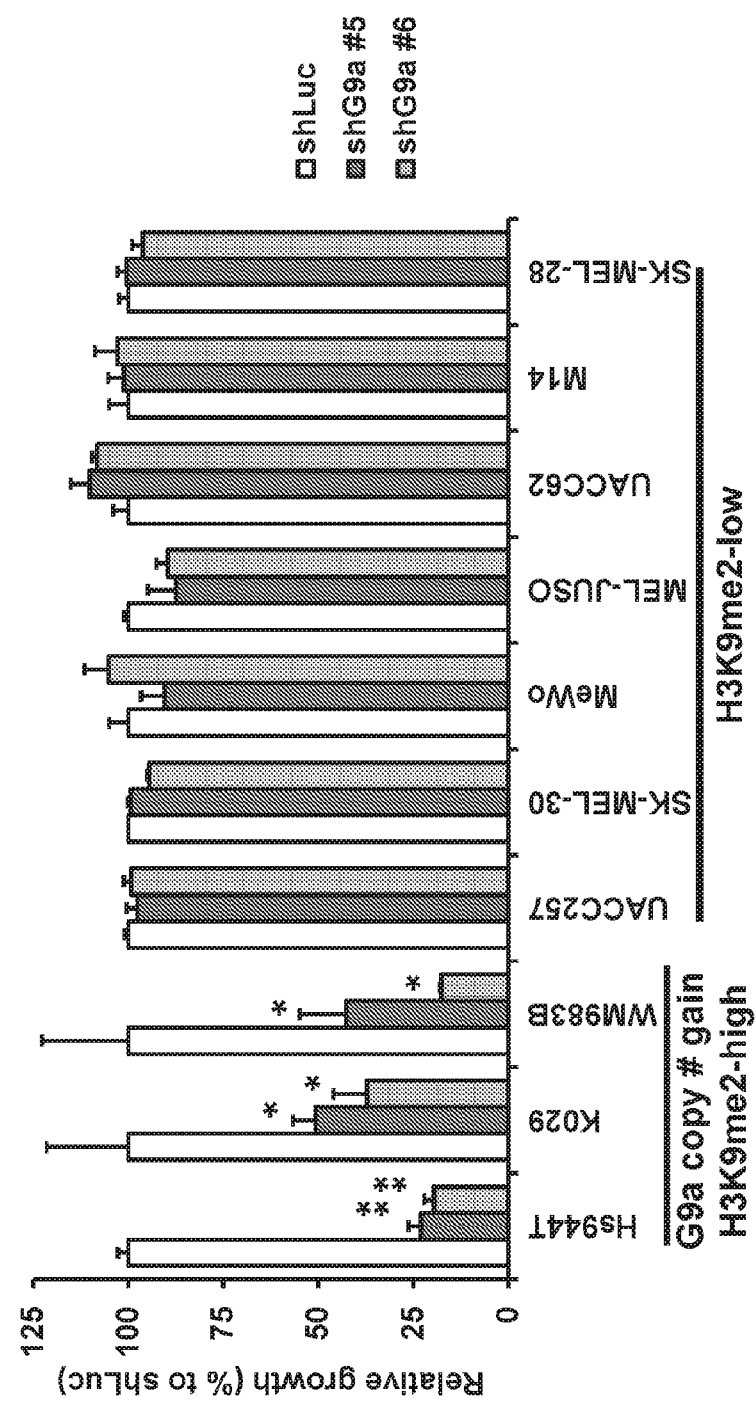

FIG. 12 shows that G9a-amplified melanoma cells are addicted to G9a. Colony formation assay of melanoma cell lines that were infected with indicated shRNAs. After 1 week culture, cells were fixed with 4% paraformaldehyde and stained with 0.05% crystal violet. Cell growth were calculated using crystal violet absorbance at 590 nm wave length.

Figure 13A:
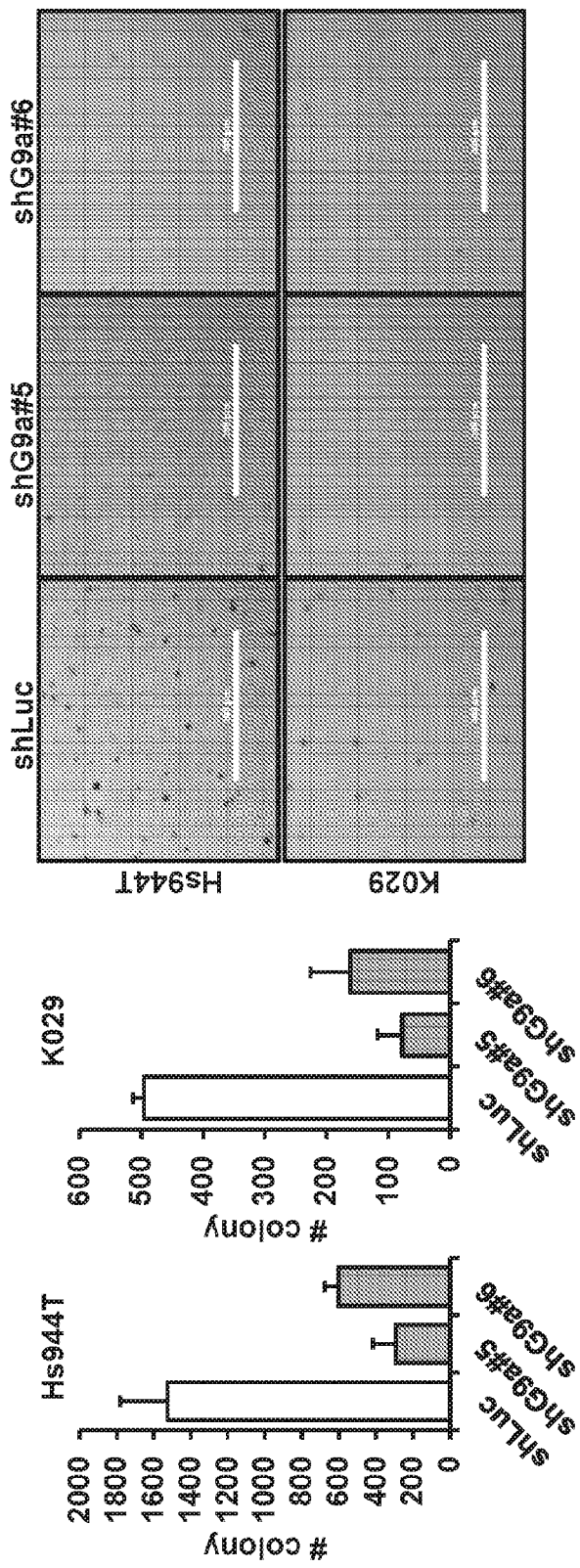
Figure 13B:

FIGS. 13A and 13B shows G9a is required for tumorigenic potential of G9a-amplified melanoma show G9a-amplified melanoma cell lines. Cell lines Hs944T and K029 were infected with indicated hairpins and subsequently cultured with puromyciin for 72 hours. (FIG. 13A) Soft agar assay after 1 month of puromycin selection. Colony number was determined by Cellprofiler. (FIG. 13B) shows G9a knock down efficiency via western blotting.

FIGS. 14A and 14B show melanoma cell and melanocyte are sensitive to G9a inhibitors. Indicated cell types were treated with varying amounts of (FIG. 14A) UNC0638 or (FIG. 14B) BIX01294 and viability was measured by celltiter Glo assay.

FIG. 15 shows IC50 values of G9a inhibitors, UNC0638 and BIX01294, when utilized to treat melanoma and melanocytes.

Figure 16:
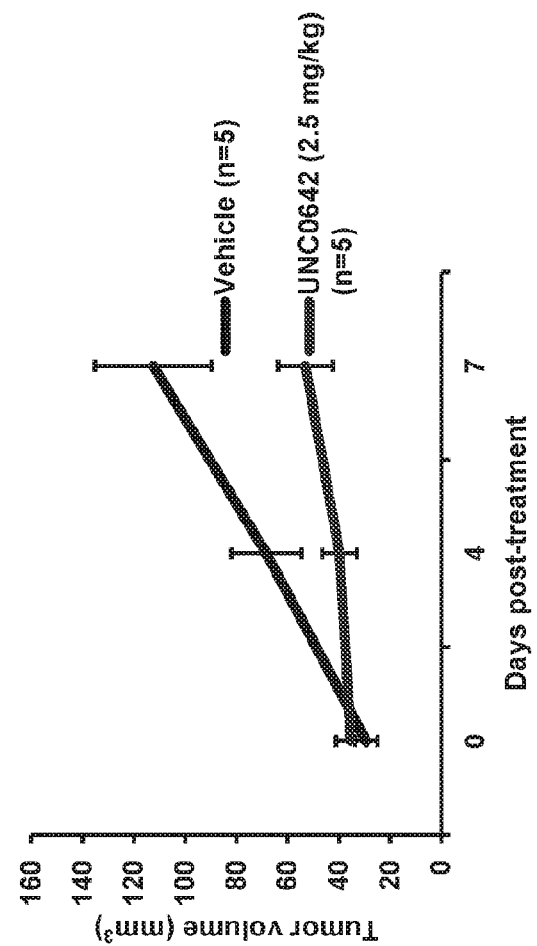

FIG. 16 shows that potent in vivo G9a inhibitor, UNC0642, effectively suppress tumor growth of G9a-amplified melanoma cells in vivo. G9a-amplified melanoma cell line, K029, was subcutaneously inoculated on SCID mice (5×106 cells/100 ml PBS). Vehicle (10% DMSO/PBS) or UNC0642 (2.5 mg/kg) was daily administrated by ip injection 8 days after K029 inoculation.

Figure 17:
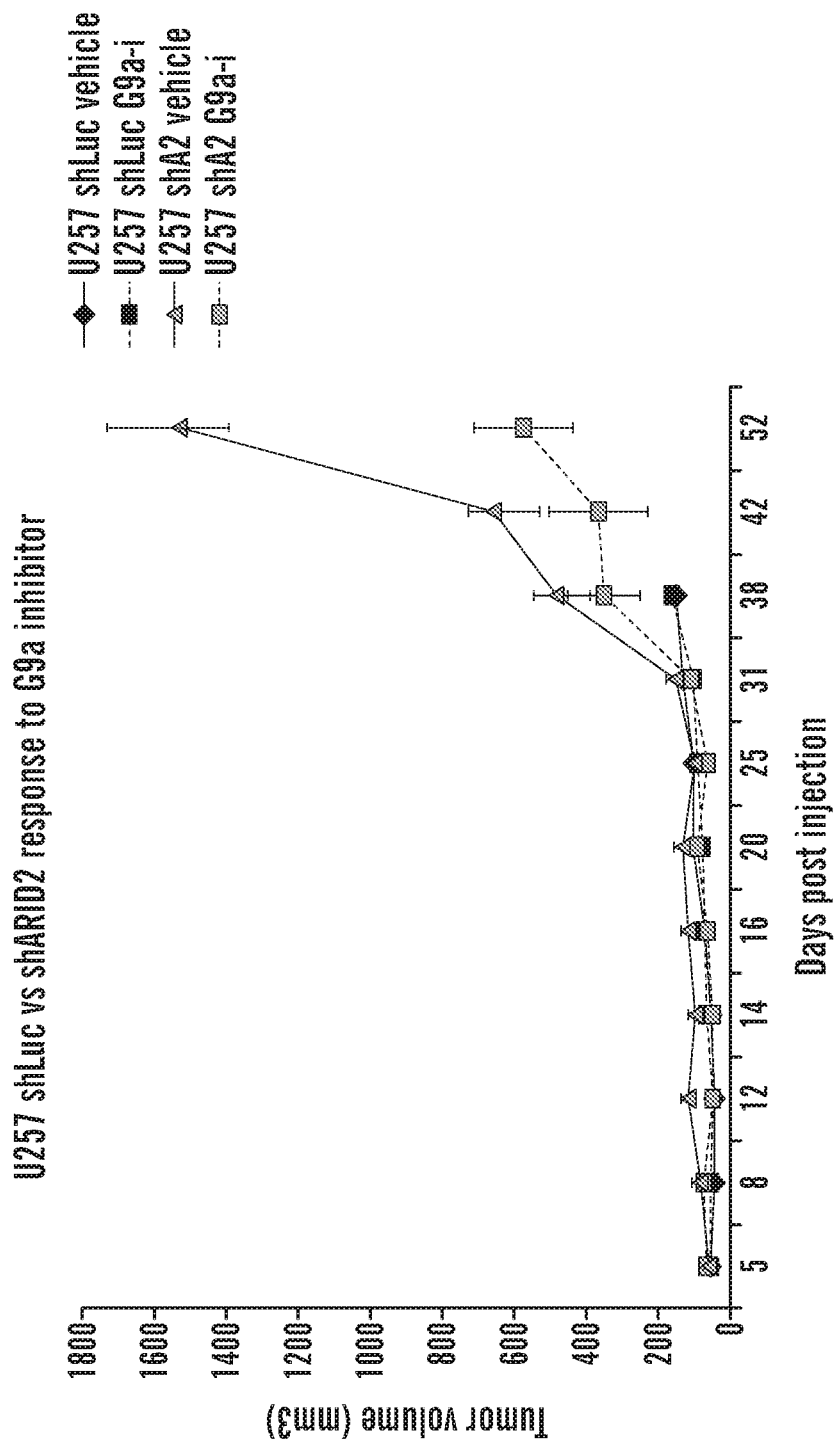

FIG. 17. shows knockdown of the ARID2 gene (shArid2) sensitizes the U257 melanoma cell line to treatment by a G9a inhibitor within an in vivo animal xenograft tumor model. Depletion of ARID vis shRNA results in a drastic increase in tumore volume. Treatment of ARID shRNA cells with G9a inhibitor significantly reduces tumor formation.

Figure 18:
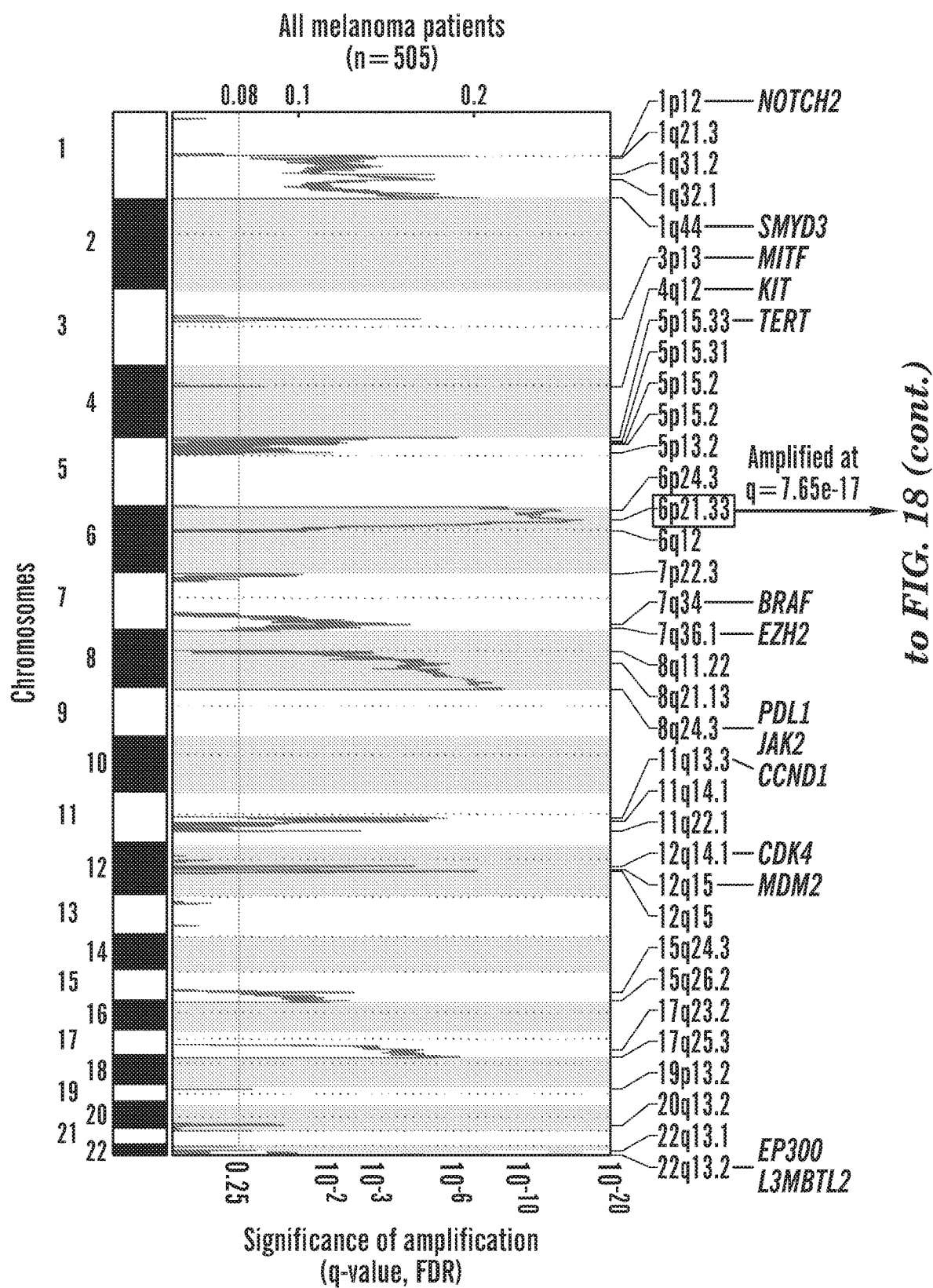
Figure 18:
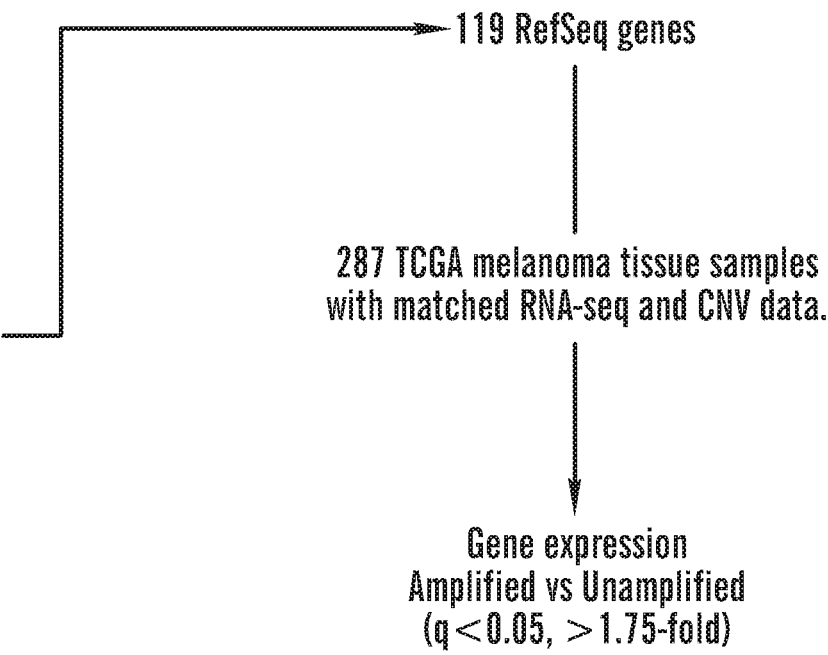

FIG. 18 shows that 6p21 locus (which includes G9a) is focally amplified in TCGA melanoma. Copy number alteration was examined in melanoma patients by GISTIC analysis. The 6p21 locus, which encompassing G9a, was found to be significantly and focally amplified. Furthermore, among 119 amplicons in this locus, only four genes, CCHCR1, G9a, ZBTB12, RNF5, are significantly upregulated in 6p21-amplified melanoma patients as compared to unamplified patients. Thus, 6p21 amplification meaningfully affects these gene expressions.

FIG. 19 shows a chart comparing tumors with 6p21-p23 gain or amplification. 6p21 copy number amplification and gain have already been reported in several tumor malignancies, and correlates with poorer prognosis in melanoma. 6p21 locus is focally amplified in TCGA melanoma. Adapted from Santos, et al. (2006) *J. Clin. Pathol.*

Figure 20:
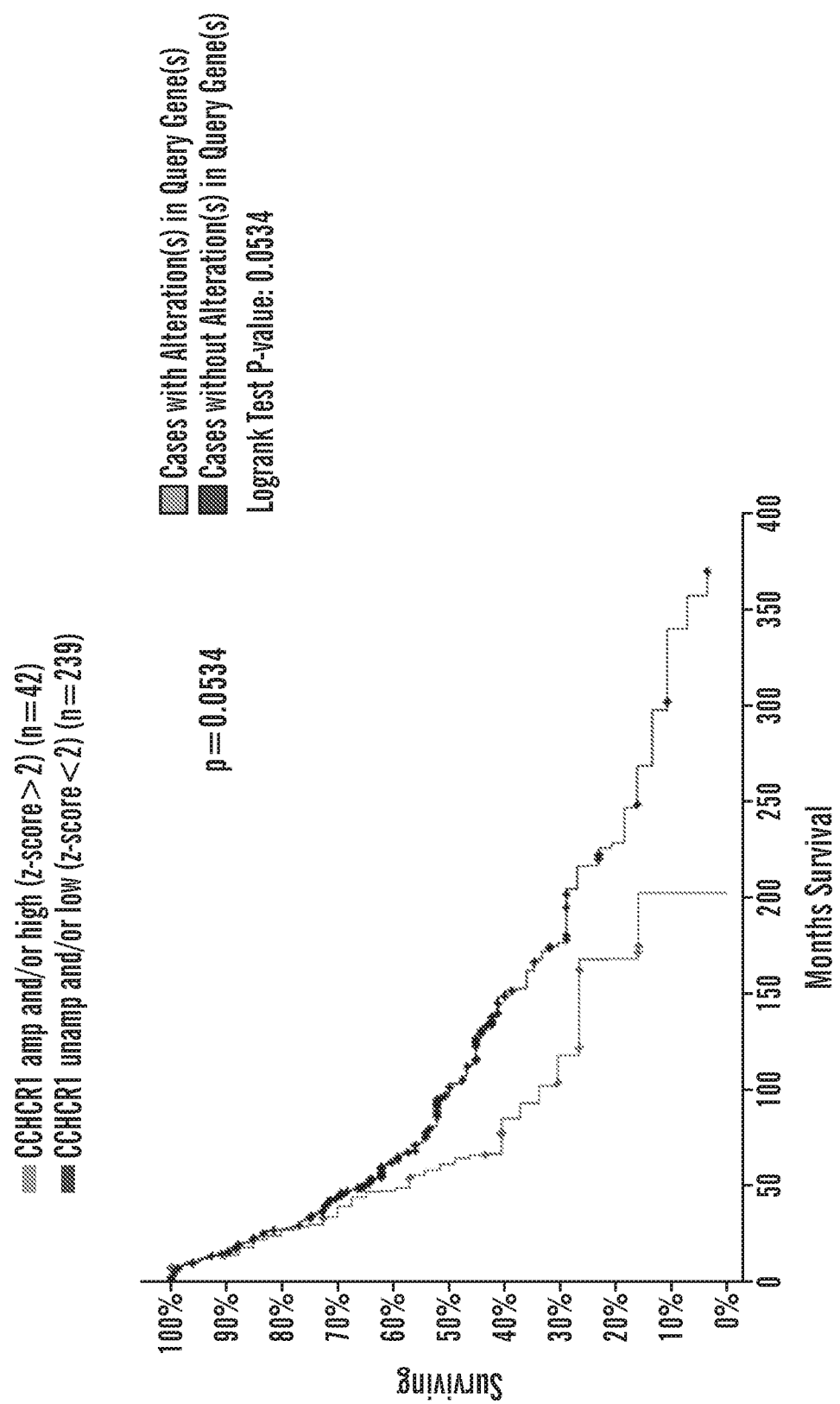
Figure 20:
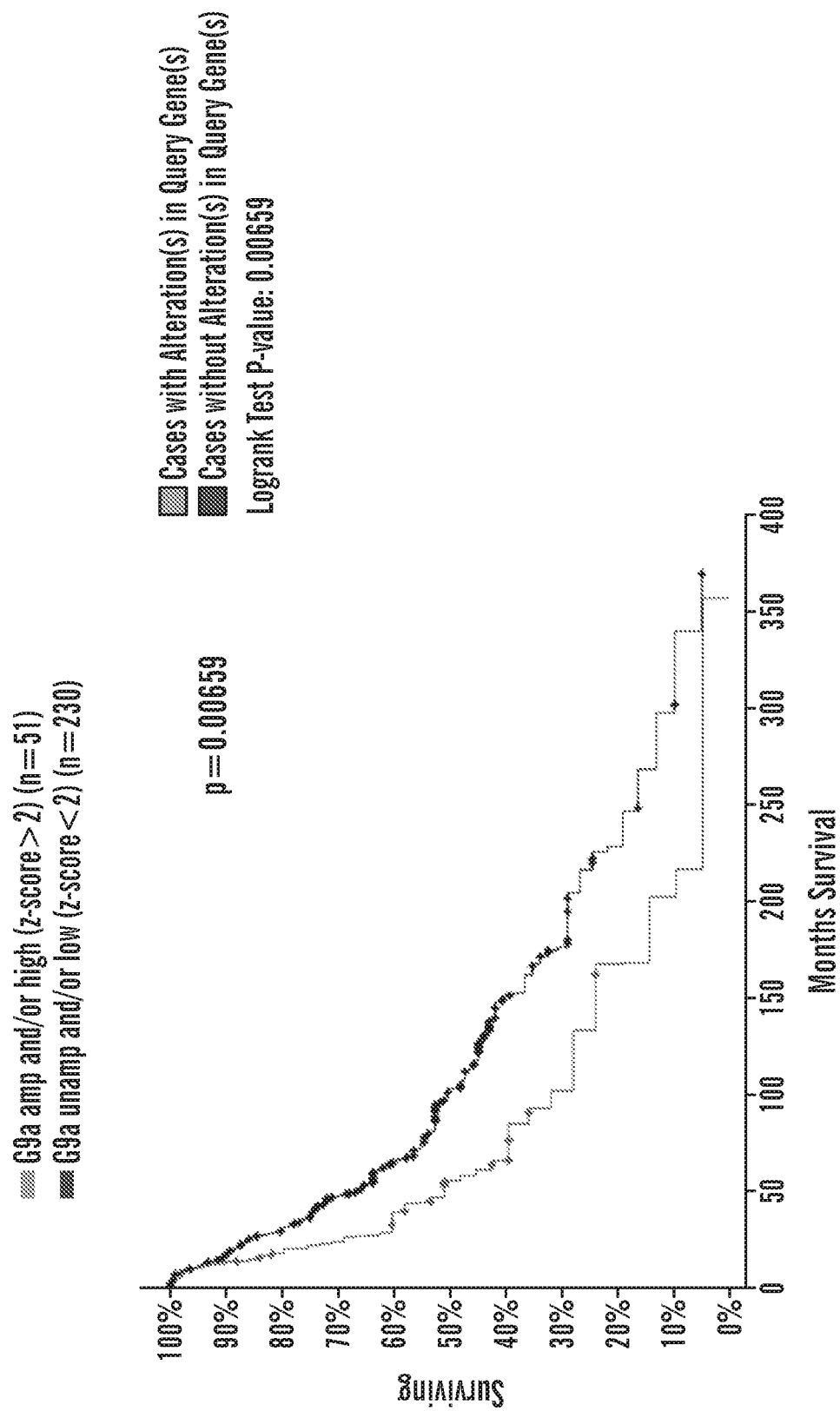
Figure 20:
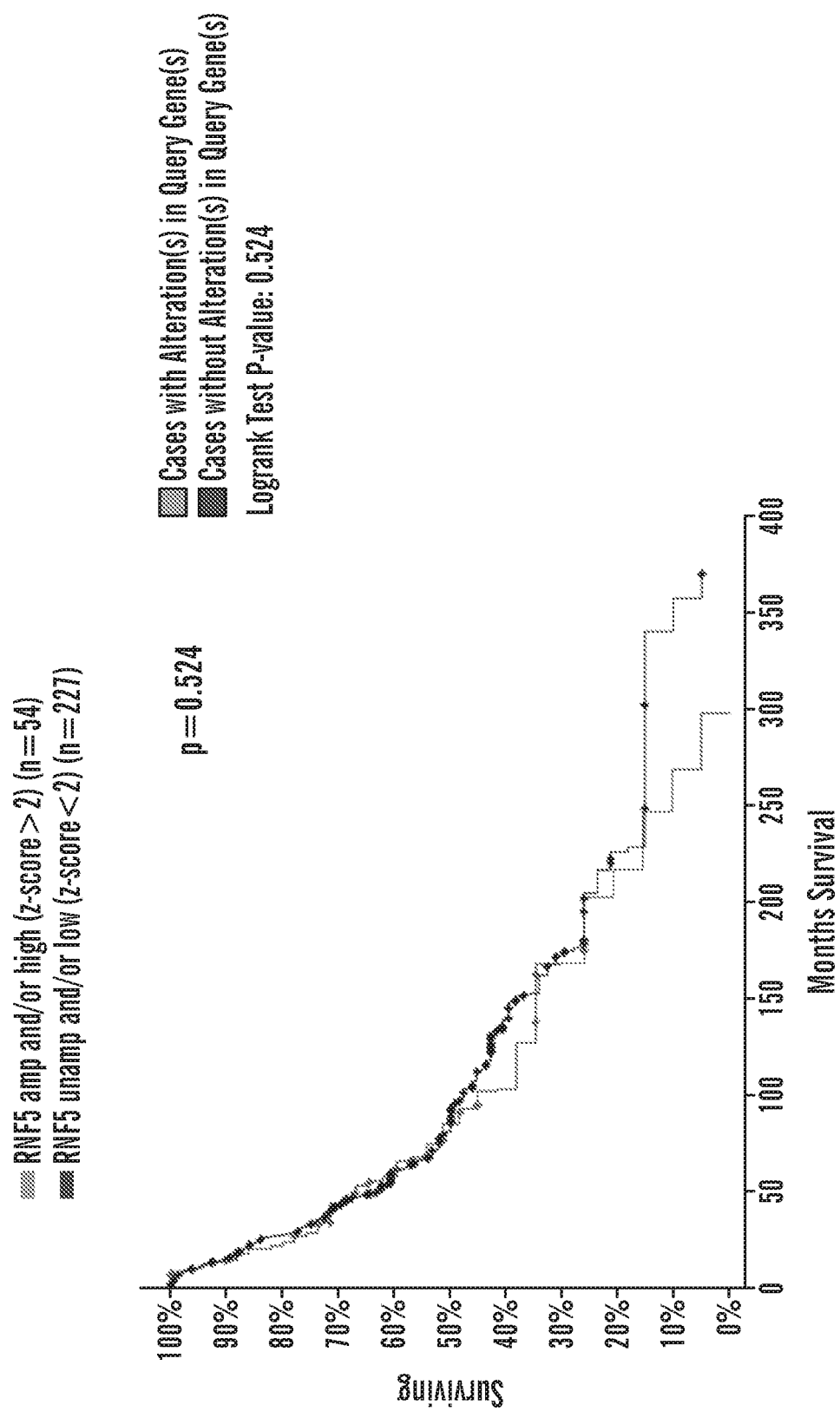
Figure 20:
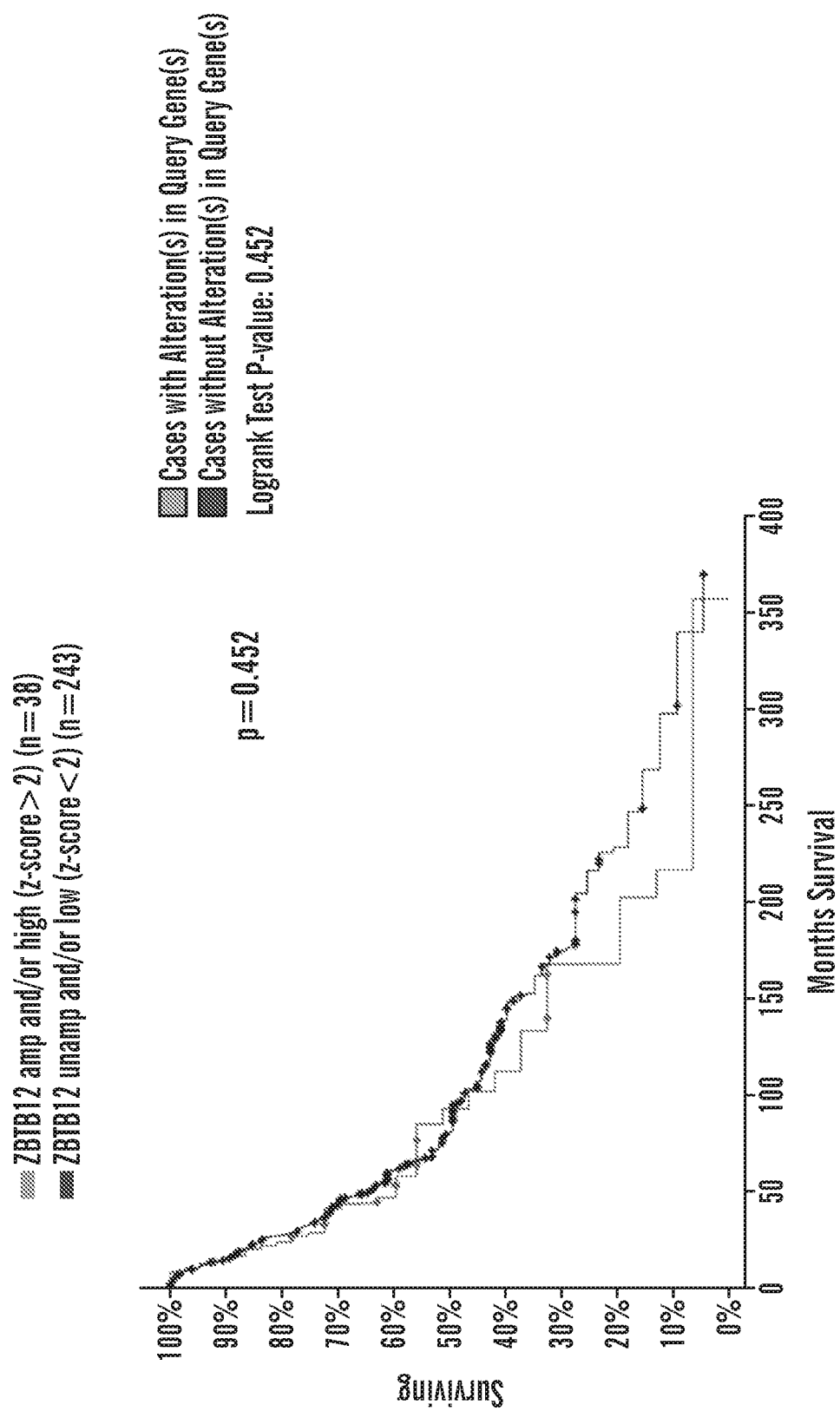

FIG. 20 show the comparison of survival rates (in months) for TCGA melanoma compared to TCGA melanoma with the indicated gene amplification in the 6p21-p23 amplicon. Only an amplification in the G9a gene correlated with the poor prognosis of TCGA melanoma. Amplification of other genes within the amplification, CCHCR1, RNF5, and ZBTB12, did not significantly correlate with the poor prognosis of TCGA melanoma.

Figure 21:
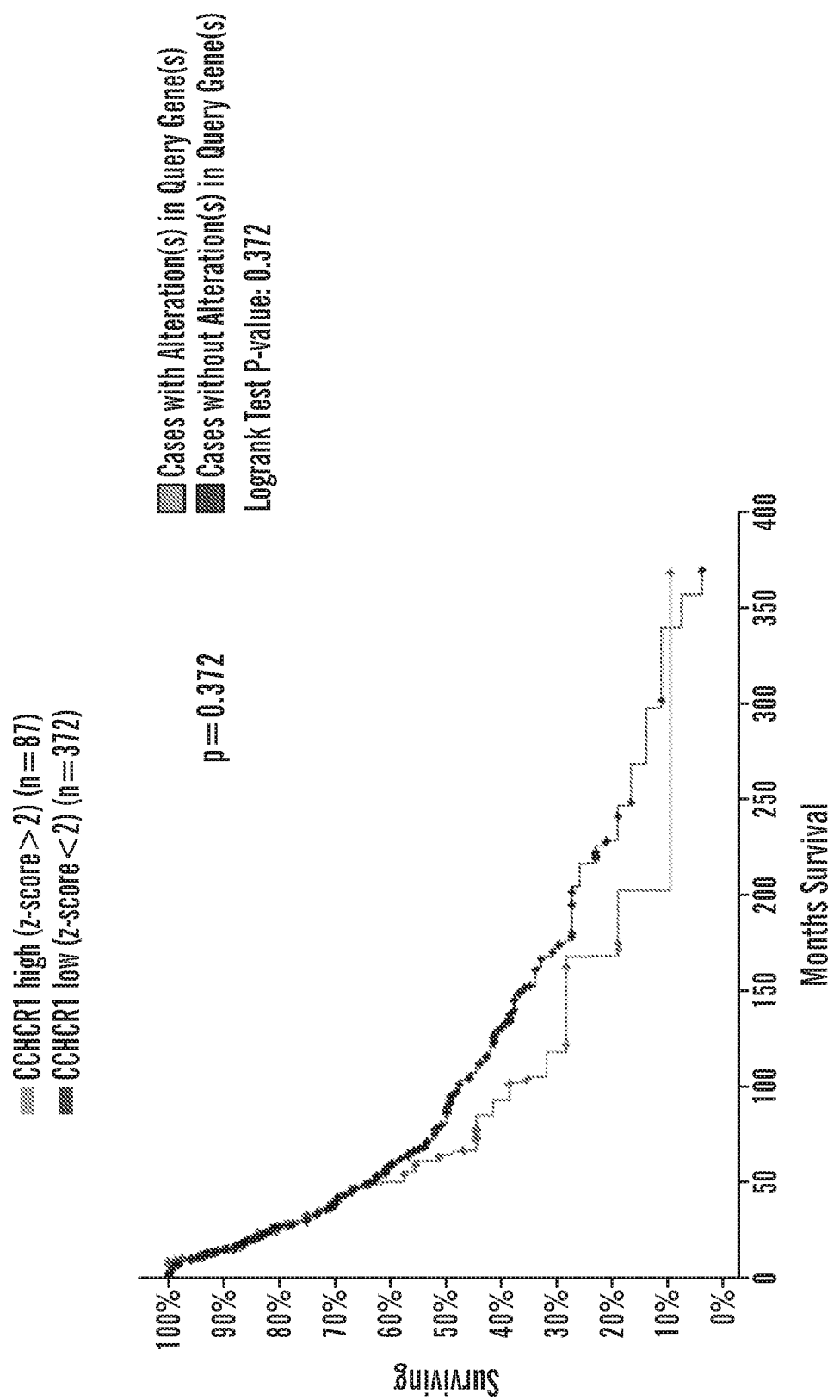
Figure 21:
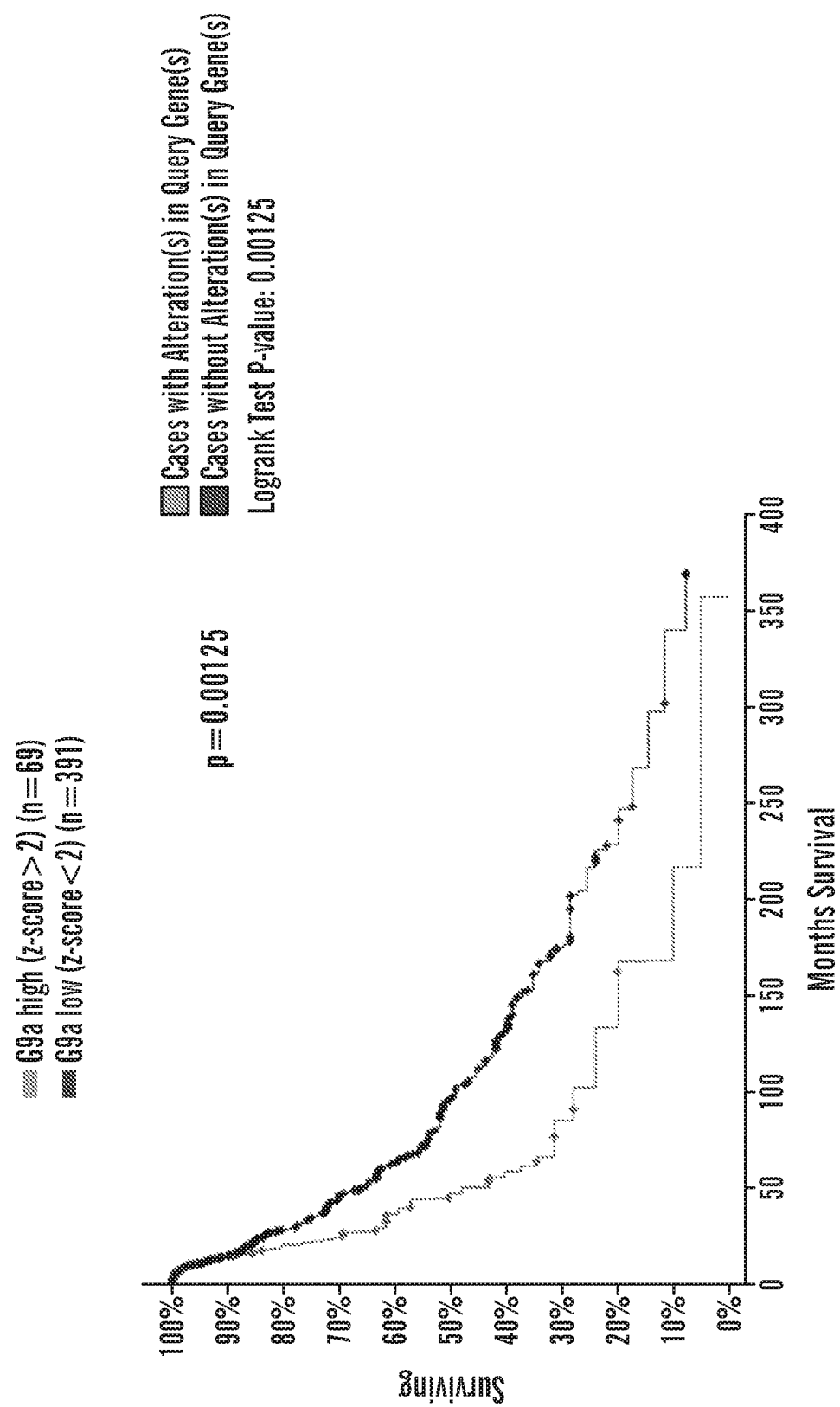
Figure 21:
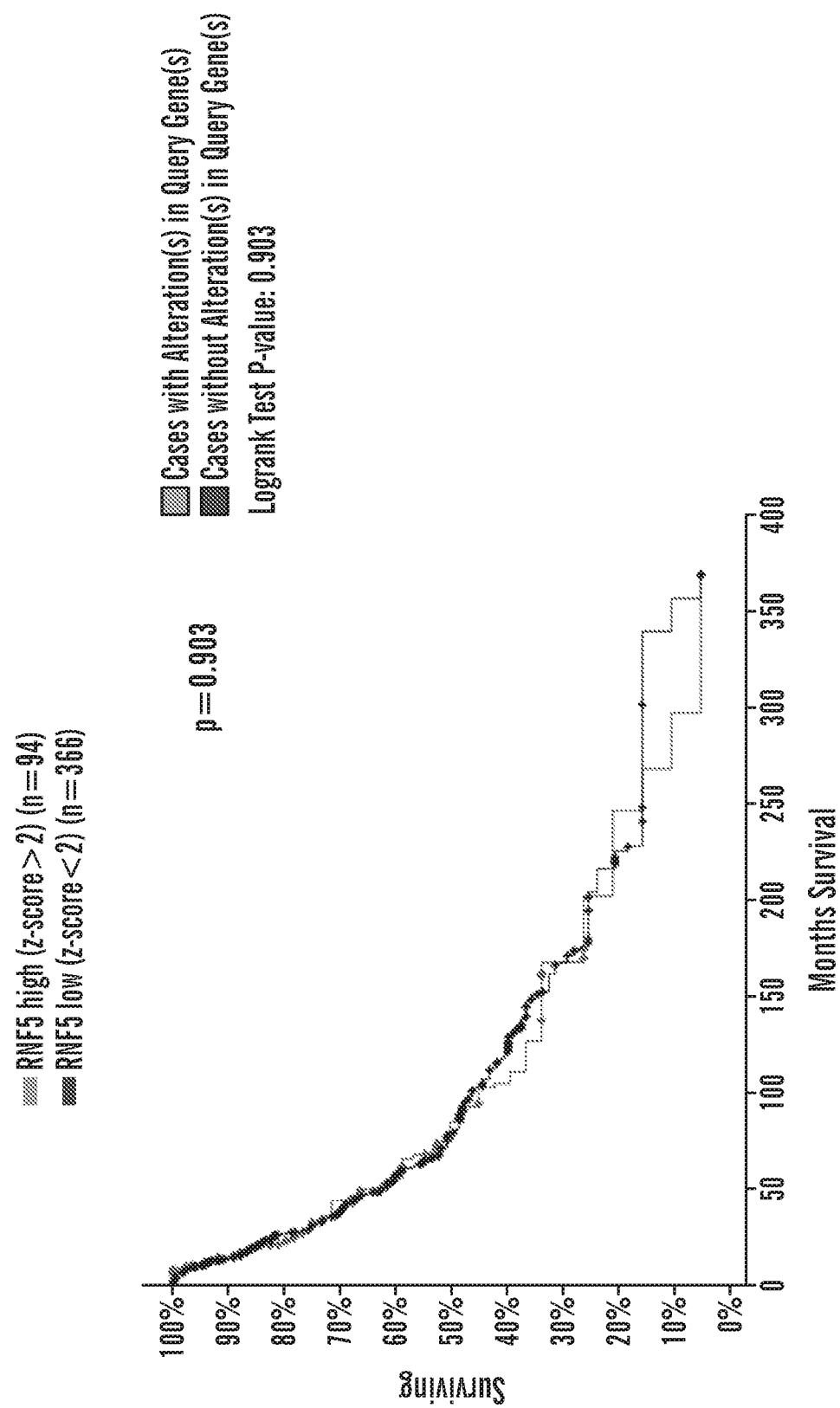
Figure 21:
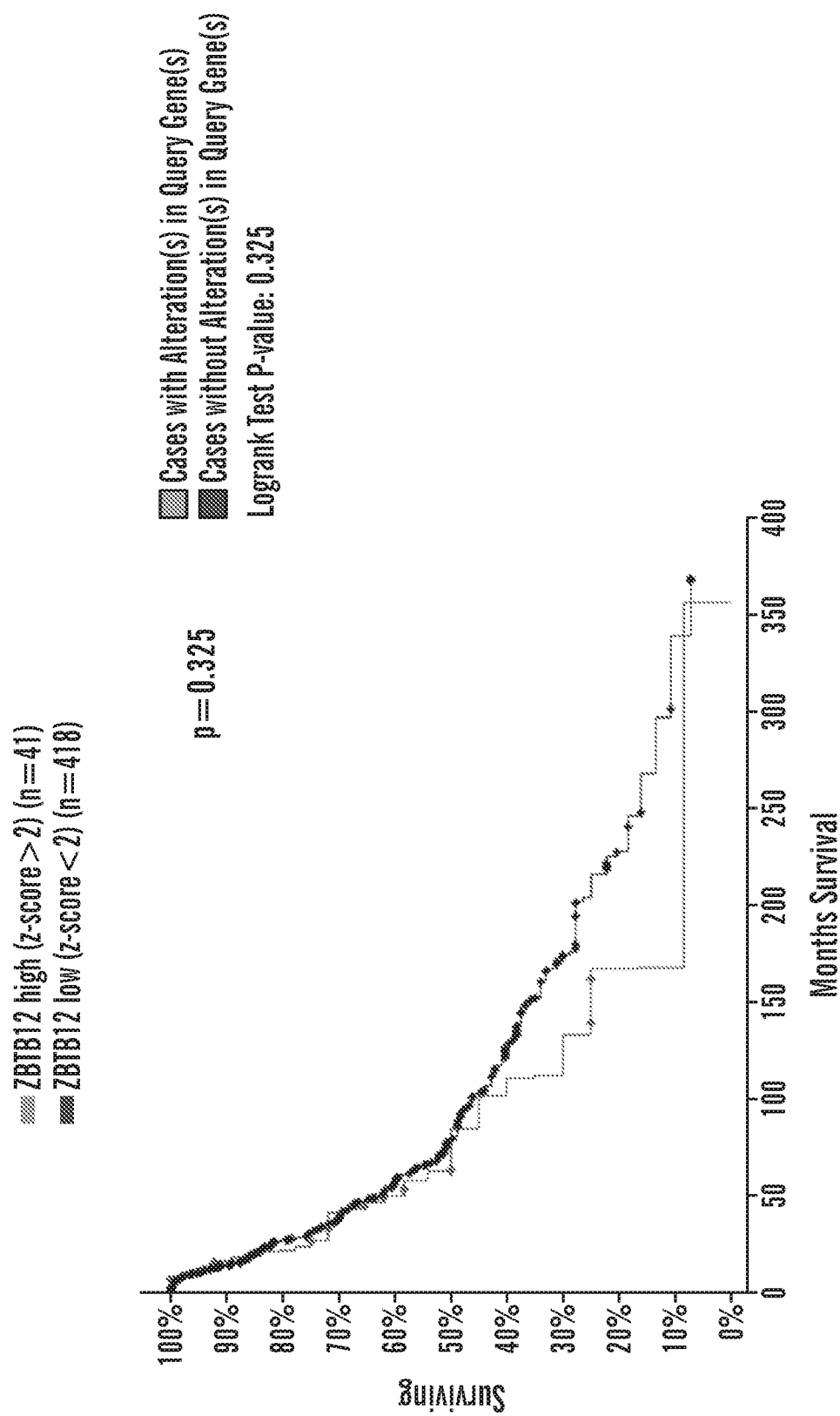

FIG. 21 shows that comparison of survival rates (in months) for TCGA melanoma with the indicated levels of a gene in the 6p21-p23 amplicon. Amplification of G9a significantly correlates with a poorer prognosis in TCGA melanoma compared to amplification of other genes within the amplification, CCHCR1, RNF5, and ZBTB12.

Figure 22:
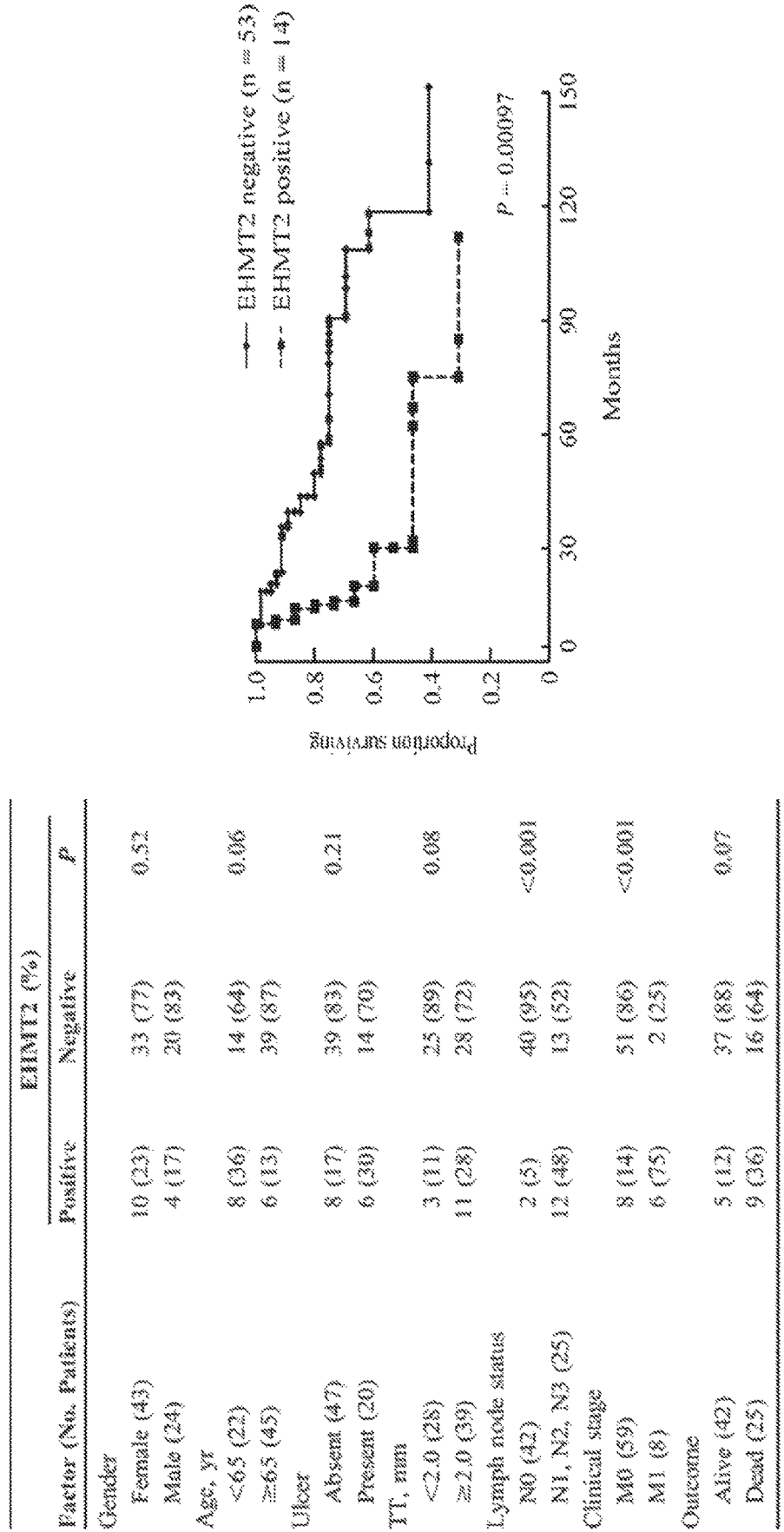

FIG. 22 shows that amplification of the EHMT2 gene, also known as G9a, correlates with a poor prognosis for melanoma patients.

FIGS. 23A-23C show that G9a expression is required for melanoma survival and growth. Depletion of G9a significantly inhibits growth and survival of the melanoma cell line with 6p21 amplification. FIG. 23A shows the growth of Hs944T cells in culture with the indicated gene depletion via shRNA hairpin expression. FIG. 23B shows the cell growth relative to the control shRNA (shLuc). FIG. 23C shows western blots probed with indicated antibody confirming the efficacy of the shRNA knockdown.

Figure 24A:
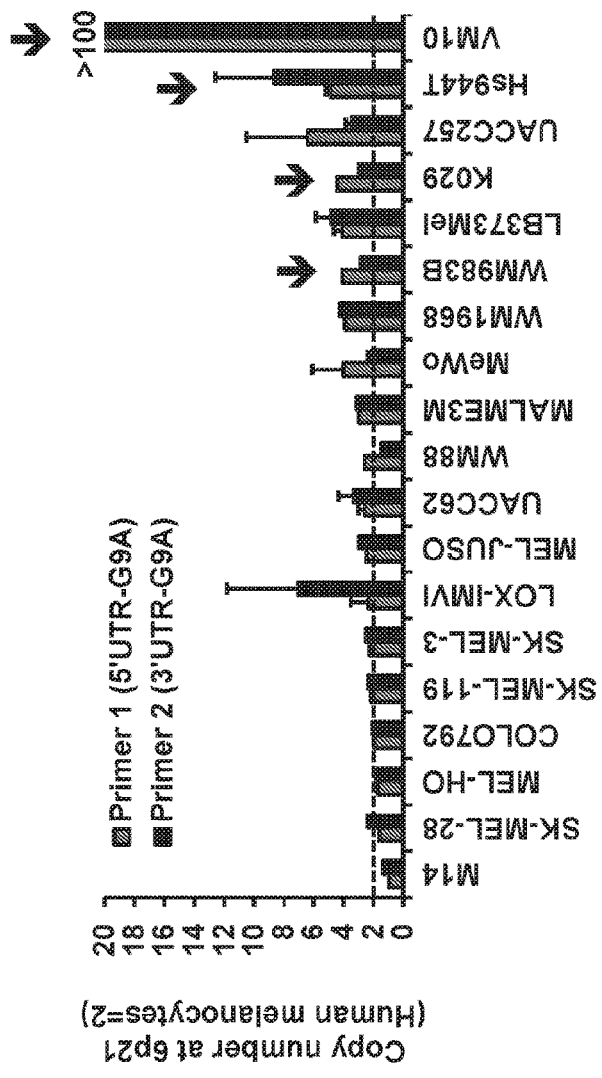
Figure 24B:
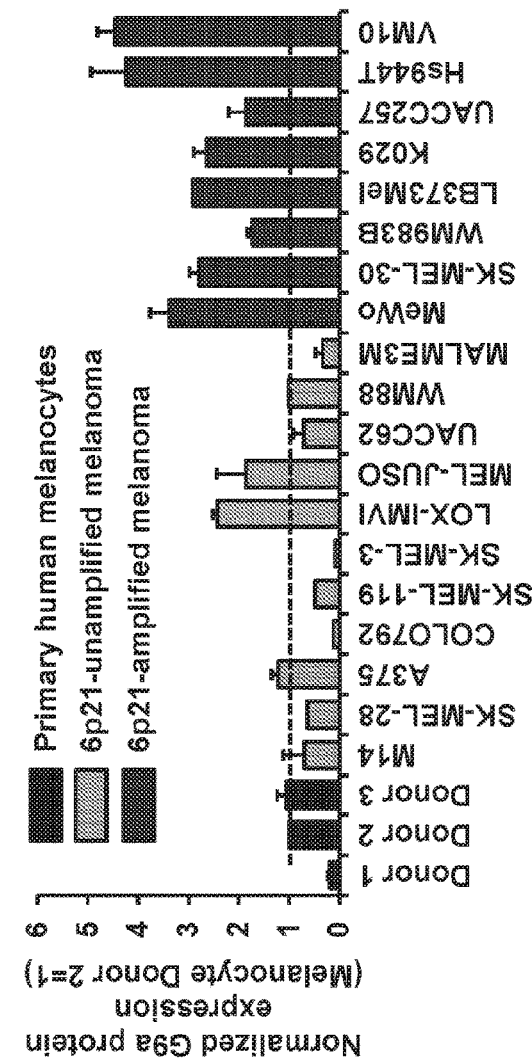
Figures 24C, 24D:
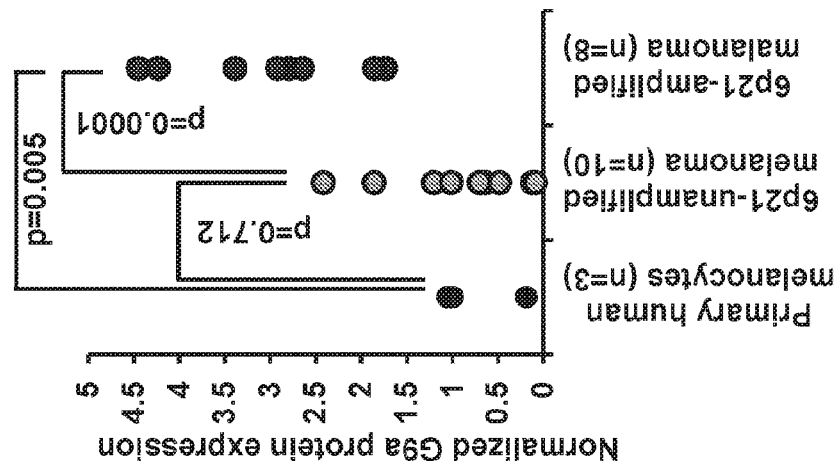

FIGS. 24A-24D show that melanoma cells with 6p21 amplification have higher G9a protein levels compared to non-6p21 amplified melanoma. FIG. 24A show the G9a copy number within the 6p21 amplicon in various cancers. G9a copy numbers are measured using G9a-specific primers. FIG. 24B shows G9a protein expressed normalized to melanocyte Donor 2. The comparison is made between primary human melanocytes, 6p21-unamplified melanoma, and 6p21-amplified melanoma. G9a protein expression is significantly increased in 6p21-amplified melanoma. FIG. 24C shows the comparison of copy number versus protein level for G9a. FIG. 24D show a normalized G9a protein expression for primary human melanocytes, 6p21-unamplified melanoma, and 6p21-amplified melanoma.

Figure 25B:
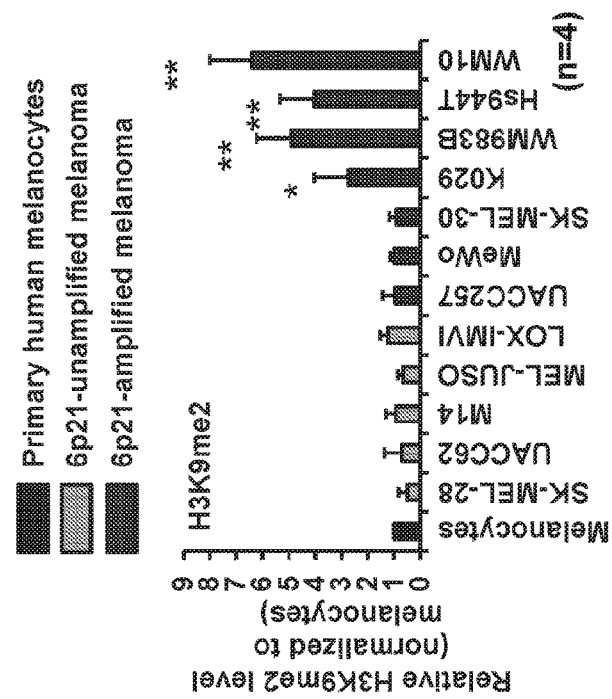
Figure 25D:
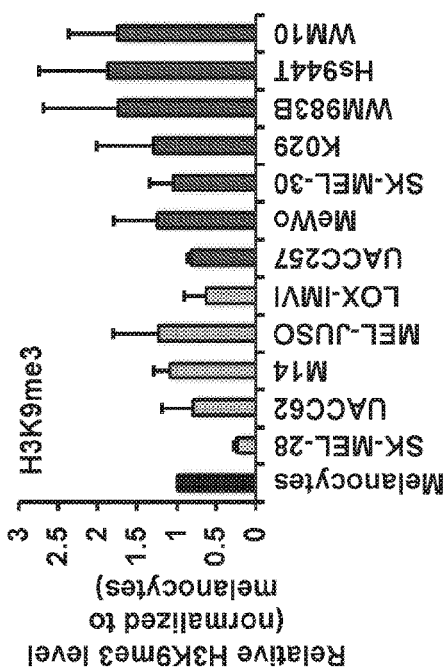
Figure 25A:
Figure 25C:
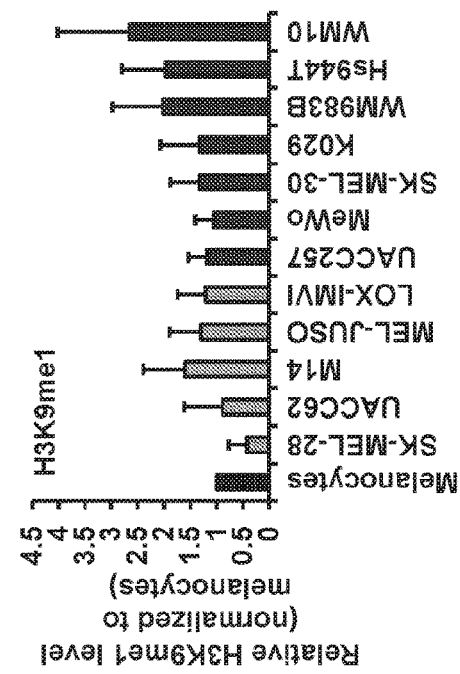

FIG. 25A-25D show that 6p21 amplification correlates with increased H3K9me2 levels. FIG. 25A shows a western blot probing the indicated cancer cell lines with antibodies against H3K9me1, H3K9me2, and H3K9me3. Only H3K9me2 is specifically increased in cancer lines with 6p21 amplification. (FIG. 25B) H3K9me2 levels (relative to melanocyte levels) were only increased in cancer cell lines containing a 6p21 amplicon ($*p=0.059$, $**p<0.01$ vs primary melanocytes), whereas (FIG. 25C) H3K9me1 and (FIG. 25D) H3K9me3 levels were increased in cancer cell lines that do not have a 6p21 amplicon.

FIGS. 26A and 26B show that G9a is required for oncogenic growth of 6p21-amplified melanoma. (FIG. 26A) Bar graph showing growth and survival of various cancer cell lines that are 6p21-amplified with high H3K9me2, 6p21-amplified with low H3K9me2, or 6p21-unamplified. Depletion of G9a significantly inhibited the growth of 6p21-amplified with high H3K9me2 cancer. $*p<0.05$, $**p<0.01$ vs shLuc (n=4). (FIG. 26B) Western blots confirming the efficacy of the G9a knockdown.

DETAILED DESCRIPTION

Unless otherwise explained, all technical and scientific terms used herein have the same meaning as commonly understood by one of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in biology, molecular biology, medicine, or genes can be found in the following sources: The Merck Manual of Diagnosis and Therapy, 19th Edition, published by Merck Sharp & Dohme Corp., 2011 (ISBN 978-0-911910-19-3) (2015 digital online edition at merckmanuals.com; Robert S. Porter et al. (eds.), The Encyclopedia of Molecular Cell Biology and Molecular Medicine, published by Blackwell Science Ltd., 1999-2012 (ISBN 9783527600908); The American Medical Association Encyclopedia of Medicine, Charles B. Clayman, MD, Medical Editor, Random House, New York, 1989; Robert A. Meyers (ed.), Molecular Biology and Biotechnology: a Comprehensive Desk Reference, published by VCH Publishers, Inc., 1995 (ISBN 1-56081-569-8); Biotechnology from A to Z, 2nd Edition, William Bains, Oxford University Press, New York, N.Y., 2002; A Dictionary of Genetics, 6th Edition, Robert C. King and William D. Stansfield, Oxford University Press, New York, N.Y., 2002; Dorland's Illustrated Medical Dictionary, 29th and 30th Editions, W. B. Saunders Company, Philadelphia, 2000, 2003; The Gale Encyclopedia of Genetic Disorders, Volumes I and II, Stacey L. Blachford, Ed., Thomson Learning, New York, N.Y., 2002; Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Benjamin Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737); The Merriam-Webster Dictionary, Merriam-Webster, Inc., Springfield, Mass., 1997; The Random House Dictionary of the English Language, Unabridged Edition, 1966; Webster's Ninth New Collegiate Dictionary, 1991; the contents of which are all incorporated by reference herein in their entireties. Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean ±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Figure 1:
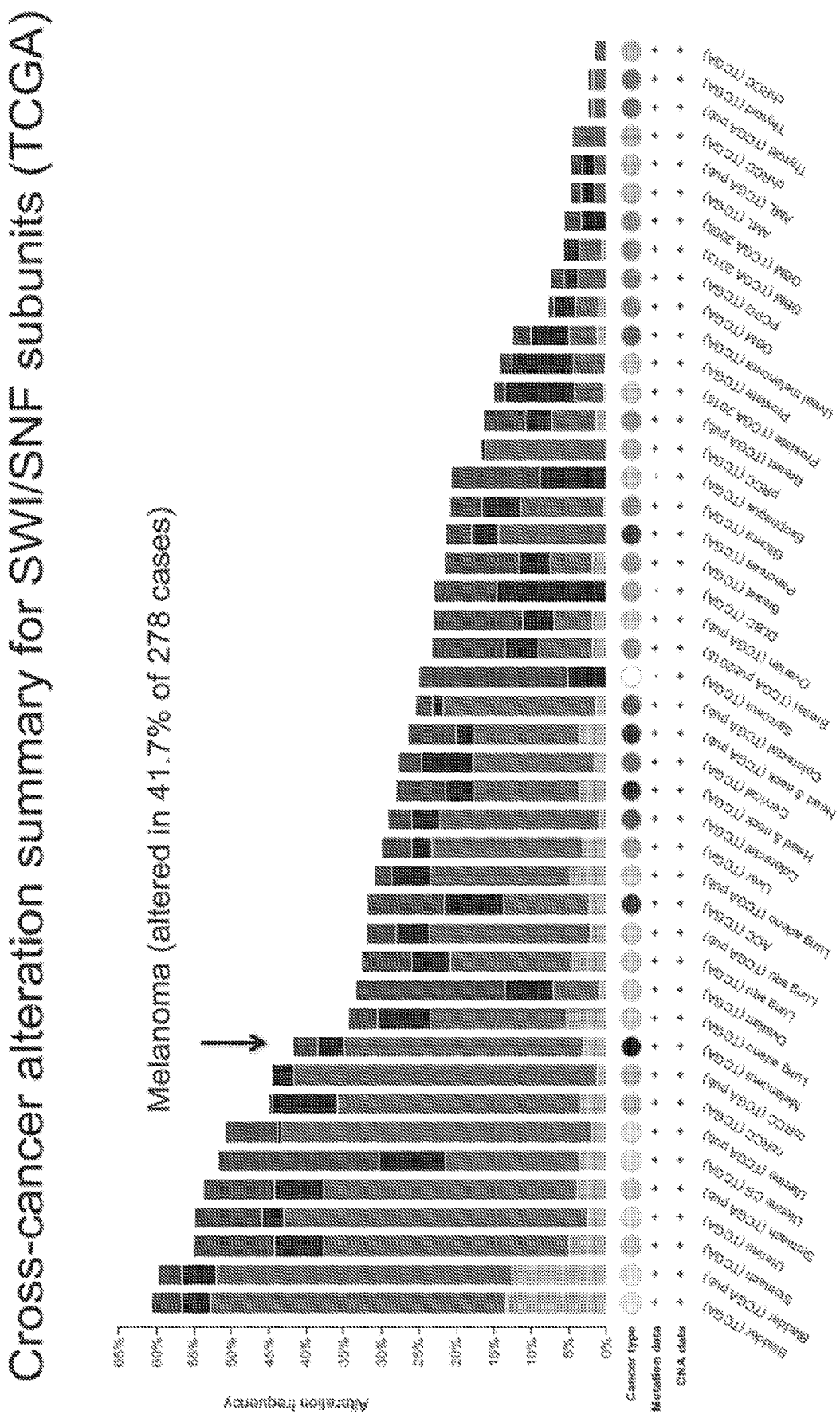
FIG. 1 shows the cross-cancer alteration summary for SWI/SNF subunits, data derived from The Cancer Genome Atlas (TCGA). SWI/SNF subunits are mutated in 30-40% of human melanomas in the database.
Figure 2:
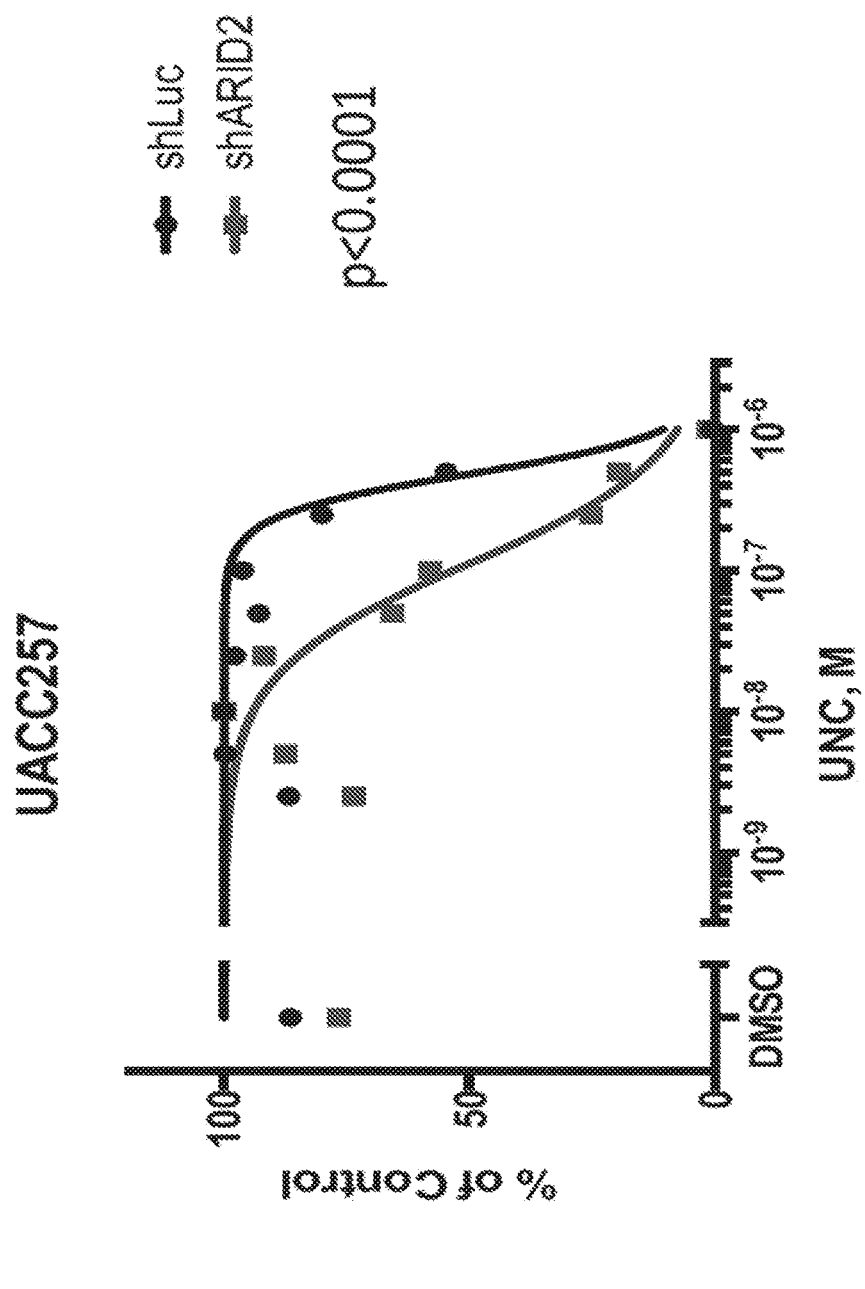
FIG. 2 shows the dose response of melanoma cells to the G9a inhibitor. UACC257 human melanoma cells with ARID2 deficiency are more susceptible to the G9a inhibitor UNC0638 compared to isogenically matched control cells. ARID2 deficiency is simulated the cells using an RNAi shARID2 to knockdown expression of ARID2. For control, the same cell lines are treated with a control RNAi shLuc instead of shARID2.
Figure 3:
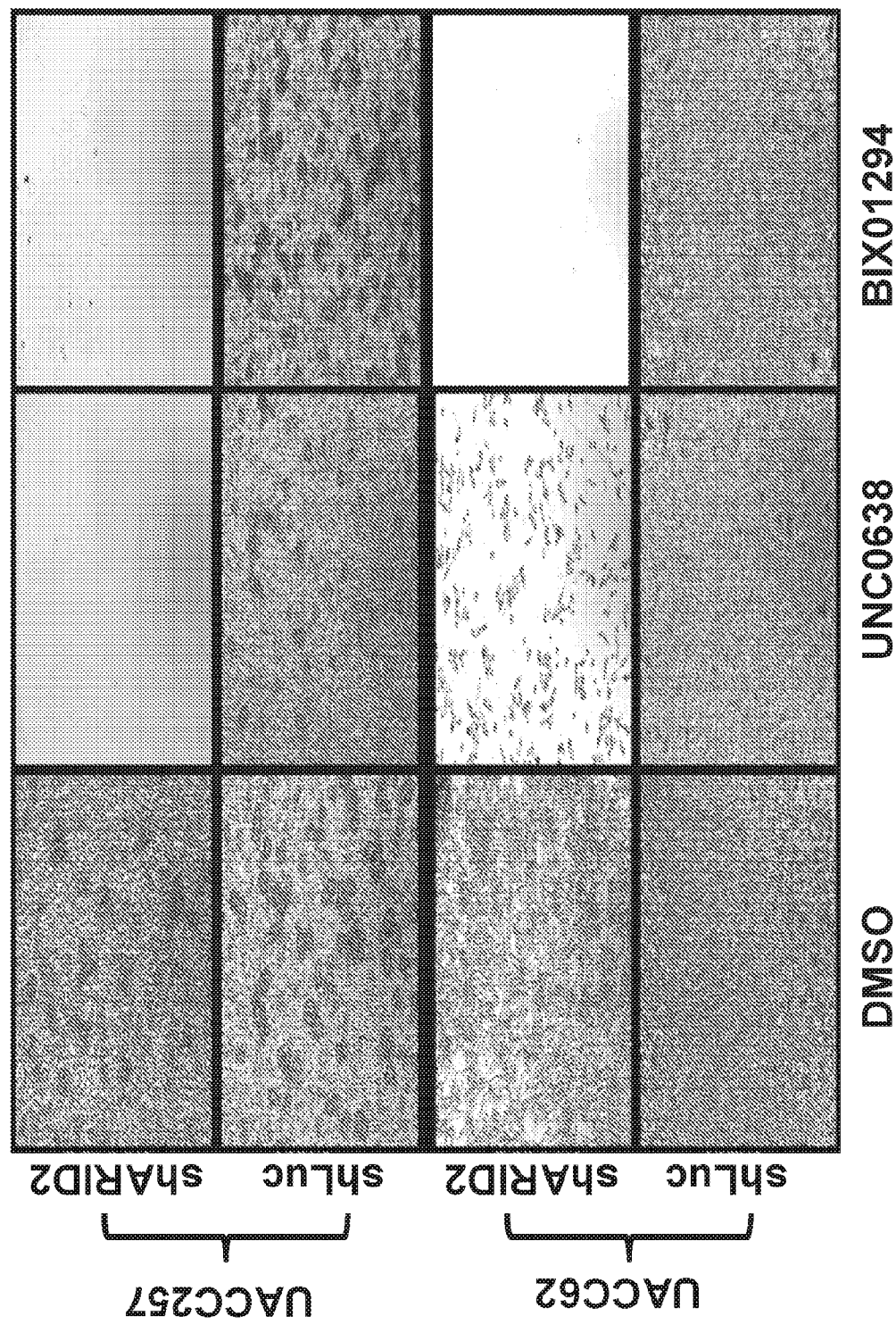
FIG. 3 shows the selective susceptibility of ARID2-deficient cells to G9a inhibitors, BIX01294 and UNC0638.

This present disclosure concerns the use of histone methyltransferase inhibitors, such as G9a/GLP inhibitors, in the treatment of cancers that have alterations in the SWI/SNF chromatin remodeling complex. The SWI/SNF complex functions in epigenetic regulation and is required for normal cell development and survival. It is altered in a significant portion of melanomas as well as a vast majority of known cancers (See FIG. 1 for the expanse of SWI/SNF alterations in cancers). The SWI/SNF alterations in cancers presents a particular therapeutic challenge, because the oncogenic changes are not driven directly by mutated proteins or molecules targetable by available drugs. The inventors show evidence that histone methyltransferase inhibitors, such as G9a/GLP inhibitors, can be used to treat cancer, for example, by promoting cell death of the cancer cells, by preventing, reducing, or inhibiting cell proliferation of the cancerous cells, and by preventing metastasis of aggressive cancers. The G9a/GLP inhibitors target the histone methyltransferase heteromeric complex G9a/GLP, which catalyzes the dimethylation of the H3K9 residue. Accordingly, non-limiting inhibitors of G9a and/or GLP such as UNC0638, UNC0224, UNC0631, UNC0642, UNC0646, BIX01294, A366, and Chaetocin are useful for the treatment of cancer having SWI/SNF alterations.

In one embodiment, provided here in is a method for treating cancer in a subject in need thereof comprising administering to a subject a therapeutically effective amount of an inhibitor of a histone methyltransferase, or a therapeutically effective amount of a composition comprising an inhibitor of a histone methyltransferase, wherein the cancer of the subject has been determined to have an alteration in the SWI/SNF chromatin remodeling complex.

In one embodiment, provided here in is a method for treating cancer in a subject consisting essentially of administering to a subject in need thereof a therapeutically effective amount of an inhibitor of a histone methyltransferase, or therapeutically effective amount of a composition comprising an inhibitor of a histone methyltransferase, wherein the cancer of the subject has been determined to have an alteration in the SWI/SNF chromatin remodeling complex.

In one embodiment of any one method described herein, the method further comprises first determining for an alteration of SWI/SNF chromatin remodeling complex in the cancer cells derived from the subject. In one embodiment of any one method described herein, the subject would have been diagnosed with cancer.

Accordingly, in one embodiment, provided here in is a method for treating of cancer in a subject in need thereof, the method comprising first determining for an alteration of SWI/SNF chromatin remodeling complex from cancer cells derived from a subject; and then administering to a subject an inhibitor of a histone methyltransferase, or a therapeutically effective amount of a composition comprising an inhibitor of a histone methyltransferase when it has been determined that there is an alteration in the SWI/SNF chromatin remodeling complex in the cancer cells in order to treat the subject.

In one embodiment of any one method described herein, the method further comprises first selecting a subject who had been diagnosed with cancer. The histone methyltransferase inhibitor is administered as the first cancer treatment in this subject.

In another embodiment of any one method described herein, the method further comprises first selecting a subject who had been diagnosed with cancer and has a recurrence of the cancer. For example, the cancer had responded to a prior cancer treatment, the subject was in remission, but the cancer has now re-appeared again (i.e., recurrence of the cancer). In other words, the histone methyltransferase inhibitor is now administered to a subject having a relapse or recurrence of cancer. The histone methyltransferase inhibitor is administered as a subsequent or secondary cancer treatment in this subject.

In one embodiment of any one method described herein, the previously administered at least one cancer treatment does not comprise an inhibitor of a histone methyltransferase or a combination of an inhibitor of a histone methyltransferase together with other inhibitors of epigenetic modification or other small molecule inhibitors described herein. For example, the previously administered at least one cancer treatment does not comprise an inhibitor of a histone methyltransferase together with addition inhibitors are histone deacetylase (HDAC) inhibitors, bromodomain inhibitors (BRD), histone demethylase inhibitors, and BRaf (B-Raf) inhibitors.

In another embodiment of any one method described herein, the cancer is an aggressive cancer. In another embodiment of any one method described herein, the method further comprises first selecting a subject who has an aggressive cancer.

In another embodiment of any one method described herein, the method further comprises first selecting a subject who has cancer and the cancer has not responded to a prior cancer treatment that does not comprise a histone methyltransferase inhibitor. For example, a subject who has been previously been treated with at least one cancer treatment and the cancer has not responded to the treatment. There has been no decrease or disappearance of signs and symptoms of cancer, e.g., shrinkage of the size of the tumor or number of abnormal cancer white blood cells. For example, the cancer grows, or spreads quickly (metastasis).

In one embodiment of any one method described herein, the selection step occurs prior to any administration of any cancer therapy drug. In one embodiment of any one method described herein, the selection step occurs prior to the administration of an inhibitor of a histone methyltransferase, or a therapeutically effective amount of a composition comprising an inhibitor of a histone methyltransferase.

In one embodiment of any one method described herein, the selection step occurs prior to any determination for an alteration of SWI/SNF chromatin remodeling complex in the cancer cells derived from the subject. In one embodiment of any one method described herein, those subjects in need of treatment include those already diagnosed with disease. In one embodiment of any one method described herein, those in need of treatment include those likely to develop metastases.

Accordingly, in one embodiment, provided here in is a method for treating of cancer in a subject in need thereof, the method comprising first selecting a subject who had been diagnosed with cancer, determining for an alteration of SWI/SNF chromatin remodeling complex in the cancer cells derived from the subject; and then administering to the subject an inhibitor of a histone methyltransferase, or therapeutically effective amount of a composition comprising an inhibitor of a histone methyltransferase when there is an alteration in the SWI/SNF chromatin remodeling complex in the cancer cells in order to treat the subject.

In one embodiment, provided here in is a method for treating of cancer in a subject in need thereof, the method comprising first selecting a subject who had been diagnosed with cancer, previously been treated for the cancer and the cancer has failed to respond to the prior treatment, determining for an alteration of SWI/SNF chromatin remodeling complex in the cancer cells derived from the subject; and then administering to the subject an inhibitor of a histone methyltransferase, or therapeutically effective amount of a composition comprising an inhibitor of a histone methyltransferase when there is an alteration in the SWI/SNF chromatin remodeling complex in the cancer cells in order to treat the subject.

In one embodiment, provided here in is a method for treating of cancer in a subject in need thereof, the method comprising first selecting a subject who had been a recurrence of cancer, determining for an alteration of SWI/SNF chromatin remodeling complex in the cancer cells derived from the subject; and then administering to the subject an inhibitor of a histone methyltransferase, or therapeutically effective amount of a composition comprising an inhibitor of a histone methyltransferase when there is an alteration in the SWI/SNF chromatin remodeling complex in the cancer cells in order to treat the subject. The subject had previously been successfully beet treated for that cancer, was in remission for a period of time and now the cancer has reappeared again after the period of remission.

In one embodiment, provided here in is a method for treating of cancer in a subject in need thereof, the method comprising first selecting a subject who an aggressive form of cancer, determining for an alteration of SWI/SNF chromatin remodeling complex in the cancer cells derived from the subject; and then administering to the subject an inhibitor of a histone methyltransferase, or therapeutically effective amount of a composition comprising an inhibitor of a histone methyltransferase when there is an alteration in the SWI/SNF chromatin remodeling complex in the cancer cells in order to treat the subject. In one embodiment of the of any one method described herein, the cancer is a Grade III or IV cancer. Such cancer cells tend to be poorly differentiated or undifferentiated and they look unlike the normal non-cancer cells from which the cancer cells originated. Such cancer cells also tend to divide rapidly.

In one embodiment of any one method described herein, diagnosing cancer in a subject can be performed by any method that is known in the art. These methods are well within the skill set of an oncologist or a skilled physician or a pathologist. For example, various methods of cancer diagnosis are taught and disclosed at the website of the USA National Cancer Institute and the American Cancer Society. The subject can be screened for cancer with a combination with diagnostics such as, for example, cancer biomarkers, mammography, manual examination, MRI, or tissue biopsy and histopathological examination. A skilled oncologist or physician will be able to differentially diagnosis cancer using medical diagnostic methods known within the art. A cancer pathologist would also be able to stage and grade the cancer/tumor cells, and determine whether the cancer is an aggressive form of cancer.

In one embodiment of any one method described herein, the cancer in the subject comprises rapidly dividing neoplastic cancer cells. In one embodiment of any one method described herein, the neoplastic cells of the subject require an efficient blood supply to maintain continued growth of the tumor. In one embodiment of any one method described herein, the cancer in the subject comprises to any of various malignant neoplasms that is characterized by the proliferation of anaplastic cells that tend to invade surrounding tissue and metastasize to new body sites. In other embodiments, the cancer in the subject comprises other the pathological condition characterized by such malignant neoplastic growths. The blood vessels provide conduits to metastasize and spread elsewhere in the body. Upon arrival at the metastatic site, the cancer cells then work on establishing a new blood supply network.

In one embodiment of any one method described herein, the cancer in the subject comprises malignant cancer. In one embodiment of any one method described herein, the cancer in the subject has metastasized in the subject.

In one embodiment of any one method described herein, the cancer in the subject comprises primary cancers (ie., cancers growing at the original location or site or cancers growing form the original tissue type) and at secondary tumor sites (ie., metastasized cancers or tumors).

In one embodiment of any one method described herein, the cancer to be treated in the subject as described herein include, but are not limited to carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In one embodiment of any one method described herein, the cancer to be treated in the subject as described herein include, but are not limited to the following cancer types: Adenoid cystic carcinoma, Non-melanoma skin cancer, Hepatocellular carcinoma, Head and neck squamous cell carcinoma, Gastric cancer, Clear cell renal cell carcinoma, Prostate cancer, Lung cancer (adenocarcinoma and squamous cell carcinoma), Small-cell carcinoma of the ovary, hypercalcemic type (malignant rhabdoid tumor of the ovary), Rhabdoid tumor, Medulloblastoma, Lung adenocarcinoma, Mantle cell lymphoma, Burkitt lymphoma, Esophageal adenocarcinoma, melanoma, Intraductal papillary mucinous neoplasms of the pancreas, Schwannoma, Meningioma, Epitheloid sarcoma, Cribriform neuroepithelial tumor, Renal medullary carcinoma, Colorectal carcinoma, Cervical intraepithelial neoplasia, Breast cancer, Colon cancer, Neuroblastoma, Multiple spinal meningiomas, Urothelial cancer, Pericytoma with t(7;12), Diffuse large B-cell lymphoma, Esophageal adenocarcinoma, Esophageal adenocarcinoma, Colorectal cancer, Esophageal adenocarcinoma, Ovarian clear cell carcinoma, Endometrioid ovarian carcinoma, Endometrial carcinoma, Cervical carcinoma, Pancreatic ductal adenocarcinoma, Pancreatic carcinoma with acinar differentiation, Intrahepatic cholangiocarcinomas, Gastric adenocarcinoma, Esophageal adenocarcinoma, Oseophagogastric junctional adenocarcinoma, Renal clear cell carcinoma, Transitional cell carcinoma of the bladder, Urothelial bladder carcinoma, Medulloblastoma, Pulmonary carcinoids, Adenoid cystic carcinoma, Burkitt lymphoma, Diffuse large B-cell lymphoma, Follicular lymphoma, Pilocytic astrocytoma, Mycosis fungoides (primary cutaneous T cell lymphoma subtype), Multiple myeloma, Cutaneous T cell lymphoma, Pilocytic astrocytoma, Non-small cell lung cancer, Lung squamous cell carcinoma, Chronic lymphocytic leukemia, Acute lymphoblastic leukemia, Acute myeloid leukemia, Low-grade B cell lymphoma, Mediastinal B cell lymphoma, Diffuse large B-cell lymphoma, Marginal zone B cell lymphoma, Gray zone lymphoma, Classical Hodgkin lymphoma, Acute myeloid leukemia, T cell acute lymphoblastic leukemia, Mycosis fungoides (primary cutaneous T cell lymphoma subtype), Adult T cell leukemia/lymphoma, Head and neck squamous cell carcinoma, Synovial sarcoma, Synovial sarcoma, Intrahepatic cholangiocarcinomas, Gallbladder carcinoma, Pancreatic ductal adenocarcinoma, Esophageal adenocarcinoma, Oral squamous cell carcinoma (gingivobuccal), Epithelial ovarian carcinoma, and Nasopharyngeal carcinoma.

In one embodiment of any one method described herein, determining an alteration in the SWI/SNF chromatin remodeling complex in the cancer derived from the subject can be performed by any method known in the art. In one embodiment of any one method described herein, the determining can be performed together with the diagnosis of cancer.

Cancer cells can be obtained from a subject diagnosed with or suspected of having cancer. For example, cancer cells can be obtained from a tissue biopsy or an excised tumor during a routine surgery to remove cancerous tumors.

In one embodiment of any one method described herein, determining an alteration in the SWI/SNF chromatin remodeling complex in the cancer in the subject further comprises providing a tissue sample comprising cancer cells obtained from the subject. A skilled physician or surgeon will be able to obtain a tissue biopsy or excised a tumor from a subject.

In one embodiment of any one method described herein, the tissue sample is a tumor sample. In another embodiment, the tissue sample contains cancerous cells.

In one embodiment of any one method described herein, the tissue sample is obtained from a biopsy procedure in the subject. In another embodiment of any one method described herein, the tissue sample is obtained from a surgical procedure to remove a tumor mass from the subject.

In one embodiment of any one method described herein, the alteration the SWI/SNF chromatin remodeling complex is the result in a deficiency in one or more of the subunit member of the complex.

In one embodiment of any one method described herein, the deficiency is due to a mutation in a gene encoding for one or more of subunit members that make up the SWI/SNF chromatin remodeling complex.

In one embodiment of any one method described herein, the deficiency is determined by DNA sequencing.

In one embodiment of any one method described herein, the subunits that are tested for deficiency are selected from the group consisting of BRMISMARCA2; BRG1/SMARCA4; ARID1A; ARID2; SMARCR2; SMARCR1; SMARCB1; and PBRM1. The protein abbreviated name of each subunit is in capital letters and the corresponding gene encoding for the protein in given in italic capital letters.

In other embodiments of any one method described herein, the subunit component of the SWI/SNF chromatin remodeling complex that is tested for alterations or deficiency include BRM/SMARCA2, BRG1/SMARCA4, BAF47/SMARCB1, BAF155/SMARCC1, BAF170/SMARCC2, BAF60A/SMARCD1, BAF60B/SMARCD2, BAF60C/SMARCD3, BAF57/SMARCE1, BAF53A/ACT6A, BAF53B/ACT6B, and Beta-actin/ACTB. The protein abbreviated name of each subunit is in capital letters and the corresponding gene encoding for the protein in given in italic capital letters.

In other embodiments of any one method described herein, the subunit component of the SWI/SNF chromatin remodeling complex that is tested for alterations or deficiency include the BAF complex subunits: BAF45B/DPF1, BAF45C/DPF3, BAF45D/DPF2, BAF250A/ARID/A, BAF250B/ARID1B, BCL7A/BCL7A, BCL7B/BCL7B, BCL7C/BCL7A, BCL11A/BCL11A, BCL11B/BCL11B, BRD9/BRD9, SS18L1/CREST, and SS18/SYT. The protein abbreviated name of each subunit is in capital letters and the corresponding gene encoding for the protein in given in italic capital letters.

In other embodiments of any one method described herein, the subunit component of the SWI/SNF chromatin remodeling complex that is tested for alterations or deficiency include the BAF complex subunits: PBAF complex subunits: BAF45A/PHF10, BAF180/PBRM1, BA200/ARID2, and BRD7/BRD7. The protein abbreviated name of each subunit is in capital letters and the corresponding gene encoding for the protein in given in italic capital letters.

In one embodiment of any one method described herein, the mutation is a deletion, a single nucleotide variant (SNV), or an amplification a gene encoding for one or more of subunit members that make up the SWI/SNF chromatin remodeling complex.

In one embodiment of any one method described herein, the mutation is an inactivating mutation.

In one embodiment, the SNV is an inactivating SNV.

Following procurement of the tissue biopsy sample, the tissue sample is fixed in formaldehyde and subsequently embedded in paraffin wax within a mold to protect the tissue and allow for analysis of thin cross sections. To identify deficiency of ARID2 and other SWI/SNF components in the complex (See Table 1 for the components that are associated with cancers and are to be tested for alterations such as deficiency), the clinical pathologist utilizes a variety of molecular techniques known in the art to determine the presence of an alteration. Non-limiting molecular techniques for determining the presence of an alteration include DNA sequencing and polymerase chain reaction (PCR) to quantify RNA expression.

In order to prepare samples for PCR, it is necessary to first isolate RNA from the tissue sample. RNA extraction is a well-established protocol and can be performed on fresh tissue samples according to the general protocols described at the QIAGEN website under the section on sample and technologies relating to RNA preparation using QIAGEN RNEASY-MINI-KIT. Following RNA isolation, quantitative PCR can be performed using any standard qPCR kit and primers against the gene of interest (ie. ARID2). This provides a rapid and cost-effective means of identifying alterations in expression of SWI/SNF component genes. In other embodiments, clinical exome sequencing can be used to identify mutations within SWI/SNF complex genes. This requires specialized equipment including a sequencer, and hospitals that do not have their own machines have processes in place to outsource the sequencing procedure to other facilities. For example, see the pathology website at the UCLA for additional information and references relating to clinical exom sequencing of a tissue biopsy sample. (Lee H, et al., JAMA. 2014, 312(18):1880-7, "Clinical exome sequencing for genetic identification of rare Mendelian disorders.")

In one embodiment of any one method described herein, the inhibitors of histone methyltransferase described herein, are small molecules.

In one embodiment of any one method described herein, the histone methyltransferase inhibitor is selected from the group consisting of AMI-1, A-366, BIX-01294, BIX01338, BRD4770, chaetocin, UNC0224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, and EPZ-6438. In other embodiments, the histone methyltransferase inhibitor include but is not limited to those disclosed in United States Patent Application No: US20150274660, the contents are incorporated herein by reference in its entirety.

In one embodiment of any one method described herein, the inhibitor of a histone methyltransferase is an inhibitor of the histone methyltransferase heteromeric complex G9a/GLP, also known as a G9a inhibitor. For examples, BRD4770, UNC0631, and BIX01294 are potent and specific G9a methyltransferase inhibitor.

Euchromatic histone-lysine N-methyltransferase 2 (EHMT2), (EC:2.1.1.-, EC:2.1.1.43) also known as G9a, is a histone methyltransferase that in humans is encoded by the EHMT2 gene. G9a and G9a-like protein, another histone-lysine N-methyltransferase, catalyze the dimethylated state of H3K9me2. G9a is an important control mechanism for epigenetic regulation within the nucleus accumbens. Methylation occurs at the c amino group of lysine residues. Methylation of histone H3 Lys 9 is a hallmark of silent chromatin (therefore gene repression) and is globally distributed throughout the heterochromatic regions, such as centromeres and telomeres. H3K9me represents a specific tag for epigenetic transcriptional repression by recruiting HP1 proteins to methylated histones.

In one embodiment, provided here in is a method for treating of cancer in a subject in need thereof, the method comprising administering a composition comprising an inhibitor of a histone methyltransferase heteromeric complex G9a/GLP. In one embodiment, the cancer of the subject has been determined to have an alteration in the SWI/SNF chromatin remodeling complex.

In one embodiment of any one method described herein, the inhibitor of a histone methyltransferase is an inhibitor of the histone methyltransferase Enhancer of zeste homolog 2 (EZH2). For examples, GSK503, GSK 126, UNC1999, EI1, EPZ005687, EPZ-6438, and CPI-169 are potent and specific EZH2 methyltransferase inhibitor.

Enhancer of zeste homolog 2 (EZH2) is a histone-lysine N-methyltransferase enzyme (EC 2.1.1.43) encoded by EZH2 gene, that participates in DNA methylation and, ultimately, transcriptional repression. (Vire E, et al., 2006, Nature 439: 871-4). EZH2 catalyzes the addition of methyl groups to histone H3 at lysine 27, (Cao R, et al., 2002, Science 298: 1039-43) by using the cofactor S-adenosyl-L-methionine. Methylation activity of EZH2 facilitates heterochromatin formation thereby silences gene function. (Viré E, et al., Supra). Remodeling of chromosomal heterochromatin by EZH2 is also required during cell mitosis.

EZH2 is the functional enzymatic component of the polycomb repressive complex 2 (PRC2), which is responsible for healthy embryonic development through the epigenetic maintenance of genes responsible for regulating development and differentiation. (Morey L. and Helin K, 2010, Trends Biochem. Sci. 35: 323-32) EZH2 is responsible for the methylation activity of PRC2, and the complex also contains proteins required for optimal function (EED, SUZ12, JARID2, AEBP2, RbAp46/48, and PCL). (Margueron R. and Reinberg D, 2011, Nature 469: 343-9). EZH2 activity and expression is tightly associated with cell proliferation.

EZH2 is the catalytic subunit of the Polycomb repressive complex 2 (PRC2). (See UniProt: Q15910) EZH2's catalytic activity relies on its formation of a complex with at least two other PRC2 components, SUZ12 and EED. (Tan J Z, et al., 2014, Acta Pharmacol. Sin. 35: 161-74) As a histone methyltransferase (HMTase), EZH2's primary function is to methylate Lys-27 on histone 3 (H3K27me) by transferring a methyl group from the cofactor S-adenosyl-L-methionine (SAM), although recent studies have indicated that it is also capable of methylating non-histone proteins. (Tan J Z, et al., supra; Lund K, et al., 2014, Leukemia 28: 44-9) EZH2 is capable of mono-, di-, and tri-methylation of H3K27 and has been associated with a variety of biological functions, including transcriptional repression and activation, hematopoiesis, development, and cell differentiation.

Methylation of the histone is a histone modification that has been characterized as part of the histone code. The histone code is the theory that chemical modifications, such as methylation, acetylation, and ubiquitination, of histone proteins play distinctive roles in epigenetic regulation of gene transcription. EZH2-mediated catalysis of H3K27me3 is associated with long term transcription repression.

Mutation or over-expression of EZH2 has been linked to many to forms of cancer. (Kim, K. and Roberts, C., 2015, Nature Medicine 22:128-134) EZH2 inhibits genes responsible for suppressing tumor development, and blocking EZH2 activity may slow tumor growth. EZH2 has been targeted for inhibition because it is upregulated in multiple cancers including, but not limited to, breast, prostate, melanoma, and bladder cancer. Mutations in the EZH2 gene are also associated with Weaver syndrome, a rare congenital disorder, and EZH2 is involved in causing neurodegenerative symptoms in the nervous system disorder, ataxia telangiectasia.

In one embodiment, provided here in is a method for treating of cancer in a subject in need thereof, the method comprising administering a composition comprising an inhibitor of a histone methyltransferase EZH2. In one embodiment, the cancer of the subject has been determined to have an alteration in the SWI/SNF chromatin remodeling complex.

It is contemplated that a combination of histone methyltransferase inhibitors can be used to treat cancers that have an alteration in the SWI/SNF chromatin remodeling complex, the combination of inhibitors would target different histone methyltransferases. For example, a combination of inhibitors that target the G9 histone methyltransferase and the EZH2 histone methyltransferase.

In one embodiment, provided here in is a method for treating of cancer in a subject in need thereof, the method comprising administering a composition comprising an inhibitor of a histone methyltransferase EZH2, and an inhibitor of a histone methyltransferase G9a, wherein the cancer of the subject has been determined to have an alteration in the SWI/SNF chromatin remodeling complex.

In one embodiment of any one method described herein, the method further comprises first selecting a subject who had been diagnosed with cancer. The G9a inhibitor and EZH2 inhibitor are administered as the first cancer treatment in this subject.

In another embodiment of any one method described herein, the method further comprises first selecting a subject who had been diagnosed with cancer and has a recurrence of the cancer.

In another embodiment of any one method described herein, the method further comprises first selecting a subject who has cancer and the cancer has not responded to a prior cancer treatment that does not comprise a G9a inhibitor or a EZH2 inhibitor or both inhibitors.

In another embodiment of any one method described herein, the cancer is an aggressive cancer. In another embodiment of any one method described herein, the method further comprises first selecting a subject who has an aggressive cancer.

In one embodiment of any one method described herein, the method further comprises first determining for an alteration of SWI/SNF chromatin remodeling complex in the cancer cells derived from the subject. In one embodiment of any one method described herein, the subject would have been diagnosed with cancer.

In one embodiment of any one method described herein, the inhibitor of a histone methyltransferase described herein is formulated as a composition. For example, formulated as a composition for an oral or systemic administration. In another embodiment, the composition is formulated for sustained delivery in vivo.

In one embodiment of any one method described herein, the compositions described herein are formulated for oral or systemic application to the subject. In one embodiment of any one method described herein, the compositions described herein are formulated for sustained delivery in vivo.

In one embodiment of any one method described herein, the inhibitor described herein or combination thereof is administered by a route selected from the group consisting of oral, intravenous, intramuscular, subcutaneous, intradermal, transdermal, topical, intraperitoneal, intrathecal, intrapleural, intrauterine, rectal, vaginal, intrasynovial, intraocular/periocular, aerosol, intratumor, and parenteral administration.

In one embodiment of any method described herein, the composition comprising an inhibitor described herein is formulated to be administered by a route selected from the group consisting of: oral, intravenous, intramuscular, subcutaneous, intradermal, transdermal, topical, intraperitoneal, intrathecal, intrapleural, intrauterine, rectal, vaginal, intrasynovial, intraocular/periocular, intratumor, aerosol and parenteral administration. In one embodiment of any method described herein, the composition comprising an inhibitor described herein further comprises a pharmaceutically acceptable carrier.

In one embodiment of any one method described herein, the subject is a mammal. In one embodiment of any one method described herein, the subject is a primate mammal. In one embodiment of any one method described herein, the mammal is a human.

In one embodiment of any one method described herein, the composition or the inhibitor described herein or combination thereof further comprises a pharmaceutically acceptable carrier.

In one embodiment of any method described herein, the composition comprising an inhibitor described herein, or the inhibitor described herein or combination thereof is administered in conjunction with at least one additional cancer therapy to achieve a combination cancer therapy.

In one embodiment of any method described herein, wherein the at least one additional cancer therapy is selected from the group consisting of radiation therapy, chemotherapy, immunotherapy and gene therapy.

In other embodiments of any method described herein, the at least one additional cancer therapy is selected from the group consisting of growth inhibitory agents, cytotoxic agents, anti-angiogenesis agents, apoptotic agents, anti-tubulin agents, anti-HER-2 antibodies, anti-CD20 antibodies, an epidermal growth factor receptor (EGFR) antagonist, a HER1/EGFR inhibitor, a platelet derived growth factor inhibitor, a COX-2 inhibitor, an interferon, and a cytokine (e.g., G-CSF, granulocyte-colony stimulating factor).

In other embodiments of any method described herein, the at least one additional cancer therapy is selected from the group consisting of 13-cis-retinoic acid, 2-CdA, 2-Chlorodeoxyadenosine, 5-Azacitidine, azacytidine, 5-Fluorouracil, 5-FU, 6-Mercaptopurine, 6-MP, 6-TG, 6-Thioguanine, abiraterone acetate, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, , All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Cabazitaxel, Calcium Leucovorin, Campath® Camptosar® Camptothecin-11, Capecitabine, Caprelsa® Carac™ Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin®, Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eculizumab, Efudex®, Eligard™, Ellence™, Eloxatin™, Elspar®, Emcyt®, Epirubicin, Epoetin Alpha, Erbitux, Eribulin, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, Gefitinib, Gemcitabine, Gemtuzumab ozogamicin, Gemzar, Gleevec™, Gliadel® Wafer, Goserelin, Granulocyte-Colony Stimulating Factor (G-CSF), Granulocyte Macrophage Colony Stimulating Factor (GM-CSF), Halaven®, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta®, Interferon alpha, Interferon Alpha-2b (PEG Conjugate), Interleukin-2, Interleukin-11, Intron A® (interferon alpha-2b), Ipilimumab, Iressa®, Irinotecan, Isotretinoin, Ixabepilone, Ixempra™, Jevtana®, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolia®, Prolifeprospan 20 with Carmustine Implant, Provenge®, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Sipuleucel-T, Soliris®, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Valrubicin, Valstar, vandetanib, VCR, Vectibix™, Velban®, Velcade®, Vemurafenib, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xalkori capsules, Xeloda®, Xgeva®, Yervoy®, Zanosar®, Zelboraf, Zevalin™, Zinecard®, Zoladex®, Zoledronic acid, Zolinza, Zometa®, and Zytiga®.

In one embodiment, the at least one additional cancer therapy is not a histone methyltransferase inhibitor, or a histone demethylase inhibitor, or a HDAC inhibitor, or a BRaf inhibitor, or a BRD inhibitor.

In one embodiment, the at least one additional cancer therapy is not AMI-1, A-366, BIX-01294, BIX01338, BRD4770, chaetocin, UNCO224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, or EPZ-6438.

In one embodiment, the at least one additional cancer therapy is not OTX015, CPI-203, PFI-3, PFI-4, GSK1324726A (I-BET726), MS436, OF-1, bromosporine, SGC-CBP30, GSK2801 ZEN3365, JQ1, PF-1, RVX-208, PFI-1 (PF-6405761), I-BET151 (GSK1210151A) or TEN010

In one embodiment, the at least one additional cancer therapy is not GSKJ4, GSK J1, OG-L002, JIB-04, SP2509, ORY-1001 (RG-6016), IOX1, GSK-LSD1 2HCl, or GSK J1

In one embodiment, the at least one additional cancer therapy is not M344, Vorinostat (suberoylanilide hydroxamic acid, SAHA, MK0683), entinostat (MS-275), panobinostat (LBH589), trichostatin A (TSA), mocetinostat (MGCD0103), Belinostat (PXD101), Romidepsin (FK228, Depsipeptide), MC1568, Tubastatin A HCl, Givinostat (ITF2357), LAQ824 (Dacinostat) CUDC-101 Quisinostat (JNJ-26481585) 2HCl, Pracinostat (SB939) PCI-34051 Droxinostat Droxinostat PCI-24781 (Abexinostat), RGFP966, AR-42, Rocilinostat (ACY-1215), Valproic acid sodium salt (Sodium valproate), CI994 (Tacedinaline), CUDC-907, Tubacin, RG2833 (RGFP109), Resminostat Sodium Phenylbutyrate, Tubastatin A, HPOB, Tasquinimod, 4SC-202 TMP269 CAY10603 BRD73954 BG45 LMK-235, or Nexturastat A.

In one embodiment, the at least one additional cancer therapy is not BAY43-9006 (Sorafenib, Nexavar), PLX4032 (Vemurafenib), GDC-0879, SB590885 S7108 Encorafenib (LGX818), RAF265 (CHIR-265), Dabrafenib (GSK2118436), TAK-632, PLX-4720, CEP-32496, Sorafenib Tosylate (Bay 43-9006), Sorafenib Sorafenib, or AZ 628.

In one embodiment of any method described herein, the method further comprises administering a drug that treats at least one symptom of cancer or cancer therapy. For example, for low blood count or anemia resulting from the chemo- or radiation therapy, erythropoietin can be administered to promote de novo the production of blood cell cells.

Through a synthetic lethality screen of epigenetic small molecule inhibitors and subsequent in vitro experiments, the inventors also show that melanomas deficient in the SWI/SNF complex are uniquely susceptible G9a/GLP inhibitors and other epigenetic small molecule inhibitors, which indicate unique epigenetic dependencies within these tumor cells. The inventors demonstrated the specificity of this vulnerability using both cell lines with engineered knockdown of SWI/SNF components as well as melanomas intrinsically deficient in the SWI/SNF complex. Cells with intact SWI/SNF complex function are spared from the cytotoxic effects of the G9a/GLP inhibitors.

In one embodiment of any of the cancer treatment method described herein, additional epigenetic small molecule inhibitors are administered in conjunction with the histone methyltransferase inhibitor to treat the cancer and promote cancer cell death. For example, the addition epigenetic small molecule inhibitors are histone deacetylase (HDAC) inhibitors, bromodomain inhibitors (BRD), histone demethylase inhibitors, and BRaf (B-Raf) inhibitors.

Histone deacetylases (HDAC) are enzymes that catalyze the removal of acetyl groups from lysine residues. This promotes a more condensed configuration of the chromatin structure, correlating with transcriptional silencing. HDAC inhibitors reverse this effect and are already FDA approved for use in the clinic. Two HDAC inhibitors, vorinostat (SAHA) and romidepsin are currently used in dermatology and oncology for treatment of cutaneous T cell lymphoma. We have tested SAHA in combination with G9a inhibitors and showed enhanced killing of melanoma cells when the two compounds are used concurrently.

Bromodomains (BRDs) refer to protein domains that recognize acetylated lysine residues and participate in epigenetic signal transduction. Members of the BRD family such as BRD4 have been implicated in oncogenic mechanisms, and several BRD inhibitors have been developed. Presently, the BRD inhibitor I-BET-762 is undergoing clinical trials for oncological applications. We have demonstrated potent synergistic activity when BRD inhibitors are combined with G9a inhibitors.

Histone demethylases catalyze the removal of methyl groups from DNA and histones and have shown to be important in melanoma development. Multiple histone demethylase inhibitors have been developed, including GSK J1, GSK J4, IOX1, and PBIT. Inhibitors of the lysine-specific histone demethylase LSD1 have been shown to have efficacy in leukemia and other cancers.

The role of BRAF in oncogenesis is well established, and multiple BRAF inhibitors are FDA-approved for advanced melanoma. BRAF is a serine/threonine-specific protein kinase that regulates the MAP kinase/ERK signaling pathway to control cell differentiation and proliferation. Many BRAF driver mutations have been identified to be important in human cancers, the most well-characterized of which is the BRAF (V600E) mutation. The inventors have shown enhanced killing of melanoma cells when BRAF inhibitors are used in combination with G9a inhibitors.

In one embodiment, provided here in is a method for treating of cancer in a subject in need thereof, the method comprising administering a composition comprising an inhibitor of a histone methyltransferase and a HDAC inhibitor, wherein the cancer of the subject has been determined to have an alteration in the SWI/SNF chromatin remodeling complex. In one embodiment, the histone methyltransferase inhibitor is a G9a inhibitor. In another embodiment, the histone methyltransferase inhibitor is a EZH2 inhibitor.

In one embodiment, provided here in is a method for treating of cancer in a subject in need thereof, the method comprising administering a composition comprising an inhibitor of a G9a histone methyltransferase and a HDAC inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase EZH2 and a HDAC inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2 and a HDAC inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase and an inhibitor of B-Raf, wherein the cancer of the subject has been determined to have an alteration in the SWI/SNF chromatin remodeling complex. In one embodiment, the histone methyltransferase inhibitor is a G9a inhibitor. In another embodiment, the histone methyltransferase inhibitor is a EZH2 inhibitor.

In one embodiment, provided here in is a method for treating of cancer in a subject in need thereof, the method comprising administering a composition comprising an inhibitor of a histone methyltransferase EZH2 and an inhibitor for a B-Raf enzyme (a B-Raf inhibitor), wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a and a B-Raf inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2 and a B-Raf inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase and an inhibitor for a member of the BET (bromodomain and extra terminal domain) family of bromodomain proteins (BRD) (a BRD inhibitor), wherein the cancer of the subject has been determined to have an alteration in the SWI/SNF chromatin remodeling complex. In one embodiment, the histone methyltransferase inhibitor is a G9a inhibitor. In another embodiment, the histone methyltransferase inhibitor is a EZH2 inhibitor.

A bromodomain is an approximately 110 amino acid protein domain that recognizes acetylated lysine residues, such as those on the N-terminal tails of histones. Bromodomains, as the "readers" of lysine acetylation, are responsible in transducing the signal carried by acetylated lysine residues and translating it into various normal or abnormal phenotypes.

In one embodiment, provided here in is a method for treating of cancer in a subject in need thereof, the method comprising administering a composition comprising an inhibitor of a histone methyltransferase EZH2 and a BRD inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a and a BRD inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2, and a BRD inhibitor, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase and an inhibitor of a histone demethylase, wherein the cancer of the subject has been determined to have an alteration in the SWI/SNF chromatin remodeling complex. In one embodiment, the histone methyltransferase inhibitor is a G9a inhibitor. In another embodiment, the histone methyltransferase inhibitor is a EZH2 inhibitor.

In one embodiment, provided here in is a method for treating of cancer in a subject in need thereof, the method comprising administering a composition comprising an inhibitor of a histone methyltransferase EZH2 and an inhibitor of a histone demethylase, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a and an inhibitor of a histone demethylase, wherein the cancer of the subject has been determined to have an alteration in the SWI/SNF chromatin remodeling complex.

In one embodiment, provided here in is a method for treating of cancer in a subject in need thereof, the method comprising administering a composition comprising an inhibitor of a histone methyltransferase G9a, an inhibitor of a histone methyltransferase EZH2, and an inhibitor of a histone demethylase, wherein the cancer of the subject has been determined to have an alteration in the SWI/SNF chromatin remodeling complex.

In one embodiment of any one method described herein, the method further comprises first selecting a subject who had been diagnosed with cancer.

In another embodiment of any one method described herein, the method further comprises first selecting a subject who had been diagnosed with cancer and has a recurrence of the cancer.

In another embodiment of any one method described herein, the method further comprises first selecting a subject who has cancer and the cancer has not responded to a prior cancer treatment that does not comprise a G9a inhibitor or a EZH2 inhibitor or both inhibitors.

In another embodiment of any one method described herein, the cancer is an aggressive cancer. In another embodiment of any one method described herein, the method further comprises first selecting a subject who has an aggressive cancer.

In one embodiment of any one method described herein, the method further comprises first determining for an alteration of SWI/SNF chromatin remodeling complex in the cancer cells derived from the subject. In one embodiment of any one method described herein, the subject would have been diagnosed with cancer.

In one embodiment of any one method described herein, the method further comprises determining for a mutation in B-Raf in the cancer cells of the subject. For example, V600E, V600K, V600L, V600R, V600M, K601E D594G, G469A, G469V, G466V, L597R, N581S, L597Q, G466, R461I, I462S, G463E, G463V G465A, G465E, G465V, G468E, N580S, E585K, D593V, F594L, G595R, L596V, T598I, V599D, V599E, V599K, and V599R.

In one embodiment, provided herein is an inhibitor of a histone methyltransferase, an inhibitor of a histone demethylase, a HDAC inhibitor, a bromodomain (BRD) inhibitor, B-Raf inhibitor, or combinations thereof, for use in the treatment of cancer in a subject when the cancer of the subject has been determined to have an alteration in the SWI/SNF chromatin remodeling complex.

In one embodiment, provided herein is a combination of inhibitors comprising a histone methyltransferase and at least a second inhibitor selected from the group consisting of an inhibitor of a histone demethylase, a HDAC inhibitor, a bromodomain (BRD) inhibitor, and a B-Raf inhibitor for use in the treatment of cancer in a subject when the cancer of the subject has been determined to have an alteration in the SWI/SNF chromatin remodeling complex.

In one embodiment, provided herein is a composition comprising a histone methyltransferase inhibitor and at least a second inhibitor selected from the group consisting of an inhibitor of a histone demethylase, a HDAC inhibitor, a bromodomain (BRD) inhibitor, and a B-Raf inhibitor for use in the treatment of cancer in a subject when the cancer of the subject has been determined to have an alteration in the SWI/SNF chromatin remodeling complex.

In one embodiment, provided herein is use of an inhibitor of a methyltransferase, an inhibitor of a histone demethylase, a HDAC inhibitor, a bromodomain (BRD) inhibitor, or BRaf (B-Raf) inhibitors, or combinations thereof, for use in the treatment of cancer in a subject or for use in the manufacture of medicament for the treatment of cancer in a subject, when the cancer of the subject has been determined to have an alteration in the SWI/SNF chromatin remodeling complex.

In one embodiment, provided herein is use of a combination of a histone methyltransferase and at least a second inhibitor selected from the group consisting of an inhibitor of a histone demethylase, a HDAC inhibitor, a bromodomain (BRD) inhibitor, or B-Raf inhibitor for the treatment of cancer in a subject when the cancer of the subject has been determined to have an alteration in the SWI/SNF chromatin remodeling complex.

In one embodiment, provided herein is use of a composition comprising a histone methyltransferase inhibitor and at least a second inhibitor selected from the group consisting of an inhibitor of a histone demethylase, a HDAC inhibitor, a bromodomain (BRD) inhibitor, or B-Raf inhibitor for the manufacture of medicament for the treatment of cancer in a subject when the cancer of the subject has been determined to have an alteration in the SWI/SNF chromatin remodeling complex.

In one embodiment, the inhibitors described herein, inhibitors of HDAC, histone demethylase B-Raf, and BRD are small molecules.

In one embodiment of any method described herein, the BRD inhibitor targets the BRD4 protein which recognizes histone 3 (H3), and histone 4 (H4) acetylated lysine residues. BRD4 is a member of the BET (bromodomain and extra terminal domain) family, which also includes BRD2, BRD3, and BRDT. BRD4, similar to other BET family members, contains two bromodomains that recognize acetylated lysine residues.

In one embodiment, non-limiting examples of the BRD inhibitor that can be used for the treatment of cancers with alterations the SWI/SNF chromatin remodeling complex include OTX015, CPI-203, PFI-3, PFI-4, GSK1324726A (I-BET726), MS436, OF-1, bromosporine, SGC-CBP30, GSK2801 ZEN3365, JQ1, PF-1, RVX-208, PFI-1 (PF-6405761), I-BET151 (GSK1210151A) and TEN010.

In one embodiment, non-limiting examples of the histone demethylase inhibitor that can be used for the treatment of cancers with alterations the SWI/SNF chromatin remodeling complex include GSKJ4, GSK J1, OG-L002, JIB-04, SP2509, ORY-1001 (RG-6016), IOX1, GSK-LSD1 2HCl, and GSK J1.

In one embodiment, the HDAC inhibitor is a pan-HDAC inhibitor, that affecting more than one class of HDAC (classes I, II, III and IV) and more than one of HDAC1, 2, 3, 4, 5, 6, 7, 8, 9, 10, and 11.

In one embodiment, non-limiting examples of the HDAC inhibitor that can be used for the treatment of cancers with alterations the SWI/SNF chromatin remodeling complex include M344, Vorinostat (suberoylanilide hydroxamic acid, SAHA, MK0683), entinostat (MS-275), panobinostat (LBH589), trichostatin A (TSA), mocetinostat (MGCD0103), Belinostat (PXD101), Romidepsin (FK228, Depsipeptide), MC1568, Tubastatin A HCl, Givinostat (ITF2357), LAQ824 (Dacinostat) CUDC-101 Quisinostat (JNJ-26481585) 2HCl, Pracinostat (SB939) PCI-34051 Droxinostat Droxinostat PCI-24781 (Abexinostat), RGFP966, AR-42, Rocilinostat (ACY-1215), Valproic acid sodium salt (Sodium valproate), CI994 (Tacedinaline), CUDC-907, Tubacin, RG2833 (RGFP109), Resminostat Sodium Phenylbutyrate, Tubastatin A, HPOB, Tasquinimod, 4SC-202 TMP269 CAY10603 BRD73954 BG45 LMK-235, and Nexturastat A.

In one embodiment, non-limiting examples of the BRaf inhibitor that can be used for the treatment of cancers with alterations the SWI/SNF chromatin remodeling complex include BAY43-9006 (Sorafenib, Nexavar), PLX4032 (Vemurafenib), GDC-0879, SB590885 S7108 Encorafenib (LGX818), RAF265 (CHIR-265), Dabrafenib (GSK2118436), TAK-632, PLX-4720, CEP-32496, Sorafenib Tosylate (Bay 43-9006), Sorafenib Sorafenib, and AZ 628.

In one embodiment provided herein is a method for treating cancer, comprising administering to a subject in needs thereof a therapeutically effective amount of a histone methyltransferase inhibitor wherein the cancer cells from a subject have been determined to have an at least 3-fold increase of H3K9me2 levels compared to reference levels.

In one embodiment provided herein is a method for treating cancer, the method comprising determining the levels of H3K9me2 in a sample of cancer cells derived from a subject, and administering to a subject a composition comprising a histone methyltransferase inhibitor when the H3K9me2 level are increased at least 3-fold compared to reference levels.

H3K9me2 is a post translational modification in which methyl groups are transferred to amino acids of histone proteins that comprise the nucleosomes. Methylation of histones has been shown to either increase or decrease gene transcription, dependent on the particular amino acid in which the methyl group has been transferred to. H3K9me2 specifically refers to the demethylation of histone H3 at the lysine 9. H3K9me2 is one of the prominent indicators of transcriptional repression. Dimethylation, in which the lysine residue is methylated twice, ensures that the bound DNA is inactive.

H3K9me2 is often observed in the insulin gene, specifically in Hela cells and human bone marrow-derived mesenchymal stem cells and repress it, whereas Human islet-derived precursor cells that express insulin does not show occupation of H3K9me2 at the insulin locus. Demethylation of H3K9me2 has been observed at the Oct4 and Nanog loci during the process of reprogramming. Misregualtion of H3K9me2 has previously been associated with prostate cancer, kidney cancer, fragile X syndrome, gastric cancer, diabetes, acute myeloid leukemia, Hodgkin's lymphoma, and prostate cancer.

Methods for measuring H3K9me2 are well known in the art. For example, one skilled in the art can determine the levels of H3K9me2 by probing cell lysates with an anti-H3K9me2 antibody using western blotting techniques. One skilled in the art could also utilize the anti-H3K9me2 antibody for immunohistochemistry to visualize H3K9me2 in a sample. A skilled person can also utilize an ELISA assay to determine the level of K3K9me2 in sample derived from a subject. An anti-H3K9me2 antibody is commercially available and can be purchased, for example by Abcam (Cambridge, Mass.).

In one embodiment, H3K9me2 levels are increased at least 3-fold compared to a reference level. In one embodiment, H3K9me2 levels are increased at least 1-fold, at least 2-fold, at least 3-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, at least 100-fold or more compared to reference levels. Used herein, "reference level" can refer to H3K9me2 levels in a melanocyte cell or tissue. The reference level can also refer to H3K9me2 levels in a non-melanocyte tissue. For example, the H3K9me2 level in a non-cancerous tissue. The reference level can be determined from a subject that has not been diagnosed with cancer. Alternatively, the reference level can be determined from a subject that has been diagnosed with cancer, but was measured in a non-cancerous tissue, for example a tissue adjacent to a cancerous tissue. The reference level can be determine in a subject that has been diagnosed with cancer at a time point prior to being diagnosed, for example, a prior biopsy that did not indicate that cancer was present.

In one embodiment, the cancer cells that have been determine to have increased H3K9me2 levels compared to reference levels have further been determined to have an at least one additional gene copy of the G9a and/or GLP gene compared to reference gene copy numbers.

The G9a gene encodes a methyltransferase that methylates lysine residue 9 of histone H3. Methylation of H3 at residue 9 by the G9a gene product results in recruitment of additional epigenetic regulators and gene repression. G9a sequences are known for a number of species, e.g., human G9a (NCBI Gene ID: 10919) and mRNA (NCBI Ref Seq NM_001289413.1). G9a can refer to human G9a, including naturally occurring variants, isoforms, and alleles thereof. Homologs and/or orthologs of human G9a are readily identified for such species by one of skill in the art, e.g., using the NCBI ortholog search function or searching available sequence data for a given species for sequence similar to a reference G9a sequence.

Experimental findings described herein have identified G9a as a bona fide oncogene, meaning that its misregulation can transform a cell into a cancer cell under the correct conditions. Increased expression of G9a due to increased gene copies have been shown to correlate with a poor prognosis for melanoma patients, and is associated with an increase of dimethylation of H3 at lysine 9. In addition, amplification of the G9a gene locus, 6p21, directly results in cancer and tumorgenesis. Moreover, G9a is essential for the growth and survival of 6p21-amplified cancer.

The GLP gene, also known as euchromatic histon-lysine N-methyltranserase 1 (EMHT1), is similar to G9a and encodes a methyltransferase that methylates lysine residue 9 of histonE H3. The gene product of GLP may be involved in the silencing of MYC- and E2F-responsive genes and therefore could play a role in the G0/G1 cell cycle transition. Defects in this gene are a cause of chromosome 9q subtelomeric deletion syndrome (9q-syndrome, also known as Kleefstra syndrome). GLP sequences are known for a number of species, e.g., human GLP (NCBI Gene ID: 79813) and mRNA (NCBI Ref Seq NM_001145527.1). GLP can refer to human GLP, including naturally occurring variants, isoforms, and alleles thereof. Homologs and/or orthologs of human GLP are readily identified for such species by one of skill in the art, e.g., using the NCBI ortholog search function or searching available sequence data for a given species for sequence similar to a reference GLP sequence.

The number of gene copies in a cell can be measured using techniques known in the art. For example, one skilled in the art can utilize fluorescence in situ hybridization (FISH) or genome sequencing to evaluate the number of gene copies in a cell for a particular gene. In addition, one could assess the levels of gene product in a cell by using methods described above, such as western blotting, immunohistochemistry, or ELISA.

In one embodiment, the cancer cells that exhibit an increase in H3K9me2 levels compared to a reference level have further been determined to have an at least 1 additional gene copy of the G9a and/or GLP gene compared to a reference gene copy number. In one embodiment, the cancer cells that exhibit an increase in H3K9me2 levels compared to a reference level have further been determined to have an at least 2, at least 3, at least 4, at least 5, at least 6, at least 7, at least 8, at least 9, at least 10 or more additional copies of the G9a and/or GLP gene compared to a reference gene copy number. Used herein, a "reference gene copy number" refers to the G9a and/or GLP gene copy number in a healthy tissue. A healthy, non-cancerous cell has 2 copies of the G9a and GLP genes.

In one embodiment of any method described herein, the composition or the inhibitor described herein or combination thereof inhibits the growth of a tumor such that the tumor is at least 10% decreased in size. In some embodiments of any method described herein, the composition or the inhibitor described herein or combination thereof inhibits the growth of a tumor such that the tumor is at least 20%, at least 30%, at least 40%, at least 50%, at least 60%, at least 70%, at least 80%, at least 90%, at least 1-fold, at least 2-fold, at least 5-fold, at least 10 fold, at least 100 fold, at least 1000-fold, or more decreased in size compared to the control size of the tumor prior to treatment in which no inhibitor is added.

In one embodiment of any method described herein, the composition or the inhibitor described herein or combination thereof further comprises a pharmaceutically acceptable carrier.

In one embodiment of any one method described herein, the inhibitors described herein is formulated as a composition. For example, formulated as a composition for an oral or systemic administration. In another embodiment, the composition is formulated for sustained delivery in vivo.

In one embodiment of any one method described herein, the compositions described herein are formulated for oral or systemic application to the subject. In one embodiment of any one method described herein, the compositions described herein are formulated for sustained delivery in vivo.

In one embodiment of any method described herein, the inhibitor described herein or combination thereof or composition is administered in conjunction with at least one additional cancer therapy to achieve a combination cancer therapy.

In one embodiment of any method described herein, the at least one additional cancer therapy is selected from chemotherapy, radiation therapy, immunotherapy, surgery, hormone therapy, stem cell therapy, targeted therapy, gene therapy, and precision therapy.

In one embodiment of any method described herein, the inhibitor described herein or combination thereof is administered by a route selected from the group consisting of oral, intravenous, intramuscular, subcutaneous, intradermal, transdermal, topical, intraperitoneal, intrathecal, intrapleural, intrauterine, rectal, vaginal, intrasynovial, intraocular/periocular, intratumor, aerosol, and parenteral administration.

In one embodiment of any method described herein, the subject is a mammal.

In one embodiment of any method described herein, the mammal is a human.

In one embodiment of any method described herein, wherein the subject is a mammal. In another embodiment, the subject is a primate mammal. In other embodiment, the subject is human.

Formulation and Application

In one embodiment, the inhibitors described herein are applicable to the treatment of cancer; the method as disclosed herein is applicable to all carcinomas, blood-borne cancers and sarcomas. Preferably, the cancer is selected from the group consisting of papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma, sinonasal undifferentiated carcinoma, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma, that are found in the anus, bladder, bile duct, bone, brain, breast, cervix, colon/ rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

Therapeutic compositions or pharmaceutical compositions comprising the inhibitors described herein can be formulated for passage through the blood-brain barrier or direct contact with the endothelium. In some embodiments, the compositions or inhibitors described herein can be formulated for systemic delivery. In some embodiments, the compositions or inhibitors described herein can be formulated for delivery to specific organs, for example but not limited to the liver, spleen, the bone marrow, and the skin. Therapeutic compositions or pharmaceutical compositions comprising the inhibitors described herein can be formulated for aerosol application by inhalation the lung. Alternatively, the therapeutic compositions or pharmaceutical compositions comprising the inhibitors described herein can also be formulated for a transdermal delivery, e. g. a skin patch. Therapeutic compositions or pharmaceutical compositions comprising the inhibitors described herein can also be enteric coated and formulated for oral delivery. Therapeutic compositions or pharmaceutical compositions comprising the inhibitors described herein can be encapsulated in liposomes or nanoparticles and formulated for slow sustained delivery in vivo. Alternatively, the therapeutic compositions or pharmaceutical compositions comprising the inhibitors described herein are formulated for targeted delivery, e.g., encapsulated in liposomes or nanoparticles that are designed and feature targeting moiety to on the liposomes or nanoparticles.

The inhibitors and the compositions described herein can be administered by any known route. By way of example, the inhibitors and the compositions described herein can be administered by a mucosal, pulmonary, topical, or other localized or systemic route (e.g., enteral and parenteral). The inhibitors may be administered by any convenient route, for example by infusion or bolus injection, by absorption through epithelial or mucocutaneous linings (e.g., oral mucosa, rectal and intestinal mucosa, etc.) and may be administered together with other biologically active agents.

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intratumoral, intrasternal, intrathecal, intrauterine, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings is administered to the patient. In various embodiments, administration can be inhaled in to the lung via aerosol administration, e.g. with nebulization. Administration also can be systemic or local. Intratumoral delivery is also included.

For example, the inhibitors or compositions comprising the described inhibitors can be administered as a formulation adapted for passage through the blood-brain barrier or direct contact with the endothelium. In some embodiments, the inhibitors or compositions described herein can be administered as a formulation adapted for systemic delivery. In some embodiments, the inhibitors or compositions described herein can be administered as a formulation adapted for delivery to specific organs, for example but not limited to the liver, spleen, the bone marrow, and the skin.

In addition, the inhibitors or compositions described herein can be administered together with other components of biologically active agents, such as pharmaceutically acceptable surfactants (e.g., glycerides), excipients (e.g., lactose), carriers, diluents and vehicles.

The inhibitors or compositions comprising the described inhibitors can be administered more than once to a subject. For example, once every three days or once a week for a period of six or eight weeks treatment protocol.

When more than one inhibitor or composition comprising the described inhibitors are to be administered to a subject, whether in conjunction with at least one other cancer therapy, the inhibitors, composition, at least one other cancer therapy are administered simultaneously or sequentially. In one embodiment, the at least one other cancer therapy does not comprise an inhibitor of a histone demethylase, a HDAC inhibitor, a bromodomain (BRD) inhibitor, or B-Raf inhibitor, or a histone methyltransferase inhibitor described herein.

The inhibitors or compositions comprising the described inhibitors can be administered therapeutically to a subject prior to, simultaneously with (in the same or different compositions) or sequentially with the administration of at least one other cancer therapy. For example, the addition cancer therapy is radiation or chemotherapy or proton therapy. The inhibitors or compositions described herein antagonists can be administered as adjunctive and/or concomitant therapy to a cancer therapy.

For parenteral (e.g., intravenous, subcutaneous, intramuscular) administration, inhibitors or compositions described herein described herein can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

The inhibitors in the formulations and compositions as disclosed herein are particularly useful in methods for promoting apoptosis of a tumor in a mammal. The inhibitors in the formulations and compositions as disclosed herein administered at such sites and in such varied ways prevent or inhibit the development and growth of the tumor. Tumors which may be prevented or inhibited by promoting or enhancing apoptosis include but are not limited to melanoma, adenocarcinoma, sarcomas, thymoma, lymphoma, lung tumors, liver tumors, colon tumors, kidney tumors, non-Hodgkins lymphoma, Hodgkins lymphoma, leukemias, uterine tumors, breast tumors, prostate tumors, renal tumors, ovarian tumors, pancreatic tumors, brain tumors, testicular tumors, bone tumors, muscle tumors, tumors of the placenta, gastric tumors, metastases and the like.

Actual dosage levels of active ingredients in the pharmaceutical compositions as described herein can be varied so as to obtain an amount of the active compound(s) which is effective to achieve the desired therapeutic response for a particular subject or patient. The selected dosage level will depend upon the activity of the particular inhibitor used, the type of administration composition (i.e. tablet versus liquid oral administration versus ocular versus topical versus inhaled, for example), the severity of the condition being treated and the condition and prior medical history of the patient being treated.

The phrase "therapeutically effective amount" of a compound, e.g., a histone methyltransferase inhibitor, or other inhibitor as described herein means a sufficient amount of the compound to treat disorders, at a reasonable benefit/risk ratio applicable to any medical treatment. It will be understood, however, that the total daily usage of the compositions and formulations as disclosed herein will be decided by the attending physician within the scope of sound medical judgment. A "therapeutically effective amount" as the term is used herein need not eradicate a disease. Rather, a therapeutically effective amount will at least slow progression of a disease (as non-limiting example, the growth of a tumor or neoplasm) relative to progression without the therapeutic agent. Thus, it is preferred, but not required that the therapeutic agent actually eliminate the disease.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the compositions and formulations as disclosed herein which are employed; and like factors well known in the medical arts. For example, it is well within the skill of the art to either start doses of the compound at levels lower than required to achieve the desired therapeutic effect and to gradually increase the dosage until the desired effect is achieved, or start doses of the compound at high levels and to gradually decrease the dosage until the desired effect is achieved, as appropriate for the care of the individual patient.

The compositions as disclosed herein can also be administered in prophylatically or therapeutically effective amounts. The formulations and compositions as disclosed herein can be administered along with a pharmaceutically acceptable carrier. A prophylatically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

The term "effective amount" as used herein refers to the amount of therapeutic agent of pharmaceutical composition to alleviate at least some of the symptoms of the disease or disorder. The term "effective amount" includes within its meaning a sufficient amount of pharmacological composition to provide the desired effect. The exact amount required will vary depending on factors such as the type of tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation.

Efficacy of treatment can be judged by an ordinarily skilled practitioner. As disclosed in the Examples, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment.

Efficacy for any given formulation (e.g., a histone methyltransferase inhibitor associated with block copolymer) can also be judged using an experimental animal model of cancer, e.g., wild-type mice or rats, or preferably, transplantation of tumor cells akin to that described in the Examples herein below. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

In addition, the amount of each component to be administered also depends upon the frequency of administration, such as whether administration is once a day, twice a day, 3 times a day or 4 times a day, once a week; or several times a week, for example 2 or 3, or 4 times a week.

Usually, the formulations and compositions as disclosed herein are administered from once a day to several times a day, for example 2 times a day, three times a day, or four times a day. In alternative embodiments, the formulations and compositions as disclosed herein can be administered, for example three to five times a week, if it is to be plurally administered in a given week. In some modes of administration, e.g., IV administration, it is desirable to dose less frequently, e.g., weekly or biweekly; block copolymer conjugate compounds can be useful in such a regimen.

For example, in one embodiment a suitable dose of the a histone methyltransferase inhibitor, or other inhibitor as described herein in the formulations and compositions as disclosed herein for a subject in need of treatment can be used according to conventionally used dose ranges of about 1 mg to about 2000 mg TNP-470 equivalent per kilogram of body weight. Generally however, conventional doses of fumagillol derivatives are about 0.1 mg/kg to 40 mg/kg body weight, preferably about 0.5 mg/kg to 20 mg/kg body weight as disclosed in U.S. Pat. No. 5,290,807. In alternative embodiments, where maintenance of tumor growth is the goal (i.e. the goal is to attenuate the growth of the tumor), a dose below the threshold used for chemotherapy can be used. For example, a suitable dose could be less than the conventionally used chemotherapeutic dose, for example, dose ranges of about 1 µg to 1 mg or 0.1 µg to 1 mg, or 1 mg to 10 mg histone methyltransferase inhibitor, or other inhibitor as described herein per kilogram of body weight can be used.

In some embodiments, if a histone methyltransferase inhibitor, or other inhibitor as described herein is administered once a week, it can be administered in an amount of from about 20 to about 200 mg/m2/week; preferably in an amount of from about 40 to about 180 mg/m2/week; and most preferably in an amount of from about 135 to about 175 mg/m2/week. In some embodiments, if a histone methyltransferase inhibitor, or other inhibitor as described herein is administered daily, it may be administered in an amount of from about 1 to about 10 mg/m2/day; for example in an amount of from about 1.25 to about 5 mg/m$^2$/day; or in an amount of from about 1 to about 3 mg/m$^2$/day. For continuous administration, the component is usually administered for at least five consecutive days of the week. In some embodiments, the effective amount of a composition as disclosed herein comprising a fumagillol derivative can be determined using an anti-angiogenesis assay as disclosed herein, and in some embodiments, the effective amount is less than the amount used as the conventionally effective dose. Similar dosage regimes can be applied for formulations compositions as disclosed herein that comprise a histone methyltransferase inhibitor, or other inhibitor as described herein.

In an alternative embodiment, higher dosages can be used, provided there is not unacceptable toxicity. For example, dosages in the range of about 50 to about 500 mg/m2/week or more, and sub-ranges within this range are specifically contemplated. Thus, dosages in the range of about 120 to 350 mg/m2/week, 200 to 400 mg/m2/week, etc. are specifically contemplated.

Solid dosage forms for oral administration include, for example but not limited to capsules, tablets, pills, powders and granules. In such solid dosage forms, the compositions as disclosed herein may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The active components can also be in micro-encapsulated form, if appropriate, with one or more of the above-mentioned excipients. In the preparation of pharmaceutical formulations as disclosed herein in the form of dosage units for oral administration the compound selected can be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed. The compositions can also be inhaled (pulmonary, nasal), ocular (eyedrop), sub-lingual, suppository, or topical (e.g., an ointment).

To enhance the activity of the inhibitors in treatment, use of adjunct treatments is contemplated. In particular, a histone methyltransferase inhibitor, or other inhibitor as described herein can be tested in conjunction with treatment with various other drugs to enhance efficacy for treatment of cancer as discussed elsewhere herein.

Soft gelatin capsules can be prepared with capsules containing a mixture of the active compound or compounds of the invention in vegetable oil, fat, or other suitable vehicle for soft gelatin capsules. Hard gelatin capsules can contain granules of the active compound. Hard gelatin capsules can also contain the targeted delivery composition including the targeting moiety and the carrier particle as well as the therapeutic agent in combination with solid powdered ingredients such as lactose, saccharose, sorbitol, mannitol, potato starch, corn starch, arnylopectin, cellulose derivatives or gelatin.

Liquid dosage forms for oral administration include pharmaceutically acceptable emulsions, solutions, suspensions, syrups and elixirs. In addition to the active components, the liquid dosage forms may contain inert diluents commonly used in the art such as, for example, water or other solvents that are compatible with the maintenance of a micelle of a diblock copolymer as described herein. Liquid preparations for oral administration can also be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol provided that such solvent is compatible with maintaining the micelle form. If desired, such liquid preparations can contain coloring agents, flavoring agents, saccharin and carboxymethyl cellulose or other thickening agents. Liquid preparations for oral administration can also be prepared in the form of a dry powder to be reconstituted with a suitable solvent prior to use.

Besides inert diluents, the oral compositions may also include adjuvants such as wetting agents, emulsifying and suspending agents, sweetening, flavoring and perfuming agents Transdermal patches may also be used to provide controlled delivery of the formulations and compositions as disclosed herein to specific regions of the body. Such dosage forms can be made by dissolving or dispensing the component in the proper medium. Absorption enhancers can also be used to increase the flux of the compound across the skin. The rate can be controlled by either providing a rate-controlling membrane or by dispersing the compound in a polymer matrix or gel. Such transdemal patches are useful for treating parts of the body where abnormally stimulated neovascularization occurs, such as inflammatory diseases, for example rheumatism and psoriasis among others, diabetic retinopathy and cancer, for example skin cancer or other skin related neovascular conditions (such as psoriasis) or malignancies.

In an alternative embodiment, the compositions and formulations as disclosed herein can be also administered via rectal or vaginal administration. In such embodiments, the compositions and formulations as disclosed herein can be in the form of suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active component.

Dosage units for rectal or vaginal administration can be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

To further protect the active ingredient, the a histone methyltransferase inhibitor, or other inhibitor as described herein can be used in admixture or in combination with a gastric acid secretion-inhibitor and/or an antacid.

Gastric acid secretion inhibitors include, for example H2 blockers (e.g. famotidine, cimetidine, ranitidine hydrochloride, etc.) and proton pump inhibitors (e.g. lansoprazole, omeprazole, etc.). As an antacid, compounds which elevate the intragastric pH level, such as magnesium carbonate, sodium hydrogen carbonate, magnesium hydroxide, magnesium oxide and magnesium hydroxide can be employed. The oral dosage forms of the compositions and formulations as disclosed herein can be administered after the intragastric pH has been increased to alleviate the influence of gastric acid by the administration of a gastric acid secretion inhibitor and/or antacid.

Alternatively, compositions and formulations as disclosed herein can be in a form of enteric-coated preparation for oral administration comprising a histone methyltransferase inhibitor, or other inhibitor as described herein. The inhibitor can be in a form as block copolymer conjugate. In some embodiments, a histone methyltransferase inhibitor, or other inhibitor as described herein is in a containing core for coating with an enteric coating film. This can be prepared using an oleaginous base or by other known formulation methods without using an oleaginous base. In some embodiments, the compositions and formulations as disclosed herein in the form of the drug-containing core for coating with a coating agent may be, for example, tablets, pills and granules.

The excipient contained in the core is exemplified by saccharides, such as sucrose, lactose, mannitol and glucose, starch, crystalline cellulose and calcium phosphate. Useful binders include polyvinyl alcohol, hydroxypropyl cellulose, macrogol, Pluronic F-68, gum arabic, gelatin and starch. Useful disintegrants include carboxymethyl cellulose calcium (ECG505), crosslinked carboxymethylcellulose sodium (Ac-Di-Sol), polyvinylpyrrolidone and low-substituted hydroxypropyl cellulose (L-HPC). Useful lubricants and antiflocculants include talc and magnesium stearate.

The enteric coating agent is an enteric polymer which is substantially insoluble in the acidic pH and is at least partially soluble at weaker acidic pH through the basic pH range. The range of acidic pH is about 0.5 to about 4.5, preferably about 1.0 to about 2.0. The range of weaker acidic pH through basic pH is about 5.0 to about 9.0, preferably about 6.0 to about 7.5. Specifically, cellulose acetate phthalate, hydroxypropylmethylcellulose phthalate, hydroxypropylmethyl acetate succinate (Shin-Etsu Chemicals), methacrylic copolymers (Rhon-Pharma, Eudragit® L-30D-55, L100-55, L100, 5100, etc.), etc. can be mentioned as examples of the enteric coating agent. These materials are effective in terms of stability, even if they are directly used as enteric compositions.

In the case of forming micelles, for example, spherical microparticles having particle diameters of about 0.01 μm to about 1000 μm are generated, or more preferably about 0.01 to about 5 μm (about 10 nm to about 5,000 nm). This formation can be performed by the methods as disclosed in the Examples or as disclosed in Japanese Patent Application JP-A-223533/1991. In some embodiments, micelles between 50 and 500 nm are useful in the compositions as disclosed herein, for example about 50-100 nm, 100-150 nm, 150-200 nm, 200-250 nm, 250-300 nm, 300-350 nm, 350-400 nm, 450-500 nm. In some embodiments, the micelles are about 130 nm as disclosed in the examples.

The concentration or content of the histone methyltransferase inhibitor, or other inhibitor as described herein in the composition can be appropriately selected according to the physicochemical properties of the composition. When the composition is in a liquid form, the concentration is about 0.0005 to about 30% (w/v) and preferably about 0.005 to about 25% (w/v). When the composition is a solid, the content is about 0.01 to about 90% (w/w) and preferably about 0.1 to about 50% (w/w).

If necessary, additives such as a preservative (e.g. benzyl alcohol, ethyl alcohol, benzalkonium chloride, phenol, chlorobutanol, etc.), an antioxidant (e.g. butylhydroxyanisole, propyl gallate, ascorbyl palmitate, alpha-tocopherol, etc.), and a thickener (e.g. lecithin, hydroxypropylcellulose, aluminum stearate, etc.) can be used in the compositions and formulations as disclosed herein.

It is noted that diblock copolymer conjugates as described generally need no further emulsifiers. Nonetheless, if necessary, one can use an additional emulsifier with the compositions and formulations as disclosed herein. Examples of emulsifiers that might be used include pharmaceutically acceptable phospholipids and nonionic surfactants. The emulsifiers can be used individually or in combinations of two or more. The phospholipid includes naturally occurring phospholipids, e.g. egg yolk lecithin, soya lecithin, and their hydrogenation products, and synthetic phospholipids, e.g. phosphatidylcholine, phosphatidylethanolamine, etc. Among them, egg yolk lecithin, soya lecithin, and phosphatidylcholine derived from egg yolk or soybean are preferred. The nonionic surfactant includes macro-molecular surfactants with molecular weights in the range of about 800 to about 20000, such as polyethylene-propylene copolymer, polyoxyethylene alkyl ethers, polyoxyethylene alkylarylethers, hydrogenated castor oil-polyoxyethylene derivatives, polyoxyethylene sorbitan derivatives, polyoxyethylene sorbitol derivatives, polyoxyethylene alkyl ether sulfate, and so on. The proportion of the emulsifier is selected so that the concentration in a final administrable composition will be in the range of about 0.1 to about 10%, preferably about 0.5 to about 5%.

In addition to the above-mentioned components, a stabilizer for further improving the stability of the compositions and formulations as disclosed herein, such as an antioxidant or a chelating agent, an isotonizing agent for adjusting the osmolarity, an auxiliary emulsifier for improving the emulsifying power, and/or an emulsion stabilizer for improving the stability of the emulsifying agent can be incorporated. The isotonizing agent that can be used includes, for example, gylycerin, sugar alcohols, monosaccharides, disaccharides, amino acids, dextran, albumin, etc. These isotonizing agents can be used individually or in combination, with two or more. An emulsion stabilizer that can be used, which includes cholesterol, cholesterol esters, tocopherol, albumin, fatty acid amide derivatives, polysaccharides, polysaccharide fatty acid ester derivatives, etc.

The compositions and formulations as disclosed herein can further comprise a viscogenic substance which can adhere to the digestive tract mucosa due to its viscosity expressed on exposure to water. The examples of the viscogenic substance include, but are not particularly limited as long as it is pharmaceutically acceptable, such as polymers (e.g. polymers or copolymers of acrylic acids and their salts) and natural-occurring viscogenic substances (e.g. mucins, agar, gelatin, pectin, carrageenin, sodium alginate, locust bean gum, xanthan gum, tragacanth gum, arabic gum, chitosan, pullulan, waxy starch, sucralfate, curdlan, cellulose, and their derivatives). Furthermore, for controling the release of the active drug or for formulation purposes, the additives conventionally used for preparing the oral compositions can be added. Example of the additives include excipients (e.g. lactose, corn starch, talc, crystalline cellulose, sugar powder, magnesium stearate, mannitol, light anhydrous silicic acid, magnesium carbonate, calcium carbonate, L-cysteine, etc.), binders (e.g. starch, sucrose, gelatin, arabic gum powder, methylcellulose, carboxymethylcellulose, carboxymethylcellulose sodium, hydroxypropylcellulose, hydroxypropylmethylcellulose, polyvinylpyrrolidone, pullulan, dextrin, etc.), disintegrators (e.g. carboxymethylcellulose calcium, low-substituted hydroxypropylcellulose, croscarmellose sodium, etc.), anionic surfactants (e.g. sodium alkylsulfates etc.), nonionic surfactants (e.g. polyoxyethylene sorbitan fatty acid esters, polyoxyethylene fatty acid esters, polyoxyethylene-castor oil derivatives, etc.), antacids and mucous membrane protectants (e.g. magnesium hydroxide, magnesium oxide, aluminum hydroxide, aluminum sulfate, magnesium metasilicate aluminate, magnesium silicate aluminate, sucralfate, etc.), cyclodextrin and the corresponding carboxylic acid (e.g. maltosyl-beta-cyclodextrin, maltosyl-beta-cyclodextrin-carboxylic acid, etc.), colorants, corrigents, adsorbents, antiseptics, moistening agents, antistatic agents, disintegration retardants, and so on. The proportion of these additives can be appropriately selected from the range that can keep the stability and absorption of the basis.

The compositions and formulations as disclosed herein for oral administration may also include flavoring agents. Such agents include, for example, anise oil, lavender oil, lemon oil, orange essence, rose oil, powder green tea, bergamot oil, (alpha[litre]) borneol, Natural Peal Extract AH-10, Sugar, bitter essence, pine flavor etc.

In the case of forming micelles, for example, spherical microparticles having particle diameters of about 0.1 nm to about 1000 nm, this formation can be achieved by methods known in the art (e.g. JP-A-223533/1991). In some embodiments, micelles between 50 and 500 nm are useful in the compositions as disclosed herein, for example about 50-100 nm, 100-150 nm, 150-200 nm, 200-250 nm, 250-300 nm, 300-350 nm, 350-400 nm, 450-500 nm. In some embodiments, the micelles are about 130 nm as disclosed in the examples.

The compositions and formulations as disclosed herein are useful as a medicament for prevention and treatment benign and malignant tumors (e.g. gastric cancer, cancer of the esophagus, duodenal cancer, cancer of the tongue, pharyngeal cancer, brain tumors, neurilemoma, colorectal cancer, non-small-cell lung cancer, small cell carcinoma of the lung, hepatic carcinoma, renal cancer, cancer of the breast, biliary tract cancer, cancer of the pancreas, cancer of the prostate, cancer of the uterus, carcinoma of the uterine cervix, ovarian cancer, cancer of the urinary bladder, cancer of the skin, malignant melanoma, cancer of the thyroid, sarcomas of bone, hemangioma, hemangiofibroma, retinal sarcoma, cancer of the penis, solid tumors of childhood, and Kaposi's sarcoma in AIDS, etc., inclusive of recurrencies and metastases to other organs). It is particularly useful when the dosage form of the compositions and formulations as disclosed herein insures an effective blood concentration within the range not causing expression of the side effects of the active substance in prolonged time, or not contributing to new side effects due to prolonged blood circulation or depoting in organ tissue for lack of renal or other clearance mechanism.

It can be advantageous, however, from the standpoint of stability, that the compositions and formulations as disclosed herein are filled into capsule shells coated with an enteric coating agent as mentioned above for use as an enteric composition. As the capsule shell, for example, soft capsules (e.g. the product of R. P. Sealer) and hard gelatin capsules are used.

The liquid or solid compositions and formulations as disclosed herein can be administered orally. In the case of the liquid form, it can be directly administered e.g., by drinking an elixir or suspension of the composition, or alternatively, into the digestive tract via a catheter or sonde for oral administration or administered in the usual manner in the unit dosage form of a hard capsule or a soft capsule. In the case of the solid form, it can be administered orally as powders, capsules, tablets, or the like in the usual manner. It can also be redispersed in a suitable dispersion medium and administered in a liquid form. Taking a patient of breast cancer (body weight: 50 kg) as an example, the oral dose of the composition as disclosed herein is about 1 mg to about 3 g/day, preferably about 10 mg to about 1 g/day, of a histone methyltransferase inhibitor, or other inhibitor as described herein. In some embodiments, the oral dose of the composition as disclosed herein is between the ranges of about 25 mg to about 1 g/day, and in some embodiments less than 25 mg to 1 g/day, for example about 10 mg to about 0.5 g/day, of a histone methyltransferase inhibitor, or other inhibitor as described herein.

Suspensions, in addition to the active components, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In one embodiment, the delivery is by intranasal administration of the composition, especially for use in therapy of the brain and related organs (e.g., meninges and spinal cord). Along these lines, intraocular administration is also possible. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

In one embodiment, the present invention encompasses combination therapy in which the formulations and compositions as disclosed herein are used in combination with a chemotherapeutic agent such as Taxol, cyclophosphamide, cisplatin, gancyclovir and the like. The chemotherapeutic agent may also be included within a micelle as described herein. Such a therapy is particularly useful in situations in which the subject or patient to be treated has a large preexisting tumor mass which is well vascularized. The chemotherapeutic agent serves to reduce the tumor mass and the conjugate prevents or inhibits neovascularization within or surrounding the tumor mass. The chemotherapeutic agent may also be administered at lower doses than normally used and at such doses may act as an anti-proliferative agent. The second therapy can be administered to the subject before, during, after or a combination thereof relative to the administration of the compositions as disclosed herein. Anti-proliferative therapies are well known in the art and are encompassed for use in the methods of the present invention. Therapies includes, but are not limited to an alkylating agent, mitotic inhibitor, antibiotic, or antimetabolite, anti-angliogenic agents etc. Such chemotherapy can comprise administration of CPT-11, temozolomide, or a platin compound. Radiotherapy can include, for example, x-ray irradiation, w-irradiation, γ-irradiation, or microwaves.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cis-platinum, methotrexate, and alkaloids such as vindesine and vinblastine.

In another embodiment, the present invention encompasses combination therapy in which the formulations and compositions as disclosed herein are used in combination with, a cytostatic agent, anti-VEGF and/or p53 reactivation agent. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics include inhibitors of matrix metalloproteinases such as marimastat, growth factor antagonists, signal transduction inhibitors and protein kinase C inhibitors.

In another embodiment, the methods described herein are administered in conjunction with an anti-VEGF agent. Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by Aspergillus fumigates. As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (Astra-Zeneca), ZD4190 which inhibits VEGF-R2 and -R1 (Astra-Zeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æterna Zentaris Inc; Quebec City, Calif.) and combinations thereof.

The dosage administered to a subject will vary depending upon a variety of factors, including the pharmacodynamic characteristics of the particular antagonists, and its mode and route of administration; size, age, sex, health, body weight and diet of the recipient; nature and extent of symptoms of the disease being treated, kind of concurrent treatment, frequency of treatment, and the effect desired.

Usually a daily dosage of active ingredient can be about 0.01 to 500 milligrams per kilogram of body weight. Ordinarily 1 to 40 milligrams per kilogram per day given in divided doses 1 to 6 times a day or in sustained release form is effective to obtain desired results. The active ingredient will ordinarily be present in an amount of about 0.5-95% by weight based on the total weight of the composition. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease. For example, second and subsequent administrations can be given between about one day to 30 weeks from the previous administration. Two, three, four or more total administrations can be delivered to the individual, as needed.

The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment.

The precise dose to be employed in the formulation of the agent will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. For example, measurements for a decrease in the size of a tumor or the number of tumors or both are performed prior to the start of a treatment and then at later specific time period after the start of the treatment. Alternately, the treatment efficacy can be determined by measuring the population of aberrant white blood cells in the subject from a sample of peripheral blood prior to and after the start of treatment.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on the type of cancer, the formulation used, route of administration, the severity of the cancer symptoms and the susceptibility of the subject to side effects. Moreover, treatment of a subject with a therapeutically effective dose can include a single treatment or a series of treatments. Estimates of effective dosages and in vivo half-lives for the inhibitors can be made using conventional methodologies or on the basis of in vivo testing using an appropriate animal model, as known in the art, or as described herein.

Those skilled in the art will recognize, or be able to ascertain using not more than routine experimentation, many equivalents to the specific embodiments of the disclosure described herein. Such equivalents are intended to be encompassed by the following claims.

Some embodiments of the technology described herein can be defined according to any of the following numbered paragraphs:

1. A method for treating cancer in a subject comprising administering to a subject in need thereof a therapeutically effective amount of an inhibitor of a histone methyltransferase, wherein the cancer cells of the subject has been determined to have an alteration in the SWI/SNF ((SWItch/Sucrose Non-Fermentable) chromatin remodeling complex.
2. The method of paragraph 1, wherein the inhibitor of a histone methyltransferase is a G9a inhibitor or a EZH2 inhibitor.
3. The method of paragraph 1 or 2, wherein the histone methyltransferase inhibitor is formulated as a composition.
4. A method for treating of cancer in a subject in need thereof, the method comprising
   a. determining an alteration of SWI/SNF chromatin remodeling complex from a sample of cancer cells derived from a subject; and
   b. administering to a subject a composition comprising an inhibitor of a histone methyltransferase when there is an alteration in the SWI/SNF chromatin remodeling complex in the cancer cells.
5. The method of any one of paragraphs 1-4, wherein the alteration the SWI/SNF chromatin remodeling complex is the result in a deficiency in one or more of the subunit member of the complex.
6. The method of paragraph 5, wherein the subunits are selected from the group consisting of BRM/SMARCA2, BRG1/SMARCA4, ARID1A; ARID2SMARCR2; SMARCR1; and SMARCB1.
7. The method of paragraph 6, wherein the deficiency is due to a mutation in the gene of the subunit member.
8. The method of paragraph 7, wherein the mutation is a deletion, a single nucleotide variant (SNV), or an amplification.
9. The method of paragraph 8, wherein the SNV is an inactivating SNV.
10. The methods of any one of paragraphs 1-9, wherein the histone methyltransferase inhibitor is a small molecule or a nucleic acid.
11. The method of paragraph 10, wherein the small molecule histone methyltransferase inhibitor is selected from the group a BIX-01294, UNC0638, A-366, chaetocin, UNC0224, UNC0631, and UNC0646.
12. The method of any of paragraphs 1-11, wherein the histone methyltransferase inhibitor is administered by a route selected from the group consisting of intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.
13. The method of any one of paragraphs 1-12, wherein the histone methyltransferase inhibitor is administered in conjunction with at least one additional cancer therapy to achieve a combination cancer therapy.
14. The method of paragraph 13, wherein the at least one additional cancer therapy is selected from chemotherapy, radiation therapy, immunotherapy, surgery, hormone therapy, stem cell therapy, targeted therapy, gene therapy and precision therapy.
15. The method of any of paragraphs 1-14, wherein the subject is a mammal.
16. The method of paragraph 15, wherein the mammal is a human.
17. The method of any of paragraphs 1-16, wherein the composition or histone methyltransferase inhibitor further comprises a pharmaceutically acceptable carrier.
18. An inhibitor of a methyltransferase for use in the treatment of cancer in a subject when the cancer of the subject has been determined to have an alteration in the SWI/SNF ((SWItch/Sucrose Non-Fermentable) chromatin remodeling complex.
19. The inhibitor of paragraph 17, wherein the wherein the histone methyltransferase inhibitor is a small molecule or a nucleic acid.
20. The inhibitor of paragraph 18, wherein the histone methyltransferase inhibitor is selected from the group a AMI-1, A-366, BIX-01294, BIX01338, BRD4770, chaetocin, UNCO224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, and EPZ-6438.
21. The inhibitor of any one of paragraphs 18-20, wherein the inhibitor is administered by a route selected from the group consisting of: oral, intravenous, intramuscular, subcutaneous, intradermal, transdermal, topical, intraperitoneal, intrathecal, intrapleural, intrauterine, rectal, vaginal, intrasynovial, intraocular/periocular, intratumor, and parenteral administration.

22. The inhibitor of any one of paragraphs 18-21, that is administered in conjunction with at least one additional cancer therapy to achieve a combination cancer therapy.

23. A method for treating of cancer in a subject in need thereof, the method comprising administering a composition comprising an inhibitor of a histone methyltransferase G9a and an inhibitor for a histone deacetylase (HDAC), wherein the cancer of the subject has been determined to have an alteration in the SWI/SNF ((SWItch/Sucrose Non-Fermentable) chromatin remodeling complex.

24. A method for treating of cancer in a subject in need thereof, the method comprising administering a composition comprising an inhibitor of a histone methyltransferase EZH2 wherein the cancer of the subject has been determined to have an alteration in the SWI/SNF ((SWItch/Sucrose Non-Fermentable) chromatin remodeling complex.

25. A method for treating of cancer in a subject in need thereof, the method comprising administering a composition comprising an inhibitor of a histone methyltransferase EZH2, and an inhibitor of a histone methyltransferase G9a, wherein the cancer of the subject has been determined to have an alteration in the SWI/SNF ((SWItch/Sucrose Non-Fermentable) chromatin remodeling complex.

26. A method for treating of cancer in a subject in need thereof, the method comprising administering a composition comprising an inhibitor of a histone methyltransferase EZH2 and an inhibitor for a histone deacetylase (HDAC), wherein the cancer of the subject has been determined to have an alteration in the SWI/SNF ((SWItch/Sucrose Non-Fermentable) chromatin remodeling complex.

27. A method for treating of cancer in a subject in need thereof, the method comprising administering a composition comprising an inhibitor of a histone methyltransferase G9a, an inhibitor of a histone methyltransferase EZH2 and an inhibitor for a histone deacetylase (HDAC), wherein the cancer of the subject has been determined to have an alteration in the SWI/SNF ((SWItch/Sucrose Non-Fermentable) chromatin remodeling complex.

28. A method for treating of cancer in a subject in need thereof, the method comprising administering a composition comprising an inhibitor of a histone methyltransferase EZH2 and an inhibitor for a B-Raf enzyme, wherein the cancer of the subject has been determined to have an alteration in the SWI/SNF ((SWItch/Sucrose Non-Fermentable) chromatin remodeling complex.

29. A method for treating of cancer in a subject in need thereof, the method comprising administering a composition comprising an inhibitor of a histone methyltransferase G9a and an inhibitor for a B-Raf enzyme, wherein the cancer of the subject has been determined to have an alteration in the SWI/SNF ((SWItch/Sucrose Non-Fermentable) chromatin remodeling complex.

30. A method for treating of cancer in a subject in need thereof, the method comprising administering a composition comprising an inhibitor of a histone methyltransferase G9a, an inhibitor of a histone methyltransferase EZH2, and an inhibitor for a B-Raf enzyme, wherein the cancer of the subject has been determined to have an alteration in the SWI/SNF ((SWItch/Sucrose Non-Fermentable) chromatin remodeling complex.

31. A method for treating of cancer in a subject in need thereof, the method comprising administering a composition comprising an inhibitor of a histone methyltransferase EZH2 and an inhibitor for a member of the BET family of bromodomain proteins (BRD), wherein the cancer of the subject has been determined to have an alteration in the SWI/SNF ((SWItch/Sucrose Non-Fermentable) chromatin remodeling complex.

32. A method for treating of cancer in a subject in need thereof, the method comprising administering a composition comprising an inhibitor of a histone methyltransferase G9a and an inhibitor for a member of the BET family of bromodomain proteins (BRD), wherein the cancer of the subject has been determined to have an alteration in the SWI/SNF ((SWItch/Sucrose Non-Fermentable) chromatin remodeling complex.

33. A method for treating of cancer in a subject in need thereof, the method comprising administering a composition comprising an inhibitor of a histone methyltransferase G9a, an inhibitor of a histone methyltransferase EZH2, and an inhibitor for a member of the BET family of bromodomain proteins (BRD), wherein the cancer of the subject has been determined to have an alteration in the SWI/SNF ((SWItch/Sucrose Non-Fermentable) chromatin remodeling complex.

34. A method for treating cancer in a subject comprising administering to a subject in need thereof a therapeutically effective amount of a histone methyltransferase inhibitor, wherein the cancer cells from the subject has been determined to have an at least 3-fold increase of H3K9me2 levels compared to a reference level.

35. The method of paragraph 34, wherein the inhibitor of a histone methyltransferase is a G9a inhibitor.

36. The method of paragraph 34, wherein the cancer cells from the subject have further been determined to have an at least 1 additional copy of the G9a and/or GLP gene compared to a reference gene copy number.

37. A method for treating cancer in a subject in need thereof, the method comprising
    a. determining the levels of H3K9me2 in a sample of cancer cells derived from a subject; and
    b. administering to said subject a composition comprising a histone methyltransferase inhibitor when there is an at least 3-fold increase of H3K9me2 levels in the cancer cells compared to a reference level.

38. The method of paragraph 37, wherein the sample of cancer cells have further been determined to have an at least 1 additional copy of the G9a and/or GLP gene compared to a reference gene copy number.

39. The method of paragraphs 34-37, wherein the composition comprising a histone methyltransferase inhibitor further comprises at least a second inhibitor selected from the group consisting of an inhibitor of a histone demethylase, a HDAC inhibitor, a bromodomain (BRD) inhibitor, and B-Raf inhibitor.

TABLE 1

A list of SWI/SNF Remodeling complex family members with alterations reported in various cancer type.

| Subunit | Gene | Cancer Types | Alterations |
|---|---|---|---|
| Core complex subunits | | | |
| BRM | SMARCA2 | Adenoid cystic carcinoma | Mutation, deletion, and amplification |
| | | Non-melanoma skin cancer | |
| | | Hepatocellular carcinoma | Mutation |
| | | Head and neck squamous cell carcinoma | Deletion |
| | | Gastric cancer | Deletion |
| | | Clear cell renal cell carcinoma | Decreased expression |
| | | Prostate cancer | Decreased expression |
| | | Lung cancer (adenocarcinoma and squamous cell carcinoma) | Decreased expression |
| BRG1 | SMARCA4 | Small-cell carcinoma of the ovary, hypercalcemic type (malignant rhabdoid tumor of the ovary) | Biallelic inactivation |
| | | Rhabdoid tumor | Biallelic inactivation |
| | | Medulloblastoma | Mutation |
| | | Lung adenocarcinoma | Mutation and deletion |
| | | Mantle cell lymphoma | Mutation |
| | | Burkitt lymphoma | Mutation |
| | | Hepatocellular carcinoma | Mutation and deletion |
| | | Esophageal adenocarcinoma | Mutation and translocation |
| | | Melanoma | Mutation |
| | | Non-melanoma skin cancer | Decreased expression |
| | | Intraductal papillary mucinous neoplasms of the pancreas | Decreased expression |
| BAF47 | SMARCB1 | Rhabdoid tumor | Biallelic inactivation |
| | | Schwannoma | Biallelic inactivation |
| | | Meningioma | Biallelic inactivation |
| | | Epitheloid sarcoma | Biallelic inactivation |
| | | Cribriform neuroepithelial tumor | Biallelic inactivation |
| | | Renal medullary carcinoma | Deletion |
| BAF155 | SMARCC1 | Colorectal carcinoma | Increased expression |
| | | Prostate cancer | Increased expression |
| | | Cervical intraepithelial neoplasia | Increased expression |
| BAF 170 | SMARCC2 | Gastric cancer | Mutation |
| | | Colorectal carcinoma | Mutation |
| BAF60A | SMARCD1 | Breast cancer | Mutation |
| | | Gastric cancer | Mutation |
| BAF60B | SMARCD2 | Lung adenocarcinoma | Mutation |
| | | Colon cancer | Mutation |
| BAF60C | SMARCD3 | Neuroblastoma | Increased expression |
| BAF57 | SMARCE1 | Multiple spinal meningiomas | Mutation and deletion |
| | | Colorectal carcinoma | Mutation |
| | | Lung adenocarcinoma | Mutation |
| BAF53B | ACTL6B | Urothelial cancer | Decreased expression |
| | | Hepatocellular carcinoma | Decreased expression |
| Beta-actin | ACTB | Pericytoma with t(7;12) | Translocation |
| | | Diffuse large B-cell lymphoma | Mutation |
| BAF complex subunits | | | |
| BAF45B | DPF1 | Esophageal adenocarcinoma | Mutation |
| Core complex subunits | | | |
| | | Lung adenocarcinoma | Mutation |
| | | Colon cancer | Mutation |
| BAF45C | DPF3 | Esophageal adenocarcinoma | Mutation |
| | | Lung adenocarcinoma | Mutation |
| | | Colorectal cancer | Mutation |
| BAF45D | DPF2 | Esophageal adenocarcinoma | Mutation |
| | | Lung adenocarcinoma | Mutation |
| | | Colorectal cancer | Mutation |
| BAF250A | ARID1A | Ovarian clear cell carcinoma | Mutation and deletion |
| | | Endometrioid ovarian carcinoma | Mutation |
| | | Endometrial carcinoma | Mutation |
| | | Cervical carcinoma | Decreased expression |

TABLE 1-continued

A list of SWI/SNF Remodeling complex family members with alterations reported in various cancer type.

| Subunit | Gene | Cancer Types | Alterations |
|---|---|---|---|
| | | Breast cancer | Mutation and deletion |
| | | Pancreatic ductal adenocarcinoma | Mutation and deletion |
| | | Pancreatic carcinoma with acinar differentiation | Mutation |
| | | Hepatocellular carcinoma | Mutation and deletion |
| | | Intrahepatic cholangiocarcinomas | Mutation |
| | | Gastric adenocarcinoma | Mutation and deletion |
| | | Esophageal adenocarcinoma | Mutation |
| | | Oseophagogastric junctional adenocarcinoma | Mutation |
| | | Colorectal carcinoma | Mutation |
| | | Renal clear cell carcinoma | Mutation |
| | | Transitional cell carcinoma of the bladder | Mutation |
| | | Urothelial bladder carcinoma | Mutation |
| | | Medulloblastoma | Mutation |
| | | Neuroblastoma | Mutation |
| | | Lung adenocarcinoma | Mutation and deletion |
| | | Pulmonary carcinoids | Mutation |
| | | Adenoid cystic carcinoma | Mutation and deletion |
| | | Prostate cancer | Mutation |
| | | Burkitt lymphoma | Mutation |
| | | Diffuse large B-cell lymphoma | Mutation |
| | | Follicular lymphoma | Mutation |
| | | Melanoma | Mutation |
| BAF250B | ARID1B | Hepatocellular carcinoma | Mutation and deletion |
| | | Colorectal carcinoma | Mutation |
| | | Breast cancer | Mutation |
| | | Prostate cancer | Mutation |
| | | Neuroblastoma | Deletion |
| | | Melanoma | Mutation |
| BCL7A | BCL7A | Pilocytic astrocytoma | Deletion |
| | | Mycosis fungoides (primary cutaneous T cell lymphoma subtype) | Deletion |
| | | Multiple myeloma | Decreased expression |
| | | Cutaneous T cell lymphoma | Decreased expression |
| BCL7B | BCL7B | Pilocytic astrocytoma | Deletion |
| | | Gastric cancer | Mutation |
| BCL7C | BCL7C | Gastric cancer | Mutation |
| BCL11A | BCL11A | Non-small cell lung cancer | Increased expression |
| | | Lung squamous cell carcinoma | Copy number amplification |
| | | Chronic lymphocytic leukemia | Translocation and copy number gain |
| | | Acute lymphoblastic leukemia | Increased expression |
| | | Acute myeloid leukemia | Translocation |
| | | Low-grade B cell lymphoma | Copy number gain |
| | | Mediastinal B cell lymphoma | Copy number gain/amplification |
| | | Diffuse large B-cell lymphoma | Copy number gain/amplification |
| | | Marginal zone B cell lymphoma | Copy number gain/amplification |
| | | Gray zone lymphoma | Copy number gain/amplification |
| | | Classical Hodgkin lymphoma | Copy number gain/amplification |
| BCL11B | BCL11B | Acute myeloid leukemia | Focal amplification/translocation |
| | | T cell acute lymphoblastic leukemia | Deletion, mutation, and gene fusions |
| | | Mycosis fungoides (primary cutaneous T cell lymphoma subtype) | Increased expression |
| | | Adult T cell leukemia/lymphoma | Decreased expression and translocation |
| | | Head and neck squamous cell carcinoma | Increased expression |
| BRD9 | BRD9 | Gastric cancer | Mutation |
| SS18L1 | CREST | Synovial sarcoma | Translocation |
| SS18 | SYT | Synovial sarcoma | Translocation |

TABLE 1-continued

A list of SWI/SNF Remodeling complex family members with alterations reported in various cancer type.

| Subunit | Gene | Cancer Types | Alterations |
|---------|------|--------------|-------------|
| PBAF complex subunits | | | |
| BAF45A | PHF10 | Colon cancer | Mutation |
| | | Hepatocellular carcinoma | Mutation |
| BAF180 | PBRM1 | Renal clear cell carcinoma | Biallelic inactivation |
| | | Intrahepatic cholangiocarcinomas | Mutation |
| | | Gallbladder carcinoma | Mutation |
| | | Breast cancer | Mutation and LOH |
| | | Esophageal adenocarcinoma | Mutation |
| BA200 | ARID2 | Hepatocellular carcinoma | Mutation and deletion |
| Core complex subunits | | | |
| | | Pancreatic ductal adenocarcinoma | Mutation and deletion |
| | | Non-small cell lung cancer | Biallelic inactivation |
| | | Colorectal carcinoma | Mutation |
| | | Esophageal adenocarcinoma | Mutation |
| | | Oral squamous cell carcinoma (gingivobuccal) | Mutation |
| | | Breast cancer | Mutation |
| | | Melanoma | Mutation |
| BRD7 | BRD7 | Epithelial ovarian carcinoma | Decreased expression |
| | | Colorectal carcinoma | Decreased expression |
| | | Nasopharyngeal carcinoma | Decreased expression |

We claim:

1. A method for treating melanoma in a subject comprising administering to a subject in need thereof a therapeutically effective amount of a small molecule inhibitor of a histone methyltransferase, wherein the histone methyltransferase comprises G9a or GLP, and wherein the melanoma cells of the subject have been determined to have an alteration in the SWI/SNF ((SWItch/Sucrose Non-Fermentable) chromatin remodeling complex,
wherein the small molecule inhibitor is selected from the group consisting of BIX-01294, UNC0638, A-366, chaetocin, UNCO224, UNC0631, UNC0642, and UNC0646.

2. The method of claim 1, wherein the alteration of the SWI/SNF chromatin remodeling complex is the result in a deficiency in one or more of the subunit member of the complex.

3. The method of claim 2, wherein the subunits are selected from the group consisting of BRM/SMARCA2, BRG1/SMARCA4, ARID1A; ARID2; SMARCR2; SMARCR1; and SMARCB1.

4. The method of claim 3, wherein the deficiency is due to a mutation in the gene of the subunit member, wherein the mutation is a deletion, a single nucleotide variant (SNV), an inactivating SNV, or an amplification.

5. The method of claim 1, wherein the small molecule inhibitor is administered by a route selected from the group consisting of intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

6. The method of claim 1, wherein the small molecule inhibitor is administered in conjunction with at least one additional cancer therapy to achieve a combination cancer therapy.

7. The method of claim 6, wherein the at least one additional cancer therapy is selected from chemotherapy, radiation therapy, immunotherapy, surgery, hormone therapy, stem cell therapy, targeted therapy, gene therapy and precision therapy.

8. The method of claim 1, wherein the subject is a mammal.

9. The method of claim 8, wherein the mammal is a human.

10. The method of claim 1, wherein the small molecule inhibitor further comprises a pharmaceutically acceptable carrier.

11. The method of claim 1, wherein the melanoma cells have been further determined to have at least one of:
a. H3K9me2 levels at least 3-fold higher as compared to a reference level of H3K9me2 levels in a reference sample, or
b. at least 1 additional copy of the G9a and/or GLP gene as compared to a reference gene copy number of the G9a and/or GLP gene in the reference sample;
wherein the reference sample is a non-melanoma cell from the subject.

* * * * *